United States Patent
Qian et al.

(10) Patent No.: US 10,598,825 B2
(45) Date of Patent: Mar. 24, 2020

(54) SOFT SILICONE MEDICAL DEVICES WITH DURABLE LUBRICIOUS COATINGS THEREON

(71) Applicant: Novartis AG, Basel (CH)

(72) Inventors: Xinming Qian, Johns Creek, GA (US); Frank Chang, Cumming, GA (US); Yasuo Matsuzawa, Canton, GA (US); Venkat Shankar, Suwanee, GA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 16/398,607

(22) Filed: Apr. 30, 2019

(65) Prior Publication Data

US 2019/0257980 A1   Aug. 22, 2019

Related U.S. Application Data

(62) Division of application No. 15/249,577, filed on Aug. 29, 2016, now Pat. No. 10,324,233.

(60) Provisional application No. 62/214,246, filed on Sep. 4, 2015.

(51) Int. Cl.
| | | |
|---|---|---|
| *G02B 1/04* | (2006.01) | |
| *A61L 27/18* | (2006.01) | |
| *A61L 27/34* | (2006.01) | |
| *A61F 2/14* | (2006.01) | |
| *C08L 83/04* | (2006.01) | |
| *A61F 2/16* | (2006.01) | |
| *A61F 9/007* | (2006.01) | |
| *A61L 12/04* | (2006.01) | |
| *C08G 77/12* | (2006.01) | |
| *C08G 77/20* | (2006.01) | |

(52) U.S. Cl.
CPC ............. *G02B 1/043* (2013.01); *A61F 2/14* (2013.01); *A61F 2/1451* (2015.04); *A61F 2/16* (2013.01); *A61F 9/00781* (2013.01); *A61L 12/04* (2013.01); *A61L 27/18* (2013.01); *A61L 27/34* (2013.01); *C08L 83/04* (2013.01); *A61F 2210/0061* (2013.01); *A61L 2400/10* (2013.01); *A61L 2400/18* (2013.01); *A61L 2430/16* (2013.01); *C08G 77/12* (2013.01); *C08G 77/20* (2013.01)

(58) Field of Classification Search
CPC ........................................ G02B 1/043
See application file for complete search history.

(56) References Cited

U.S. PATENT DOCUMENTS

| | | | | |
|---|---|---|---|---|
| 9,810,812 B2 * | 11/2017 | Qian | ................. | C08J 7/123 |
| 2016/0061995 A1 * | 3/2016 | Chang | ................. | B05D 5/00 |
| | | | | 351/159.33 |

FOREIGN PATENT DOCUMENTS

WO   2015/073758 A1   5/2015

* cited by examiner

*Primary Examiner* — Michael F Pepitone
(74) *Attorney, Agent, or Firm* — Jian Zhou

(57) ABSTRACT

The invention is related to a medical device comprising a core material made of a crosslinked silicone material and a hydrogel coating which is thermodynamically stable. The invention is also related to a method for producing such a medical device, especially a soft contact lens.

20 Claims, No Drawings

SOFT SILICONE MEDICAL DEVICES WITH DURABLE LUBRICIOUS COATINGS THEREON

This application claims the benefit under 35 U.S.C. § 119 (e) of U.S. provisional application Ser. No. 62/214,246 filed on Sep. 4, 2015, herein incorporated by reference in its entirety.

The present invention generally relates to a method for producing medical devices, especially soft contact lenses, having a core material (i.e., a silicone substrate) made of a crosslinkined silicone material and a thermodynamically-stable hydrophilic hydrogel coating thereon. In addition, the present invention provides medical devices (especially a silicone ophthalmic device) comprising a core material made of a crosslinkined silicone material and a hydrophilic, lubricious hydrogel coating which is thermodynamically stable and durable.

BACKGROUND

Cornea cannot receive oxygen from the blood supply like other tissue. When the eye is open, the cornea primarily receives oxygen from the atmosphere, via the tears. When the eye is closed (e.g., during sleep), the cornea receives oxygen mainly from oxygen diffusion from the capillary plexus of the upper palpebral aperture vasculature. If sufficient oxygen does not reach the cornea, corneal swelling occurs. Extended periods of oxygen deprivation cause the undesirable growth of blood vessels in the cornea. Wearing of a soft contact lens inevitably reduces the oxygen supply to the cornea, because it can form an oxygen barrier that prevents oxygen from reaching the cornea. The oxygen transmissibility (Dk/t) of the contact lens worn by a patient, depending upon the oxygen permeability (Dk) of the lens material and the thickness (t) of the contact lens, is of vital importance for the oxygen supply to the cornea either from the atmosphere in the open eye state or from the capillary plexus of the upper palpebral aperture vasculature.

In recent years, soft silicone hydrogel contact lenses become more and more popular because of their high oxygen transmissibility and comfort. Silicone hydrogel (SiHy) contact lenses are made of a hydrated, crosslinked polymeric material that contains silicone and from about 23% to about 75% by weight of water within the lens polymer matrix at equilibrium. Exemplary commercial SiHy lens products are Focus® Night & Day® from Alcon Corporation (ca. 23.5% $H_2O$ and Dk~140 Barrers; Air Optix® from Alcon (ca. 33% $H_2O$ and Dk~110 Barrers); DAILIES TOTAL1® from Alcon (ca. 33% $H_2O$ in bulk, >80% $H_2O$ in surface, and Dk~110 Barrers); PureVision® from Bausch & Lomb (ca. 36% $H_2O$ and Dk~140 Barrers); Ultra from Bausch & Lomb (ca. 46% $H_2O$ and Dk~114 Barrers); Acuvue® Oasys® from Johnson & Johnson (ca. 38% $H_2O$, Dk~105 Barrers); Acuvue® Advance® from Johnson & Johnson (ca. 47% $H_2O$, Dk~65 Barrers); Acuvue® TryEye™ from Johnson & Johnson (ca. 46% $H_2O$, Dk~100 Barrers); Biofinity® from CooperVision (ca. 48% $H_2O$, Dk~128 Barrers); Avaira™ from CooperVision (ca. 46% $H_2O$, Dk~100 Barrers); MyDay™ from CooperVision (ca. 54% $H_2O$, Dk~80 Barrers); and PremiO™ from Menicon (ca. 40% $H_2O$, Dk~129 Barrers); Clariti® from CooperVision (ca. 56% $H_2O$, Dk~60 Barrers); Definitive™ from Contamac, Ltd (ca. 75% $H_2O$, Dk~61 Barrers). However, a SiHy contact lens may not have a very high oxygen permeability (e.g., greater than 180 Barrers). A very high oxygen permeability is likely required for alleviating the adverse effect of oxygen-impermeable electro-optic elements, which are incorporated in contact lenses (see, U.S. Pat. Nos. 6,851,805, 7,490,936 and 8,154,804), upon the permeation of oxygen through the contact lenses.

Silicone contact lenses, made essentially of a crosslinked silicone polymer (or a silicone rubber or elastomer), have been proposed previously (U.S. Pat. Nos. 3,916,033; 3,996,187, 3,996,189; 4,332,922; and 4,632,844, herein incorporated by references in their entireties), because of their very high oxygen permeability and good mechanical and optical properties. However, because a silicone polymer is a hydrophobic material, a silicone contact lens has a hydrophobic surface and thereby is not ophthalmically with the cornea. It may irritate the corneal tissue and cause adverse event.

Recently, Matsuzawa discloses a plasma polymerization method for applying an amorphous carbon film onto the surface of a silicone contact lens (U.S. Pat. No. 9,010,933, herein incorporated by reference in its entirety). Resultant silicone contact lenses can have a very high oxygen permeability and good wettability as measured by a water contact angle (herein designated as "WCA") of about 25 degrees. However, such plasma polymerization method may not provide a silicone contact lens with a desirable surface hydrophilicity (as measured by water-breakup-time, hereinafter designated as "WBUT") and lubricity. Further, Matsuzawa has not reported whether such silicone contact lenses with an amorphous carbon film could maintain their wettability when being exposed to air or stored in a dry state for a prolong period of time. It is known that silicone has a great tendency to migrate to the surface of a substrate in the air to minimize the surface energy.

Therefore, there is still a need for an improved method for producing silicone contact lenses with a thermodynamically-stable, lubricious coating. There is also a need for silicone contact lenses with such a thermodynamically-stable, lubricious coating thereon.

SUMMARY OF THE INVENTION

In one aspect, the invention provides a method for producing a medical device (especially a silicone ophthalmic device) which includes a silicone substrate and a hydrogel coating thereon, the method of invention comprising the steps of: (1) obtaining a silicone substrate made of a crosslinked silicone material in a dry state; (2) subjecting the silicone substrate in the dry state to a surface treatment to form a base coating comprising a prime plasma layer and a reactive polymer layer, wherein the surface treatment comprises the sub-steps of (a) plasma-treating the surface of the silicone substrate in the dry state with a plasma to form the prime plasma layer on the silicone substrate, wherein the prime plasma layer has a thickness of less than about 40 nm, wherein the plasma is generated in a plasma gas (i.e., an atmosphere) composed of air, $CO_2$, or a mixture of a $C_1$-$C_6$ hydrocarbon and a secondary gas selected from the group consisting of air, $CO_2$, $N_2$, and combinations thereof, and (b) contacting the plasma-treated silicone substrate with a first aqueous solution including a reactive hydrophilic polymer to form a reactive polymer layer, wherein the reactive hydrophilic polymer has multiple reactive functional groups selected from the group consisting of carboxyl groups, primary amine groups, secondary amine groups, and combinations thereof; and (3) heating the silicone substrate with the base coating thereon obtained in step (2), in a second aqueous solution which comprises a water-soluble and thermally-crosslinkable hydrophilic polymeric material having azetidinium groups and optionally (but preferably) amino or carboxyl groups, at a temperature of from about 60° C. to about 140° C. for a time period sufficient long to crosslink the water-soluble thermally-crosslinkable hydrophilic polymeric material and the base coating so as to obtain the medical device which comprises the silicone substrate and a hydrogel coating thereon, wherein the medical device in fully hydrated state has a WBUT of at least about 5 seconds and a friction rating of about 3 or lower, wherein the hydrogel coating is thermodynamically-stable.

In another aspect, the invention provides a medical device (especially a soft ophthalmic device), comprising a silicone substrate made of a crosslinked silicone material and a hydrogel coating thereon, wherein the medical device in fully-hydrated state has a WBUT of at least about 5 seconds and a friction rating of about 3 or lower, wherein the hydrogel coating is thermodynamically stable.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF EMBODIMENTS OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

A "medical device", as used herein, refers to a device having surfaces that contact tissue, blood, or other bodily fluids of patients in the course of their operation or utility. Exemplary medical devices include: (1) extracorporeal devices for use in surgery such as blood oxygenators, blood pumps, blood sensors, tubing used to carry blood and the like which contact blood which is then returned to the patient; (2) prostheses implanted in a human or animal body such as vascular grafts, stents, pacemaker leads, heart valves, and the like that are implanted in blood vessels or in the heart; (3) devices for temporary intravascular use such as catheters, guide wires, and the like which are placed into blood vessels or the heart for purposes of monitoring or repair; (4) artificial tissues such as artificial skin for burn patients; (5) dentifices, dental moldings; (6) ophthalmic devices. In a preferred embodiment, medical devices are ophthalmic devices; and (7) cases or containers for storing ophthalmic devices or ophthalmic solutions. In a preferred embodiment, medical devices are ophthalmic devices.

An "ophthalmic device" refers to a structure that can be placed on or within a wearer's eye. Examples of preferred ophthalmic devices includes without limitation contact lenses, intraocular lenses, corneal onlay, devices under eyelid, stents, glaucoma shunt, implants, or the like.

"Contact Lens" refers to a structure that can be placed on or within a wearer's eye. A contact lens can correct, improve, or alter a user's eyesight, but that need not be the case.

A "silicone contact lens" refers to a contact lens made of a crosslinked silicone material as its bulk (or core or base) material which has three-dimensional polymer networks (i.e., polymer matrix), is insoluble in water, and can hold less than about 7.5% (preferably less than about 5%, more preferably less than about 2.5%, even more preferably less than about 1%) by weight of water when fully hydrated.

A "hydrogel" or "hydrogel material" refers to a crosslinked polymeric material which has three-dimensional polymer networks (i.e., polymer matrix), is insoluble in water, and can hold at least 10 percent by weight of water in its polymer matrix when it is fully hydrated.

A "silicone hydrogel" refers to a silicone-containing hydrogel obtained by copolymerization of a polymerizable composition comprising at least one silicone-containing monomer or at least one silicone-containing macromer or at least one crosslinkable silicone-containing prepolymer.

As used in this application, the term "non-silicone hydrogel" refers to a hydrogel that is theoretically free of silicon.

"Hydrophilic," as used herein, describes a material or portion thereof that will more readily associate with water than with lipids.

"Surface hydrophilicity," as used herein, describes a surface property that represents the extent to which a surface interacts with water, as measured by water-break-up-time (WBUT). The higher the value of WBUT is, the higher the surface hydrophilicity is.

In accordance with the invention, the "surface lubricity" or "lubricity" of a contact lens (or a medical device) is measured by a friction rating which is a number from 0 to 4. The higher the value of friction rating is, the lower the surface lubricity is.

A "vinylic monomer" refers to a compound that has one sole ethylenically unsaturated group, is soluble in a solvent, and can be polymerized actinically or thermally.

The term "soluble", in reference to a compound or material in a solvent, means that the compound or material can be dissolved in the solvent to give a solution with a concentration of at least about 0.1% by weight at room temperature (i.e., a temperature of about 22° C. to about 28° C.).

The term "insoluble", in reference to a compound or material in a solvent, means that the compound or material can be dissolved in the solvent to give a solution with a concentration of less than 0.005% by weight at room temperature (as defined above).

As used in this application, the term "ethylenically unsaturated group" is employed herein in a broad sense and is intended to encompass any groups containing at least one >C=C<group. Exemplary ethylenically unsaturated groups include without limitation (meth)acryloyl

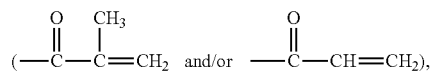

allyl, vinyl, styrenyl, or other C=C containing groups.

The term "(meth)acrylamide" refers to methacrylamide and/or acrylamide.

The term "(meth)acrylate" refers to methacrylate and/or acrylate.

As used herein, "actinically" in reference to curing, crosslinking or polymerizing of a polymerizable composition, a prepolymer or a material means that the curing (e.g., crosslinked and/or polymerized) is performed by actinic irradiation, such as, for example, UV/visible irradiation, ionizing radiation (e.g. gamma ray or X-ray irradiation), microwave irradiation, and the like. Thermal curing or actinic curing methods are well-known to a person skilled in the art.

A "hydrophilic vinylic monomer", as used herein, refers to a vinylic monomer which as a homopolymer typically yields a polymer that is water-soluble or can absorb at least 10 percent by weight of water.

A "hydrophobic vinylic monomer", as used herein, refers to a vinylic monomer which as a homopolymer typically yields a polymer that is insoluble in water and can absorb less than 10 percent by weight of water.

A "macromer" or "prepolymer" refers to a compound or polymer that contains ethylenically unsaturated groups and has an average molecular weight of greater than 700 Daltons.

As used in this application, the term "vinylic crosslinker" refers to a compound having at least two ethylenically unsaturated groups. A "vinylic crosslinking agent" refers to a vinylic crosslinker having a molecular weight of 700 Daltons or less.

As used in this application, the term "polymer" means a material formed by polymerizing/crosslinking one or more monomers or macromers or prepolymers or combinations thereof.

As used in this application, the term "molecular weight" of a polymeric material (including monomeric or macromeric materials) refers to the weight-average molecular weight unless otherwise specifically noted or unless testing conditions indicate otherwise.

The term "fluid" as used herein indicates that a material is capable of flowing like a liquid.

The term "alkyl" refers to a monovalent radical obtained by removing a hydrogen atom from a linear or branched alkane compound. An alkyl group (radical) forms one bond with one other group in an organic compound.

The term "alkylene divalent group" or "alkylene diradical" or "alkyl diradical" interchangeably refers to a divalent radical obtained by removing one hydrogen atom from an alkyl. An alkylene divalent group forms two bonds with other groups in an organic compound.

The term "alkyl triradical" refers to a trivalent radical obtained by removing two hydrogen atoms from an alkyl. An alkyl triradical forms three bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

In this application, the term "substituted" in reference to an alkyl diradical or an alkyl radical means that the alkyl diradical or the alkyl radical comprises at least one substituent which replaces one hydrogen atom of the alkyl diradical or the alkyl radical and is selected from the group consisting of hydroxy (—OH), carboxy (—COOH), —NH$_2$, sulfhydryl (—SH), $C_1$-$C_4$ alkyl, $C_1$-$C_4$ alkoxy, $C_1$-$C_4$ alkylthio (alkyl sulfide), $C_1$-$C_4$ acylamino, $C_1$-$C_4$ alkylamino, di-$C_1$-$C_4$ alkylamino, halogen atom (Br or Cl), and combinations thereof.

In this application, an "oxazoline" refers to a compound of

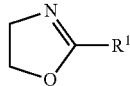

in which: $R^1$ is hydrogen, methyl, ethyl, N-pyrrolidonylmethyl, N-pyrrolidonylethyl, N-pyrrolidonylpropyl, or a monovalent radical of -alk-$(OC_2H_4)_{m3}$—OR" in which alk is $C_1$-$C_4$ alkyl diradical; R" is $C_1$-$C_4$ alkyl (preferably methyl); and m3 is an integer from 1 to 10 (preferably 1 to 5).

In this application, the term "polyoxazoline" refers to a linear polymer having a formula of

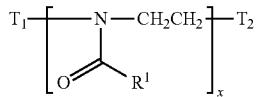

in which: T1 and T2 are two terminal groups; $R^1$ is hydrogen, methyl, ethyl, N-pyrrolidonylmethyl, N-pyrrolidonylethyl, N-pyrrolidonylpropyl, or a monovalent radical of -alk-$(OC_2H_4)_{m3}$—OR" in which alk is $C_1$-$C_4$ alkyl diradical; R" is $C_1$-$C_4$ alkyl (preferably methyl); m3 is an integer from 1 to 10 (preferably 1 to 5); x is an integer from 5 to 500. A polyoxazoline segment has a divalent polymer chain of a formula of

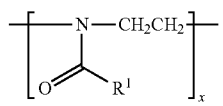

in which $R^1$ and x are as defined above.

In this application, the term "poly(2-oxazoline-co-ethyleneimine)" refers to a statistical copolymer having a formula of

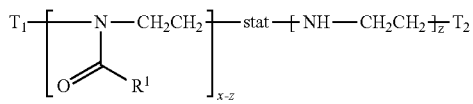

in which: T1 and T2 are terminal groups; $R^1$ is hydrogen, methyl, ethyl, N-pyrrolidonylmethyl, N-pyrrolidonylethyl, N-pyrrolidonylpropyl, or a monovalent radical of -alk-$(OC_2H_4)_{m3}$—OR" in which alk is $C_1$-$C_4$ alkyl diradical; R" is $C_1$-$C_4$ alkyl (preferably methyl); m3 is an integer from 1 to 10 (preferably 1 to 5); x is an integer from 5 to 500; z is an integer equal to or less than x. A poly(2-oxazoline-co-ethyleneimine) is obtained by hydrolyzing a polyoxazoline.

In this application, the term "poly(2-oxazoline-co-ethyleneimine)-epichlorohydrin" refers to a polymer obtained by reacting a poly(2-oxazoline-co-ethyleneimine) with epichlorohydrin to convert all or substantial percentage (90%) of the secondary amine groups of the poly(2-oxazoline-co-ethyleneimine) into azetidinium groups. Examples of poly (2-oxazoline-co-ethyleneimine)-epichlorohydrin are disclosed in U.S. pat. Appl. pub. No. 2016/0061995 A1 (herein incorporated by reference in its entirety).

An "epichlorohydrin-functionalized polyamine" or "epichlorohydrin-functionalized polyamidoamine" refers to a polymer obtained by reacting a polyamine or polyamidoamine with epichlorohydrin to convert all or a substantial percentage of the secondary amine groups of the polyamine or polyamidoamine into azetidinium groups.

The term "polyamidoamine-epichlorohydrin" refers to an epichlorohydrin-functionalized adipic acid-diethylenetriamine copolymer.

In this application the term "azetidinium" or "3-hydroxyazetidinium" refers to a positively-charged, divalent radical (or group or moiety) of

The term "thermally-crosslinkable" in reference to a polymeric material or a functional group means that the polymeric material or the functional group can undergo a crosslinking (or coupling) reaction with another material or functional group at a relatively-elevated temperature (from about 40° C. to about 140° C.), whereas the polymeric material or functional group cannot undergo the same crosslinking reaction (or coupling reaction) with another material or functional group at room temperature (i.e., from about 22° C. to about 28° C., preferably from about 24° C. to about 26° C., in particular at about 25° C.) to an extend detectable for a period of about one hour.

The term "azlactone" refers to a mono-valent radical of formula

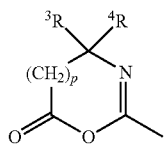

in which p is 0 or 1; $^3R$ and $^4R$ independently of each other is $C_1$-$C_8$ alkyl (preferably methyl).

As used in this application, the term "phosphorylcholine" refers to a monovalent zwitterionic group of

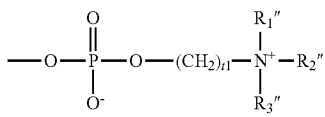

in which t1 is an integer of 1 to 5 and $R_1''$, $R_2''$ and $R_3''$ independently of one another are $C_1$-$C_8$ alkyl or $C_1$-$C_8$ hydroxyalkyl.

As used in this application, the term "reactive vinylic monomer" refers to any vinylic monomer having at least one reactive functional group selected from the group consisting of carboxyl group, primary amino group, and secondary amino group.

As used in this application, the term "non-reactive vinylic monomer" refers to any vinylic monomer (either hydrophilic or hydrophobic vinylic monomer) free of carboxyl group, primary amino group, secondary amino group, epoxide group, isocyanate group, azlactone group, or aziridine group.

A free radical initiator can be either a photoinitiator or a thermal initiator. A "photoinitiator" refers to a chemical that initiates free radical crosslinking/polymerizing reaction by the use of light. A "thermal initiator" refers to a chemical that initiates radical crosslinking/polymerizing reaction by the use of heat energy.

A "spatial limitation of actinic radiation" refers to an act or process in which energy radiation in the form of rays is directed by, for example, a mask or screen or combinations thereof, to impinge, in a spatially restricted manner, onto an area having a well-defined peripheral boundary. A spatial limitation of UV radiation is obtained by using a mask or screen having a radiation (e.g., UV) permeable region, a radiation (e.g., UV) impermeable region surrounding the radiation-permeable region, and a projection contour which is the boundary between the radiation-impermeable and radiation-permeable regions, as schematically illustrated in the drawings of U.S. Pat. No. 6,800,225 (FIGS. 1-11), and U.S. Pat. No. 6,627,124 (FIGS. 1-9), U.S. Pat. No. 7,384,590 (FIGS. 1-6), and U.S. Pat. No. 7,387,759 (FIGS. 1-6), all of which are incorporated by reference in their entireties. The mask or screen allows to spatially projects a beam of radiation (e.g., UV radiation) having a cross-sectional profile defined by the projection contour of the mask or screen. The projected beam of radiation (e.g., UV radiation) limits radiation (e.g., UV radiation) impinging on a lens formulation located in the path of the projected beam from the first molding surface to the second molding surface of a mold. The resultant contact lens comprises an anterior surface defined by the first molding surface, an opposite posterior surface defined by the second molding surface, and a lens edge defined by the sectional profile of the projected UV beam (i.e., a spatial limitation of radiation). The radiation used for the crosslinking is radiation energy, especially UV radiation, gamma radiation, electron radiation or thermal radiation, the radiation energy preferably being in the form of a substantially parallel beam in order on the one hand to achieve good restriction and on the other hand efficient use of the energy.

A "water contact angle" refers to an average water contact angle (i.e., contact angles measured by Sessile Drop method) at the room temperature, which is obtained by averaging measurements of contact angles with at least 3 individual contact lenses (or medical devices).

The term "intactness" in reference to a coating on a silicone contact lens (or a medical device) is intended to describe the extent to which the contact lens (or medical device) can be stained by Sudan Black in a Sudan Black staining test described in Example 1. Good intactness of the coating on a silicone contact lens (or a medical device) means that there is practically no Sudan Black staining of the contact lens (or the medical device).

The term "durability" in reference to a coating on a silicone contact lens (or medical device) is intended to describe that the coating on the silicone contact lens (or medical device) can survive a digital rubbing test.

As used herein, "surviving a digital rubbing test" or "surviving a durability test" in reference to a coating on a contact lens (or medical device) means that after digitally rubbing the lens (or medical device) according to a procedure described below, the digitally rubbed lens (or medical device) still has a WBUT of about 5 seconds or longer (preferably about 7.5 seconds or longer, more preferably about 10 seconds or longer, even more preferably about 12.5 seconds or longer) and/or a friction rating of about 2 or lower (more preferably about 1 or smaller).

The term "one cycle of digital rubbing test" means that contact lenses (or medical devices) with a coating thereon are digitally rubbed (wearing disposable powder-free latex gloves) with RENU® multi-purpose lens care solution (or another multi-purpose lens care solution) for 20 seconds and then rinsed with saline. The above procedure can be repeated for a given times, e.g., from 2 to 30 times and number of repetitions of digital rubbing tests is the number of cycles of digital rubbing tests.

The intrinsic "oxygen permeability", Dk, of a material is the rate at which oxygen will pass through a material. As used in this application, the term "oxygen permeability (Dk)" in reference to a hydrogel (silicone or non-silicone) or a contact lens means a measured oxygen permeability (Dk) which is corrected for the surface resistance to oxygen flux caused by the boundary layer effect according to the procedures described in Example 1 of 2012/0026457 A1 (herein incorporated by reference in its entirety). Oxygen permeability is conventionally expressed in units of barrers, where "barrer" is defined as $[(cm^3 \text{ oxygen})(mm)/(cm^2)(sec)(mm Hg)] \times 10^{-10}$.

The "oxygen transmissibility", Dk/t, of a lens or material is the rate at which oxygen will pass through a specific lens or material with an average thickness of t [in units of mm] over the area being measured. Oxygen transmissibility is conventionally expressed in units of barrers/mm, where "barrers/mm" is defined as $[(cm^3 \text{ oxygen})/(cm^2)(sec)(mm Hg)] \times 10^{-9}$.

"Ophthalmically compatible", as used herein, refers to a material or surface of a material which may be in intimate contact with the ocular environment for an extended period of time without significantly damaging the ocular environment and without significant user discomfort.

The term "ophthalmically safe" with respect to a packaging solution for sterilizing and storing contact lenses is meant that a contact lens stored in the solution is safe for direct placement on the eye without rinsing after autoclave and that the solution is safe and sufficiently comfortable for daily contact with the eye via a contact lens. An ophthalmically-safe packaging solution after autoclave has a tonicity and a pH that are compatible with the eye and is substantially free of ocularly irritating or ocularly cytotoxic materials according to international ISO standards and U.S. FDA regulations.

The term "modulus" or "elastic modulus" in reference to a contact lens or a material means the tensile modulus or Young's modulus which is a measure of the stiffness of a contact lens or a material. The modulus can be measured using a method in accordance with ANSI Z80.20 standard. A person skilled in the art knows well how to determine the elastic modulus of a silicone hydrogel material or a contact lens. For example, all commercial contact lenses have reported values of elastic modulus.

An "aqueous solution" or a "water-based solution" interchangeably refers to a solution which is a homogeneous mixture consisting of a water-based solvent and one or more solutes dissolved in the water-based solvent. A "water-based solvent" is intended to describe a solvent system which consists of at least 50% (preferably at least about 60%, more preferably at least about 80%, even more preferably at least about 90%, in particular at least about 95%) by weight of water and at most 50% (preferably about 40% or less, more preferably about 20% or less, even more preferably about 10% or less, in particular about 5% or less) by weight of one or more organic solvents relative to the weight of the solvent system. A water-based coating solution refers to a water-based solution containing at least one polymeric coating material as a solute in the solution.

An "organic-based solution" refers to a solution which is a homogeneous mixture consisting of an organic-based solvent and one or more solutes dissolved in the organic based solvent. An "organic-based solvent" is intended to describe a solvent system which consists of one or more organic solvents and less than 49%, preferably about 40% or less, more preferably about 20% or less, even more preferably about 10% or less, in particular about 5% or less by weight of water relative to the weight of the solvent system. An organic-based coating solution refers to an organic-based solution containing at least one polymeric coating material as a solute in the solution.

In this application, the term "quenching" in reference to a plasma-treated silicone contact lens (or medical device) refers to a process in which the plasma-treated silicone contact lens (or medical device) still in a dry state is in contact with (e.g., being immersed in or sprayed with) any liquid at the first time within about 40 minutes or less immediately after the plasma treatment.

In this application, the term "thermodynamically-stable" in reference with a hydrogel coating on a medical device (especially a silicone contact lens) means that the hydrogel coating on that medical device (especially silicone contact lens) is still hydrophilic and/or lubricious even after the silicone contact lens with the hydrogel coating thereon has been stored in the air in its dry state at room temperature for at least about two days (preferably at least about 7 days, more preferably at least about 14 days, even more preferably at least about 30 days, most preferably at least about 60 days) and then rehydrated.

In this application, the term "hydrophilic" in reference to a hydrogel coating refers to a hydrogel coating which is formed on a medical device (especially a silicone contact lens) and provides that medical device (especially that silicone contact lens) with a surface hydrophicity as measured by a WBUT of at least about 5 seconds. WBUT can be determined according to the procedures described in Example 1.

In this application, the term "lubricious" in reference to a hydrogel coating on a medical device (especially a silicone contact lens) means that that medical device (especially silicone contact lens) has a friction rating of about 3 or lower as determined according to the procedures described in Example 1.

The invention is generally related to medical devices (especially ophthalmic devices) which have a core material made of a crosslinked silicone material and a thermodynamically-stable hydrophilic and optionally (but preferably) lubricious hydrogel coating thereon and to a method for producing such medical devices (especially ophthalmic devices). It is well known to a person skilled in the art that although the surface of a silicone substrate (including a silicone contact lens) can be rendered wettable or hydrophilic by a known surface treatment, its wettability or surface hydrophilicity can deteriorate significantly over time when it is stored in the air in its dry state. This is due to the fact that, thermodynamically, silicone will migrate to the surface of the silicone substrate in the air to minimize the surface energy, because silicone is hydrophobic and has very low surface energy. In order for a medical device (especially an ophthalmic device) to be a commercial viable product, it is believed by the inventors that any hydrophilic and optionally (but preferably) lubricious hydrogel coating on that medical device should be thermodynamically stable for at least 24 hours when it is stored in the air in its dry state.

Otherwise, the surface hydrophilicity and lubricity of that coating can deteriorate significantly over time during wearing, cleaning, handing and storing due to intentional or unintentional exposure to the air for an extended time period or for an accumulated long time period. The present invention is largely based on the discovery that a thermodynamically-stable hydrophilic and lubricious hydrogel coating can be formed on a silicone contact lens (or any silicone substrate) according to a surface treatment of the invention that comprises an orderly sequence of at least three steps: a plasma treatment, contacting with a reactive hydrophilic polymer, and thermally-induced crosslinking of a thermally-crosslinkable hydrophilic polymeric material. It is understood that the last step can be replaced with crosslinking or grafting of any crosslinkable hydrophilic polymeric material according to any reaction mechanism.

In one aspect, the invention provides a method for producing a medical device (preferably an ophthalmic device, more preferably a soft contact lnes) which includes a silicone substrate and a hydrogel coating thereon, the method of invention comprising the steps of:

(1) obtaining a silicone substrate in a dry state, wherein the silicone substrate is made of a crosslinked silicone material;

(2) subjecting the silicone substrate in the dry state to a surface treatment to form a base coating comprising a prime plasma layer and a reactive polymer layer, wherein the surface treatment comprises the sub-steps of (a) plasma-treating the surface of the silicone substrate in the dry state with a plasma to form the prime plasma layer on the silicone substrate, wherein the prime plasma layer has a thickness of less than about 40 nm (preferably from about 1 nm to about 35 nm, more preferably from about 2 nm to about 30 nm), wherein the plasma is generated in a plasma gas (i.e., an atmosphere) composed of air, $CO_2$, or a mixture of a $C_1$-$C_6$ hydrocarbon and a secondary gas selected from the group consisting of air, $CO_2$, $N_2$, and combinations thereof (preferably air, $CO_2$ or a mixture of a $C_1$-$C_4$ hydrocarbon and a secondary gas selected from the group consisting of air, $CO_2$, $N_2$, and combinations thereof, more preferably $CO_2$ or a mixture of methane and a secondary gas selected from the group consisting of air, $CO_2$, $N_2$, and combinations thereof, even more preferably $CO_2$ or a mixture of methane and air, or a mixture of methane and $CO_2$), and (b) contacting the plasma-treated silicone substrate with a first aqueous solution including a reactive hydrophilic polymer to form a reactive polymer layer, wherein the reactive hydrophilic polymer has multiple reactive functional groups selected from the group consisting of carboxyl groups, primary amine groups, secondary amine groups, and combinations thereof (preferably carboxyl groups); and (3) heating the silicone substrate with the base coating thereon obtained in step (2), in a second aqueous solution which comprises a water-soluble and thermally-crosslinkable hydrophilic polymeric material having azetidinium groups and optionally (but preferably) amino or carboxyl groups, at a temperature of from about 60° C. to about 140° C. for a time period sufficient long to crosslink the water-soluble thermally-crosslinkable hydrophilic polymeric material and the base coating so as to obtain the medical device which comprises the silicone substrate and a hydrogel coating thereon, wherein the medical device (preferably the soft contact lens) in fully hydrated state has a WBUT of at least about 5 seconds and a friction rating of about 3 or lower (preferably about 2.5 or lower, more preferably about 2 or lower, even more preferably about 1.5 or lower, most preferably about 1 or lower), wherein the hydrogel coating is thermodynamically stable as characterized by having a dry-storage-induced reduction in WBUT after i days of dry storage, designated as $\Delta WBUT_{DS}(i)$, of about 45% or less (preferably about 35% or less, more preferably about 25% or less, even more preferably about 15% or less) and optionally a dry-storage-induced increase in friction rating after i days of dry storage, $\Delta FR_{DS}(i)$, of about 60% or less (preferably about 50% or less, more preferably about 40% or less, even more preferably about 30% or less), wherein $$\Delta WBUT_{DS}(i) = \frac{WBUT_{DS@0} - WBUT_{DS@i}}{WBUT_{DS@0}} \times 100\% \text{ and}$$

$$\Delta FR_{DS}(i) = \frac{FR_{DS@i} - FR_{DS@0}}{4} \times 100\%$$

in which $WBUT_{DS@0}$ and $FR_{DS@0}$ are the WBUT and the friction rating of the medical device in fully-hydrated state at day zero of dry storage and are determined before the medical device is dehydrated and stored in air at room temperature, and $WBUT_{DS@i}$ and $FR_{DS@i}$ are the WBUT and the friction rating of the medical device in fully hydrated state at/days of dry storage and are determined after the medical device has been fully dehydrated and stored in air at room temperature for at least i days and then has been fully rehydrated before determining the WBUT and the friction rating, wherein i is an integer of 2 or larger (preferably 7 or larger, more preferably 14 or larger, even more preferably 30 or larger, most preferably 60 or larger).

Preferably, the hydrogel coating is durable as characterized by having a digital-rubbing-induced reduction in WBUT after j cycles of digital rubbing tests, $\Delta WBUT_{DR}(j)$, of about 45% or less (preferably about 35% or less, more preferably about 25% or less, even more preferably about 15% or less) and/or a digital-rubbing-induced increase in friction rating after j cycles of digital rubbing tests, $\Delta FR_{DR}(J)$, of about 60% or less (preferably about 50% or less, more preferably about 40% or less, even more preferably about 30% or less), wherein $$\Delta WBUT_{DR}(j) = \frac{WBUT_{0DR} - WBUT_{jDR}}{WBUT_{0DR}} \times 100\% \text{ and}$$

$$\Delta FR_{DR}(j) = \frac{FR_{jDR} - FR_{0DR}}{4} \times 100\%$$

in which $WBUT_{0DR}$ and $FR_{0DR}$ are the WBUT and the friction rating of the medical device which is in fully-hydrated state and is subjected to zero digital rubbing test, and $WBUT_{jDR}$ and $FR_{jDR}$ are the WBUT and the friction rating of the medical device which is in fully hydrated state and has been subjected to at least j cycles of digital rubbing tests, wherein j is an integer of 2 (preferably 7, more preferably 14, even more preferably 30).

In accordance with the invention, a silicone substrate can be any article having any shape, preferably a medical device, more preferably an ophthalmic device, even more preferably a silicone contact lens, so long as it is made of a crosslinked silicone material.

Useful crosslinked silicone materials include, without limitation, crosslinked polysiloxanes obtained by crosslinking silicone composition according to any know method, silicone elastomers, silicone rubbers, and the likes. Silicone substrates including silicone contact lenses can be prepared by any kind of conventional techniques (for example, the lathe cut manufacturing method, the spin cast manufacturing method, the cast molding manufacturing method, etc.) well-known to a person skilled in the art.

In a preferred embodiment, a crosslinked silicone material can be obtained according to hydrosilylation reaction from a silicone composition comprising: (1) at least one alkenyl-containing organopolysiloxane having at least two alkenyl groups (e.g., vinyl group, allyl group, 1-propenyl group, and isopropenyl group, and preferably vinyl group) each bonded to a silicon atom; (2) at least one hydride-containing organopolysiloxane having at least two hydrogen atoms each bonded to a silicon atom; and (3) a hydrosilylation catalyst.

The alkenyl-containing organopolysiloxane may be linear, branched, or cyclic. Also, it may be a homopolymer or a copolymer. Its polymerization degree may be an oligomer to a high polymer of 100-10000 units. At least two alkenyl groups must exist in one molecule of the alkenyl-containing organopolysiloxane. Its location may be anywhere in the alkenyl-containing organopolysiloxane. Examples of preferred alkenyl-containing organopolysiloxanes include, without limitation, poly(dihydrocarbylsiloxane-co-alkenyl-hydrocarbylsiloxane) in which the hydrocarbyl radicals are monovalent hydrocarbon radicals including without limitation, $C_1$-$C_{10}$ radicals, aryl radicals including without limitation phenyl, tolyl, xylyl, and biphenyl, haloaryls, including, without limitation chlorophenyl and cycloalkyl radicals, and the like, and the alkenyl radicals vinyl group, allyl group, 1-propenyl group, and isopropenyl group, and preferably vinyl group.

The hydride-containing organopolysiloxane may be linear, branched, or cyclic. Also, it may be a homopolymer or a copolymer. Its polymerization degree may be an oligomer to a high polymer of 100-10000 units. At least two hydride groups must exist in one molecule of the hydride-containing organopolysiloxane. Its location may be anywhere in the hydride-containing organopolysiloxane. Examples of preferred hydride-containing organicpolysiloxanes include, without limitation, poly(dihydrocarbylsiloxane-co-hydrocarbylhydrogensiloxane) in which the hydrocarbyl radicals are monovalent hydrocarbon radicals including without limitation, $C_1$-$C_{10}$ radicals, aryl radicals including without limitation phenyl, tolyl, xylyl, and biphenyl, haloaryls, including, without limitation chlorophenyl and cycloalkyl radicals, and the like.

The hydride-containing organopolysiloxane is present in the silicone composition in such an amount that the number of the hydrogen atoms bonded to the silicon atom in the hydride-containing organopolysiloxane is in the range of 0.8 to 10, preferably 1 to 5 for one alkenyl group bonded to the silicon atom in the alkenyl-containing organopolysiloxan. If the amount of the hydride-containing organopolysiloxane is such an amount that the number of the hydrogen atoms bonded to the silicon atom in the hydride-containing organopolysiloxane is less than 0.8 for one alkenyl group bonded to the silicon atom in the alkenyl-containing organopolysiloxan, the resulting composition will not sufficiently be cured. Also, If the blended amount of the hydride-containing organopolysiloxane is such an amount that the number of the hydrogen atoms bonded to the silicon atom in the hydride-containing organopolysiloxane is more than 10 for one alkenyl group bonded to the silicon atom in the alkenyl-containing organopolysiloxan, the resulting silicone rubber will have extremely poor rubber elasticity.

Any hydrosilylation catalysts can be used in the invention so long as they can accelerate the addition reaction of the alkenyl group in the alkenyl-containing organopolysiloxan with the hydrogen atom bonded to the silicon atom in the hydride-containing organopolysiloxan. The specific examples of these include platinum group metals and their compounds including platinum, palladium, rhodium, and the like; an alcohol-modified chloroplatinic acid; a coordination compound of chloroplatinic acid with an olefin, vinyl siloxane or an acetylene compound; tetrakis(triphenylphosphine)palladium; and chlorotris(triphenylphosphine)rhodium; and the like, with platinum group compound being especially preferred. Also, a photoactivable platinum complex catalyst having a β-diketone platinum complex or a cyclic diene compound as the ligand may be used. These platinum complexes are disclosed in, for example, U.S. Pat. Nos. 6,376,569, 4,916,169, 6,046,250, 5,145,886, 6,150,546, 4,530,879, and 4,510,094 (herein incorporated in references in their entireties).

The hydrosilylation catalyst may be present in any effective amount as the catalyst, and preferably be in the range of 1 to 500 ppm, more preferably 10 to 100 ppm based on the mass converted into the catalyst metal elements for the total amount of the alkenyl-containing organopolysiloxane and hydride-containing organopolysiloxane. If the amount is within the range, the reaction velocity of the addition reaction will be appropriate and the cured material will have good heat resistance.

It is understood that additives, such as methylvinylcyclotetrasiloxane, an acetylene alcohol or a maleic acid derivative, may also be added in order to provide good storage stability at room temperature and suitable pot life.

In addition, curing the silicone composition by the hydrosilyation reaction may be conducted by heating the silicone composition at a temperature of 60° C. to 250° C. for about one minute to five hours. Preferably, a silicone composition is cured in molds for making contact lenses. Examples of molds for making contact lenses are described below.

Also, curing the silicone composition by the hydrosilyation reaction using a photoactivable platinum complex catalyst may preferably be conducted by exposing the silicone composition to a light having a wavelength of about 200 to about 800 nm. The curing may be conducted by irradiating the light to the silicone composition for 10 seconds to thirty minutes. The examples of the suitable light sources include a tungsten halogen lamp, a xenon arc lamp, a mercury-arc lamp, a UV-LED, and the like.

In another preferred embodiment, a crosslinked silicone material can be obtained according to free radical growth polymerization reaction from a polymerizable silicone composition comprising at least one organopolysiloxane vinylic crosslinker having at least two (meth)acryloyl groups and a free radical initiator.

The organopolysiloxane vinylic crosslinker may be linear, branched, or cyclic. Also, it may be a homopolymer or a copolymer. Its polymerization degree may be an oligomer to a high polymer of 100-10000 units. At least two (meth)acryloyl groups must exist in one molecule of the alkenyl-containing organopolysiloxane, and they can terminal groups or pendant groups.

Any suitable organopolysiloxane vinylic crosslinkers can be used in the invention. Examples of preferred organopolysiloxane vinylic crosslinkers are dimethacrylated or diacrylated polydimethylsiloxanes of various molecular weight; di-vinyl carbonate-terminated polydimethylsiloxanes; di-vinyl carbamate-terminated polydimethylsiloxane;

di-methacrylamide-terminated polydimethylsiloxanes; di-acrylamide-terminated polydimethylsiloxanes; bis-3-methacryloxy-2-hydroxypropyloxypropyl polydimethylsiloxane; N,N,N',N'-tetrakis(3-methacryloxy-2-hydroxypropyl)-alpha,omega-bis-3-aminopropyl-polydimethylsiloxane; polysiloxanylalkyl (meth)acrylic monomers; siloxane-containing macromer selected from the group consisting of Macromer A, Macromer B, Macromer C, and Macromer D described in U.S. Pat. No. 5,760,100 (herein incorporated by reference in its entirety); chain-extended polysiloxane vinylic crosslinkers disclosed in US201008843A1 and US20120088844A1 (herein incorporated by references in their entireties); the reaction products of glycidyl methacrylate with amino-functional polydimethylsiloxanes; polysiloxane-containing macromers disclosed in U.S. Pat. Nos. 4,136,250, 4,153,641, 4,182,822, 4,189,546, 4,343,927, 4,254,248, 4,355,147, 4,276,402, 4,327,203, 4,341,889, 4,486,577, 4,543,398, 4,605,712, 4,661,575, 4,684,538, 4,703,097, 4,833,218, 4,837,289, 4,954,586, 4,954,587, 5,010,141, 5,034,461, 5,070,170, 5,079,319, 5,039,761, 5,346,946, 5,358,995, 5,387,632, 5,416,132, 5,451,617, 5,486,579, 5,962,548, 5,981,675, 6,039,913, and 6,762,264 (here incorporated by reference in their entireties); polysiloxane-containing macromers disclosed in U.S. Pat. Nos. 4,259,467, 4,260,725, and 4,261,875 (herein incorporated by reference in their entireties).

Examples of suitable thermal initiators include, but are not limited to, 2,2'-azobis (2,4-dimethylpentanenitrile), 2,2'-azobis (2-methylpropanenitrile), 2,2'-azobis (2-methylbutanenitrile), peroxides such as benzoyl peroxide, and the like. Preferably, the thermal initiator is 2,2'-azobis(isobutyronitrile) (AIBN).

Suitable photoinitiators are benzoin methyl ether, diethoxyacetophenone, a benzoylphosphine oxide, 1-hydroxycyclohexyl phenyl ketone and Darocur and Irgacur types, preferably Darocur 1173® and Darocur 2959®, Germane-based Norrish Type I photoinitiators. Examples of benzoylphosphine initiators include 2,4,6-trimethylbenzoyl-diphenylophosphine oxide; bis-(2,6-dichlorobenzoyl)-4-N-propylphenylphosphine oxide; and bis-(2,6-dichlorobenzoyl)-4-N-butylphenylphosphine oxide. Reactive photoinitiators which can be incorporated, for example, into a macromer or can be used as a special monomer are also suitable. Examples of reactive photoinitiators are those disclosed in EP 632 329, herein incorporated by reference in its entirety. The polymerization can then be triggered off by actinic radiation, for example light, in particular UV light of a suitable wavelength. The spectral requirements can be controlled accordingly, if appropriate, by addition of suitable photosensitizers.

A polymerizable silicone composition can further comprise one or more components selected from the group consisting of a silicone-containing vinylic monomer, a hydrophobic vinylic monomer, a hydrophilic vinylic monomer, a vinylic crosslinking agent, a UV-absorbing vinylic monomer, and combinations thereof. Preferred examples of a silicone-containing vinylic monomer, a hydrophobic vinylic monomer, a hydrophilic vinylic monomer, a vinylic crosslinking agent, and a UV-absorbing vinylic monomer are described below.

Any suitable silicone-containing vinylic monomers can be used in the invention. Examples of preferred silicone-containing vinylic monomers include without limitation N-[tris(trimethylsiloxy)silylpropyl]-(meth)acrylamide, N-[tris(dimethylpropylsiloxy)-silylpropyl]-(meth)acrylamide, N-[tris(dimethylphenylsiloxy)silylpropyl] (meth)acrylamide, N-[tris(dimethylethylsiloxy)silylpropyl] (meth)acrylamide, N-(2-hydroxy-3-(3-(bis(trimethylsilyloxy)methylsilyl)propyloxy)propyl)-2-methyl acrylamide; N-(2-hydroxy-3-(3-(bis(trimethylsilyloxy) methylsilyl) propyloxy)propyl) acrylamide; N,N-bis[2-hydroxy-3-(3-(bis(trimethylsilyloxy)methylsilyl)oxy)propyl]-2-methyl acrylamide; N,N-bis[2-hydroxy-3-(3-(bis(trimethylsilyloxy)methylsilyl)propyloxy)propyl] acrylamide; N-(2-hydroxy-3-(3-(tris(trimethylsilyloxy)silyl)propyloxy)propyl)-2-methyl acrylamide; N-(2-hydroxy-3-(3-(tris(trimethylsilyloxy)silyl) propyloxy)propyl)acrylamide; N,N-bis[2-hydroxy-3-(3-(tris(trimethylsilyloxy)silyl)propyloxy)propyl]-2-methyl acrylamide; N,N-bis[2-hydroxy-3-(3-(tris(trimethylsilyloxy)silyl)propyloxy)propyl]acrylamide; N-[2-hydroxy-3-(3-(t-butyldimethylsilyl)propyloxy)propyl]-2-methyl acrylamide; N-[2-hydroxy-3-(3-(t-butyldimethylsilyl) propyloxy)propyl]acrylamide; N, N-bis[2-hydroxy-3-(3-(t-butyldimethylsilyl)propyloxy)propyl]-2-methyl acrylamide; N,N-bis[2-hydroxy-3-(3-(t-butyldimethylsilyl) propyloxy)propyl]acrylamide; 3-methacryloxy propylpentamethyldisiloxane, trimethylsilylmethyl(meth)acrylate, pentamethyldisiloxyethyl (meth)acrylate, tris(trimethylsiloxy)silylpropyl (meth)acrylate, methyldi(trimethylsiloxy)methyldisiloxanylpropyl (meth)acrylate, tert-butyltetramethyldisiloxanylethyl (meth) acrylate, (3-methacryloxy-2-hydroxypropyloxy)propylbis (trimethylsiloxy)methylsilane), (3-methacryloxy-2-hydroxypropyloxy) propyltris(trimethylsiloxy)silane, 3-methacryloxy-2-(2-hydroxyethoxy)-propyloxy)propylbis(trimethylsiloxy)methylsilane, N-2-methacryloxyethyl-O-(methyl-bis-trimethylsiloxy-3-propyl)silyl carbamate, 3-(trimethylsilyl)propylvinyl carbonate, 3-(vinyloxycarbonylthio) propyl-tris(trimethyl-siloxy)silane, 3-[tris(trimethylsiloxy)silyl]propylvinyl carbamate, 3-[tris(trimethylsiloxy)silyl] propyl allyl carbamate, 3-[tris(trimethylsiloxy) silyl]propyl vinyl carbonate, t-butyldimethyl-siloxyethyl vinyl carbonate; trimethylsilylethyl vinyl carbonate, and trimethylsilylmethyl vinyl carbonate); monomethacrylated or monoacrylated polydimethylsiloxanes of various molecular weight (e.g., mono-3-methacryloxypropyl terminated, mono-butyl terminated polydimethylsiloxane or mono-(3-methacryloxy-2-hydroxypropyloxy)propyl terminated, mono-butyl terminated polydimethylsiloxane); mono-vinyl carbonate-terminated polydimethylsiloxanes; mono-vinyl carbamate-terminated polydimethylsiloxane; mono-methacrylamide-terminated polydimethylsiloxanes; mono-acrylamide-terminated polydimethylsiloxanes; carbosiloxane vinylic monomers disclosed in U.S. Pat. Nos. 7,915,323 and 8,420,711, in US Patent Applicaton Publication Nos. 2012/244088 and 2012/245249 (herein incorporated by references in their entireties); combinations thereof.

Examples of preferred hydrophobic vinylic monomers include methylacrylate, ethyl-acrylate, propylacrylate, isopropylacrylate, cyclohexylacrylate, 2-ethylhexylacrylate, methylmethacrylate, ethylmethacrylate, propylmethacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonyl-aminoethyl-methacrylate, isobornyl methacrylate, trifluoroethyl methacrylate, hexafluoro-isopropyl methacrylate, hexafluorobutyl methacrylate.

Any suitable hydrophilic vinylic monomers can be used in the invention. Examples of preferred vinylic monomers include without limitation N,N-dimethylacrylamide (DMA), N,N-dimethylmethacrylamide (DMMA), 2-acrylamidoglycolic acid, N-hydroxypropylacrylamide, N-hydroxyethyl acrylamide, N-[tris(hydroxymethyl)methyl]-acrylamide, N-vinylpyrrolidone, N-vinyl formamide, N-vinyl acetamide, N-vinyl isopropylamide, N-vinyl-N-methyl acetamide, N-methyl-3-methylene-2-pyrrolidone, 1-methyl-5-methylene-2-pyrrolidone, 5-methyl-3-methylene-2-pyrrolidone, 2-hydroxyethylmethacrylate (HEMA), 2-hydroxyethyl acrylate (HEA), hydroxypropyl acrylate, hydroxypropyl methacrylate (HPMA), trimethylammonium 2-hydroxy propylmethacrylate hydrochloride, aminopropyl methacrylate hydrochloride, dimethylaminoethyl methacrylate (DMAEMA), glycerol methacrylate (GMA), a $C_1$-$C_4$-alkoxy polyethylene glycol (meth)acrylate having a weight average molecular weight of up to 1500, (meth)acrylic acid, and mixtures thereof. In accordance with the invention, a polymerizable silicone composition comprises less than 5% (preferably less than 4%, more preferably about 3% or less, even more preferably about 2% or less) by weight of one or more hydrophilic vinylic monomers listed above.

Examples of preferred vinylic cross-linking agents include without limitation tetraethyleneglycol diacrylate, triethyleneglycol diacrylate, diethyleneglycol diacrylate, ethyleneglycol diacrylate, tetraethyleneglycol dimethacrylate, triethyleneglycol dimethacrylate, diethyleneglycol dimethacrylate, ethyleneglycol dimethacrylate, tetraethyleneglycol divinyl ether, triethyleneglycol divinyl ether, diethyleneglycol divinyl ether, ethyleneglycol divinyl ether, trimethylopropane trimethacrylate, pentaerythritol tetramethacrylate, bisphenol A dimethacrylate, vinyl methacrylate, ethylenediamine dimethyacrylamide, ethylenediamine diacrylamide, glycerol dimethacrylate, triallyl isocyanurate, triallyl cyanurate, allylmethacrylate, allylacrylate, N-allyl-methacrylamide, N-allyl-acrylamide, 1,3-bis(methacrylamidopropyl)-1,1,3,3-tetrakis-(trimethylsiloxy)disiloxane, N,N'-methylenebisacrylamide, N,N'-methylenebismethacrylamide, N,N'-ethylenebisacrylamide, N,N'-ethylenebismethacrylamide, 1,3-bis(N-methacrylamidopropyl)-1,1,3,3-tetrakis-(trimethylsiloxy)disiloxane, 1,3-bis(methacrylamidobutyl)-1,1,3,3-tetrakis-(trimethylsiloxy)-disiloxane, 1,3-bis(acrylamidopropyl)-1,1,3,3-tetrakis(trimethylsiloxy)disiloxane, 1,3-bis(methacryloxyethylureidopropyl)-1,1,3,3-tetrakis(trimethylsiloxy)disiloxane, and combinations thereof. The amount of a cross-linking agent used is expressed in the weight content with respect to the total polymer and is preferably less than 2%, and more preferably from about 0.01% to about 1%.

Any suitable UV-absorbing vinylic monomers can be used in a polymerizable composition for preparing a polymer of the invention. Examples of preferred UV-absorbing and UV/HEVL-absorbing, benzotriazole-containing vinylic monomers include without limitation: 2-(2-hydroxy-5-vinylphenyl)-2H-benzotriazole, 2-(2-hydroxy-5-acrylyloxyphenyl)-2H-benzotriazole, 2-(2-hydroxy-3-methacrylamido methyl-5-tert octylphenyl) benzotriazole, 2-(2'-hydroxy-5'-methacrylamidophenyl)-5-chlorobenzotriazole, 2-(2'-hydroxy-5'-methacrylamidophenyl)-5-methoxybenzotriazole, 2-(2'-hydroxy-5'-methacryloxypropyl-3'-t-butyl-phenyl)-5-chlorobenzotriazole, 2-(2'-hydroxy-5'-methacryloxypropylphenyl) benzotriazole, 2-hydroxy-5-methoxy-3-(5-(trifluoromethyl)-2H-benzo[d][1,2,3]triazol-2-yl)benzyl methacrylate (WL-1), 2-hydroxy-5-methoxy-3-(5-methoxy-2H-benzo[d][1,2,3]triazol-2-yl)benzyl methacrylate (WL-5), 3-(5-fluoro-2H-benzo[d][1,2,3]triazol-2-yl)-2-hydroxy-5-methoxybenzyl methacrylate (WL-2), 3-(2H-benzo[d][1,2,3]triazol-2-yl)-2-hydroxy-5-methoxybenzyl methacrylate (WL-3), 3-(5-chloro-2H-benzo[d][1,2,3]triazol-2-yl)-2-hydroxy-5-methoxybenzyl methacrylate (WL-4), 2-hydroxy-5-methoxy-3-(5-methyl-2H-benzo[d][1,2,3]triazol-2-yl) benzyl methacrylate (WL-6), 2-hydroxy-5-methyl-3-(5-(trifluoromethyl)-2H-benzo[d][1,2,3]triazol-2-yl)benzyl methacrylate (WL-7), 4-allyl-2-(5-chloro-2H-benzo[d][1,2,3]triazol-2-yl)-6-methoxyphenol (WL-8), 2-{2'-Hydroxy-3'-tert-5'[3"-(4"-vinylbenzyloxy)propoxy]phenyl}-5-methoxy-2H-benzotriazole, phenol, 2-(5-chloro-2H-benzotriazol-2-yl)-6-(1,1-dimethylethyl)-4-ethenyl-(UVAM), 2-(2'-hydroxy-5'-methacryloxyethylphenyl) benzotriazole (2-Propenoic acid, 2-methyl-, 2-[3-(2H-benzotriazol-2-yl)-4-hydroxyphenyl]ethyl ester, Norbloc), 2-{2'-Hydroxy-3'-tert-butyl-5'-[3'-methacryloyloxypropoxy]phenyl}-5-methoxy-2H-benzotriazole (UV13), 2-[2'-Hydroxy-3'-tert-butyl-5'-(3'-acryloyloxypropoxy)phenyl]-5-trifluoromethyl-2H-benzotriazole ($CF_3$—UV13), 2-(2'-hydroxy-5-methacrylamidophenyl)-5-methoxybenzotriazole (UV6), 2-(3-allyl-2-hydroxy-5-methyl phenyl)-2H-benzotriazole (UV9), 2-(2-Hydroxy-3-methallyl-5-methylphenyl)-2H-benzotriazole (UV12), 2-3'-t-butyl-2'-hydroxy-5'-(3"-dimethylvinylsilylpropoxy)-2'-hydroxy-phenyl)-5-methoxybenzotriazole (UV15), 2-(2'-hydroxy-5'-methacryloylpropyl-3'-tert-butyl-phenyl)-5-methoxy-2H-benzotriazole (UV16), 2-(2'-hydroxy-5'-acryloylpropyl-3'-tert-butyl-phenyl)-5-methoxy-2H-benzotriazole (UV16A), 2-Methylacrylic acid 3-[3-tert-butyl-5-(5-chlorobenzotriazol-2-yl)-4-hydroxyphenyl]-propyl ester (16-100, CAS#96478-15-8), 2-(3-(tert-butyl)-4-hydroxy-5-(5-methoxy-2H-benzo[d][1,2,3]triazol-2-yl) phenoxy)ethyl methacrylate (16-102); Phenol, 2-(5-chloro-2H-benzotriazol-2-yl)-6-methoxy-4-(2-propen-1-yl) (CAS#1260141-20-5); 2-[2-Hydroxy-5-[3-(methacryloyloxy)propyl]-3-tert-butylphenyl]-5-chloro-2H-benzotriazole; Phenol, 2-(5-ethenyl-2H-benzotriazol-2-yl)-4-methyl-, homopolymer (9Cl) (CAS#83063-87-0). In accordance with the invention, the polymerizable composition comprises about 0.2% to about 5.0%, preferably about 0.3% to about 2.5%, more preferably about 0.5% to about 1.8%, by weight of a UV-absorbing agent.

Where a vinylic monomer capable of absorbing ultra-violet radiation and high energy violet light (HEVL) is used in the invention, a Germane-based Norrish Type I photoinitiator and a light source including a light in the region of about 400 to about 550 nm are preferably used to initiate a free-radical polymerization. Any Germane-based Norrish Type I photoinitiators can be used in this invention, so long as they are capable of initiating a free-radical polymerization under irradiation with a light source including a light in the region of about 400 to about 550 nm. Examples of Germane-based Norrish Type I photoinitiators are acylgermanium compounds described in U.S. Pat. No. 7,605,190 (herein incorporated by reference in its entirety). Preferably, the monomer of lens-forming materials comprises at least one of the following acylgermanium compounds.

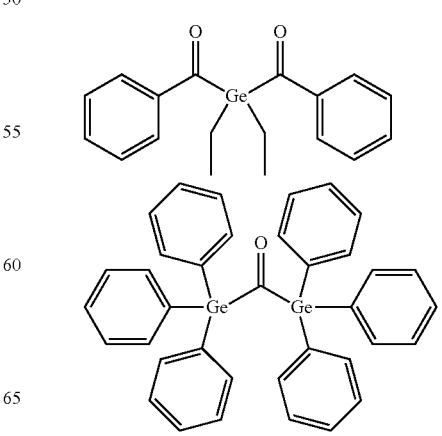

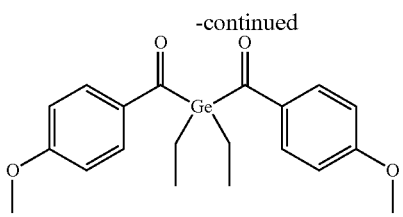

In accordance with the invention, a polymerizable silicone composition can be a solution or a melt at a temperature from about 20° C. to about 85° C. Preferably, a polymerizable composition is a solution of all desirable components in a suitable solvent, or a mixture of suitable solvents.

A polymerizable silicone composition can be prepared by dissolving all of the desirable components in any suitable solvent, such as, water, a mixture of water and one or more organic solvents miscible with water, an organic solvent, or a mixture of one or more organic solvents, as known to a person skilled in the art.

Example of preferred organic solvents includes without limitation, tetrahydrofuran, tripropylene glycol methyl ether, dipropylene glycol methyl ether, ethylene glycol n-butyl ether, ketones (e.g., acetone, methyl ethyl ketone, etc.), diethylene glycol n-butyl ether, diethylene glycol methyl ether, ethylene glycol phenyl ether, propylene glycol methyl ether, propylene glycol methyl ether acetate, dipropylene glycol methyl ether acetate, propylene glycol n-propyl ether, dipropylene glycol n-propyl ether, tripropylene glycol n-butyl ether, propylene glycol n-butyl ether, dipropylene glycol n-butyl ether, tripropylene glycol n-butyl ether, propylene glycol phenyl ether dipropylene glycol dimetyl ether, polyethylene glycols, polypropylene glycols, ethyl acetate, butyl acetate, amyl acetate, methyl lactate, ethyl lactate, i-propyl lactate, methylene chloride, 2-butanol, 1-propanol, 2-propanol, menthol, cyclohexanol, cyclopentanol and exonorborneol, 2-pentanol, 3-pentanol, 2-hexanol, 3-hexanol, 3-methyl-2-butanol, 2-heptanol, 2-octanol, 2-nonanol, 2-decanol, 3-octanol, norborneol, tert-butanol, tert-amyl alcohol, 2-methyl-2-pentanol, 2,3-dimethyl-2-butanol, 3-methyl-3-pentanol, 1-methylcyclohexanol, 2-methyl-2-hexanol, 3,7-dimethyl-3-octanol, 1-chloro-2-methyl-2-propanol, 2-methyl-2-heptanol, 2-methyl-2-octanol, 2-2-methyl-2-nonanol, 2-methyl-2-decanol, 3-methyl-3-hexanol, 3-methyl-3-heptanol, 4-methyl-4-heptanol, 3-methyl-3-octanol, 4-methyl-4-octanol, 3-methyl-3-nonanol, 4-methyl-4-nonanol, 3-methyl-3-octanol, 3-ethyl-3-hexanol, 3-methyl-3-heptanol, 4-ethyl-4-heptanol, 4-propyl-4-heptanol, 4-isopropyl-4-heptanol, 2,4-dimethyl-2-pentanol, 1-methylcyclopentanol, 1-ethylcyclopentanol, 1-ethylcyclopentanol, 3-hydroxy-3-methyl-1-butene, 4-hydroxy-4-methyl-1-cyclopentanol, 2-phenyl-2-propanol, 2-methoxy-2-methyl-2-propanol 2,3,4-trimethyl-3-pentanol, 3,7-dimethyl-3-octanol, 2-phenyl-2-butanol, 2-methyl-1-phenyl-2-propanol and 3-ethyl-3-pentanol, 1-ethoxy-2-propanol, 1-methyl-2-propanol, t-amyl alcohol, isopropanol, 1-methyl-2-pyrrolidone, N,N-dimethylpropionamide, dimethyl formamide, dimethyl acetamide, dimethyl propionamide, N-methyl pyrrolidinone, and mixtures thereof.

A polymerizable silicone composition can be cured thermally or actinically as known to a person skilled in the art. Preferably, a polymerizable silicone composition is cured in molds for making medical devices.

Lens molds for making medical devices (e.g., contact lenses) are well known to a person skilled in the art and, for example, are employed in cast molding or spin casting. For example, a mold (for cast molding) generally comprises at least two mold sections (or portions) or mold halves, i.e. first and second mold halves. The first mold half defines a first molding (or optical) surface and the second mold half defines a second molding (or optical) surface. The first and second mold halves are configured to receive each other such that a lens forming cavity is formed between the first molding surface and the second molding surface. The molding surface of a mold half is the cavity-forming surface of the mold and in direct contact with lens-forming material.

Methods of manufacturing mold sections for cast-molding a contact lens are generally well known to those of ordinary skill in the art. The process of the present invention is not limited to any particular method of forming a mold. In fact, any method of forming a mold can be used in the present invention. The first and second mold halves can be formed through various techniques, such as injection molding or lathing. Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S. Pat. No. 5,894,002 to Boneberqer et al., which are also incorporated herein by reference.

Virtually all materials known in the art for making molds can be used to make molds for making medical devices. For example, polymeric materials, such as polyethylene, polypropylene, polystyrene, PMMA, Topas® COC grade 8007-S10 (clear amorphous copolymer of ethylene and norbornene, from Ticona GmbH of Frankfurt, Germany and Summit, N.J.), or the like can be used. Other materials that allow UV light transmission could be used, such as quartz glass and sapphire.

In a preferred embodiment, reusable molds are used and the polymerizable silicone composition is cured actinically under a spatial limitation of actinic radiation to form a silicone medical device. Examples of preferred reusable molds are those disclosed in U.S. Pat. Nos. 6,800,225, 7,384,590, and 7,387,759, which are incorporated by reference in their entireties. Reusable molds can be made of quartz, glass, sapphire, $CaF_2$, a cyclic olefin copolymer (such as for example, Topas® COC grade 8007-S10 (clear amorphous copolymer of ethylene and norbornene) from Ticona GmbH of Frankfurt, Germany and Summit, N.J., Zeonex® and Zeonor® from Zeon Chemicals LP, Louisville, Ky.), polymethylmethacrylate (PMMA), polyoxymethylene from DuPont (Delrin), Ultem® (polyetherimide) from G.E. Plastics, PrimoSpire®, etc.

In accordance with the invention, the silicone composition or the polymerizable silicone composition can be introduced (dispensed) into a cavity formed by a mold according to any known methods.

After the silicone composition or the polymerizable silicone composition is dispensed into the mold, it is crosslinked or polymerized to produce a medical device (i.e., a substrate). Crosslinking or polymerizing may be initiated thermally or actinically, preferably by exposing the lens-forming composition in the mold to a spatial limitation of actinic radiation to crosslink the polymerizable components in the polymerizable composition.

Opening of the mold so that the molded article can be removed from the mold may take place in a manner known per se.

The molded substrate can be subject to extraction to remove unpolymerized polymerizable components. The extraction solvent can be any solvent known to a person skilled in the art. Examples of suitable extraction solvent are those described above.

Thereafter, for example, in the cast molding manufacturing method, the lens (or substrate) may be released from the mold and subjected to post-molding processes, such as, extraction, hydration, etc.

A silicone substrate can be dried according to any method known to a person skilled in the art and then be subjected to plasma-treatment by exposing it to a plasma (also referred to as "electrical glow discharge plasma"). Examples of plasma treatment are those disclosed in U.S. Pat. Nos. 4,143,949; 4,312,575; 5,464,667; 6,881,269; and 7,078,074 (herein incorporated by references in their entireties)

A person skilled in the art understand well that a plasma (i.e., electrical glow discharge plasma) is a partially ionized gas which consists of large concentrations of excited atomic, molecular, ionic, and free-radical species and which is generated subjecting a gas in a vacuum chamber to an electric field, typically at radio frequency (rf) (or at a microwave or other frequency). The excited species interact with solid surfaces of an article placed in the plasma, resulting in the chemical and physical modification of the material surface.

For a review of plasma treatment and its uses reference is made to R. Hartmann "Plasma polymerisation: Grundlagen, Technik und Anwendung, Jahrb. Oberflächentechnik (1993) 49, pp. 283-296, Battelle-Inst. e.V. Frankfurt/Main Germany; H. Yasuda, "Glow Discharge Polymerization", Journal of Polymer Science: Macromolecular Reviews, vol. 16 (1981), pp. 199-293; H. Yasuda, "Plasma Polymerization", Academic Press, Inc. (1985); Frank Jansen, "Plasma Deposition Processes", in "Plasma Deposited Thin Films", ed. by T. Mort and F. Jansen, CRC Press Boca Raton (19); O. Auciello et al. (ed.) "Plasma-Surface Interactions and Processing of Materials" publ. by Kluwer Academic Publishers in NATO ASI Series; Series E: Applied Sciences, vol. 176 (1990), pp. 377-399; and N. Dilsiz and G. Akovali "Plasma Polymerization of Selected Organic Compounds", Polymer, vol. 37 (1996) pp. 333-341.

As an illustrated example of plasma treatment of silicone substrates, one or more silicone substrates are placed in a reactor chamber between opposing electrodes. The chamber is then sealed and depressurized by a vacuum system. Significant time is required to pump the system to the operative pressure. When a suitable pressure is achieved in the chamber, a process gas is introduced into the chamber interior, and the electrodes are energized. The resulting plasma cloud may apply a thin polymeric coating to the substrate and/or change the chemical composition of the substrate surface depending upon the process gas used. After an appropriate time, the electrodes are de-energized, and the reactor chamber is brought back to atmospheric pressure so that the substrates may be removed.

Plasma treatment systems are known to a person skilled in the art and have been disclosed in patents and articles. For example, Peng Ho and Yasuda describe, in their paper ("Ultrathin Coating Of Plasma Polymer Of Methane Applied On The Surface Of Silicone Contact Lenses," Journal of Biomedical Materials Research, Vol. 22, 919-937 (1988), herein incorporated by reference in its entirety), a batch system (or a rotary plasma system) including a bell-shaped vacuum chamber in which opposing aluminum electrodes are disposed and a rotatable aluminum plate sits between the electrodes and is driven by an induction motor within the system. Matsuzawa and Winterton disclose in U.S. Pat. No. 6,881,269 (herein incorporated by reference in its entirety) a linear plasma system.

In accordance with the invention, the silicone substrate in a dried state is treated with a plasma generated in a plasma gas (i.e., an atmosphere) compose of air, $CO_2$, or a mixture of a $C_1$-$C_6$ hydrocarbon and a secondary gas selected from the group consisting of air, $CO_2$, $N_2$, and combinations thereof, preferably air, $CO_2$ or a mixture of a $C_1$-$C_4$ hydrocarbon and a secondary gas selected from the group consisting of air, $CO_2$, $N_2$, and combinations thereof, more preferably $CO_2$ or a mixture of methane and a secondary gas selected from the group consisting of air, $CO_2$, $N_2$, and combinations thereof, even more preferably $CO_2$ or a mixture of methane and air, or a mixture of methane and $CO_2$.

In accordance with the invention, the thickness of a plasma coating (layer) is less than 40 nm, preferably from about 1 nm to about 35 nm, more preferably from about 2 nm to about 30 nm. The thickness of a plasma coating (layer) can be determined according to any know method. For example, it can be measured by ellipsometry on silicon wafers which are plasma-treated together with silicone substrates. A person knows how to control the plasma conditions for obtaining a desired thickness of a particular plasma coating (layer) on a silicone substrate.

Where a plasma used in plasma treatment is generated in an atmosphere (i.e., plasma gas) composed of a mixture of a $C_1$-$C_6$ hydrocarbon and a secondary gas selected from the group consisting of air, $CO_2$, $N_2$, and combinations thereof, the composition of a plasma gas can be controlled by the flow rates (sccm) of each individual gases in the mixture. Preferably, the flow rate ratio of a $C_1$-$C_6$ hydrocarbon over the secondary gas (air, $CO_2$, $N_2$, or combinations thereof) is from about 1:4 to about 4:1.

In another preferred embodiment, substep (2)(a) is carried out in a plasma generated in a plasma gas (i.e., an atmosphere) composed of air.

In another preferred embodiment, substep (2)(a) is carried out in a plasma generated in a plasma gas (i.e., an atmosphere) composed of $CO_2$.

In another preferred embodiment, substep (2)(a) is carried out in a plasma generated in a plasma gas (i.e., an atmosphere) composed of a mixture of a $C_1$-$C_6$ hydrocarbon and a secondary gas selected from the group consisting of air, $CO_2$, $N_2$, and combinations thereof (more preferably $CO_2$ or a mixture of a $C_1$-$C_4$ hydrocarbon and a secondary gas selected from the group consisting of air, $CO_2$, $N_2$, and combinations thereof, more preferably $CO_2$ or a mixture of methane and a secondary gas selected from the group consisting of air, $CO_2$, $N_2$, and combinations thereof, even more preferably $CO_2$ or a mixture of methane and air, or a mixture of methane and $CO_2$).

In another preferred embodiment, the surface treatment further comprises, prior to substep (2)(a), a substep of plasma-pretreating the surface of the silicone substrate in the dry state with a plasma generated in a plasma gas (i.e., an atmosphere) composed of air, wherein substep (2)(a) is carried out in a plasma generated in a plasma gas (i.e., an atmosphere) composed of a mixture of a $C_1$-$C_6$ hydrocarbon and a secondary gas selected from the group consisting of air, $CO_2$, $N_2$, and combinations thereof (more preferably a mixture of a $C_1$-$C_4$ hydrocarbon and a secondary gas selected from the group consisting of air, $CO_2$, $N_2$, and combinations thereof, even more preferably $CO_2$ or a mixture of methane and air, or a mixture of methane and $CO_2$).

In accordance with the invention, the duration of the plasma treatment, i.e., substep (2)(a), is from about 10 minutes to about 60 minutes, whereas the duration of the plasma pretreatment (i.e., the substep of plasma-pretreating) is less than 10 minutes, preferably from about 1 to about 5 minutes.

It should be understood that a surface treatment in a method of the invention can comprise one or more plasma treatment steps in plasmas generated in the same or difference plasma gases In accordance with the invention, contacting of a plasma-treated silicone substrate with a first aqueous solution of a reactive hydrophilic polymer can occur by dipping it into the aqueous solution or by spraying it with the aqueous solution. One contacting process involves solely dipping the plasma-treated silicone substrate in a bath of a first aqueous solution for a period of time or alternatively dipping the plasma-treated silicone substrate sequentially in a series of bath of aqueous solutions for a fixed shorter time period for each bath. Another contacting process involves solely spray a first aqueous solution. However, a number of alternatives involve various combinations of spraying- and dipping-steps may be designed by a person having ordinary skill in the art. The contacting time can be from about 5 seconds to about 10 hours. A person knows how to control the contacting time for obtaining a desired thickness of a particular reactive polymer layer on a silicone substrate with a prime plasma layer thereon.

In a preferred embodiment, after being removed from the plasma treatment system, the plasma treated silicone substrate is placed in contact with a first aqueous solution including a reactive hydrophilic polymer having multiple reactive functional groups selected from the group consisting of carboxyl groups, primary amine groups, secondary amine groups, and combinations thereof, within a time period of about 40 minutes or less (preferably about 30 minutes or less, more preferably about 20 minutes or less) immediately after the plasma-treatment sub-step and before contacting with water, an organic solvent, a mixture of water and one or more organic solvents, a mixture of two or more organic solvent, or any aqueous or organic-based solution free of any reactive polymer. It is believed that there may be reactive radicals in a prime plasma layer on the surface of a plasma-treated silicone substrate. When a reactive polymer is present in a first aqueous solution for contacting a plasma-treated silicone substrate within 40 minutes immediately after plasma treatment, those free radicals may react with the reactive polymer to provide sufficient anchoring sites for covalently attaching a layer of the reactive polymer onto the prime plasma layer, thereby enhancing the durability of the hydrogel coating to be formed in step (3). Preferably, the first aqueous solution comprises at least about 0.001% by weight (preferably from about 0.002% to about 20% by weight, more preferably from about 0.005% to about 15% by weight, even more preferably from about 0.01% to about 10% by weight) of a reactive hydrophilic polymer as defined above.

In another preferred embodiment, the reactive hydrophilic polymer is a polyanionic polymer comprising carboxyl groups and having a weight average molecular weight of at least 1000 Daltons (preferably from 2000 to 5,000,000 Daltons, more preferably from 5000 to 2,000,000 Daltons, even more preferably from 10,000 to 1,000,000 Daltons), and the first aqueous solution preferably has a pH from about 1.0 to about 3.0 (more preferably from about 1.5 to about 2.5, even more preferably from about 1.8 to about 2.0). The polyanionic polymer is preferably a polyanionic polymer selected from the group consisting of polyacrylic acid, polymethacrylic acid, polyethylacrylic acid, poly(acrylic acid-co-methacrylic acid), poly(acrylic acid-co-ethacrylic acid), poly(methacrylic acid-co-ethacrylic acid), and a mixture thereof, more preferably a polyanionic polymer selected from the group consisting of polyacrylic acid, polymethacrylic acid, poly(acrylic acid-co-methacrylic acid), and a mixture thereof. It is believed that there may be some reactive functional groups including silanol groups (Si—OH) in the prime plasma layer on the surface of a plasma-treated silicone contact lens (or substrate). Schmidt reported that coupling reactions can occur between a carboxyl group and a free, unreacted silanol group at low pH (e.g., pH 2.0) according to an acid-catalyzed ester condensation mechanism (S. W. Schmidt, et al., Langmuir 2010, 26(19), 15333-15338, herein incorporated by reference in its entirety).

In another preferred embodiment, the reactive hydrophilic polymer is a polycationic polymer comprising primary and/or secondary amino groups and having a weight average molecular weight of at least 1000 Daltons (preferably from 2000 to 5,000,000 Daltons, more preferably from 5000 to 2,000,000 Daltons, even more preferably from 10,000 to 1,000,000 Daltons) and the first aqueous solution preferably has a pH from about 9.5 to about 11.0 (more preferably from about 10.0 to about 11.0). The polycationic polymer is preferably selected from the group consisting of polyethyleneimine, polyallylamine, polyvinylamine, polyamidoamine, and a mixture thereof.

In another preferred embodiment, the reactive hydrophilic polymer further comprises azetidinium groups and has a weight average molecular weight of at least 1000 Daltons (preferably from 2000 to 5,000,000 Daltons, more preferably from 5000 to 2,000,000 Daltons, even more preferably from 10,000 to 1,000,000 Daltons), and the first aqueous solution preferably has a pH of less than about 8.0 (more preferably from about 2.0 to about 8.0, even more preferably from about 6.0 to about 8.0). In this preferred embodiment, the reactive hydrophilic polymer is preferably a chemically-modified poly(2-oxazoline-co-ethyleneimine)-epichlorohydrin, a chemically-modified polyamidoamine-epichlorohydrin, or combinations thereof. Preferably, the chemically-modified poly(2-oxazoline-co-ethyleneimine)-epichlorohydrin or the chemically-modified polyamidoamine-epichlorohydrin comprises (i) from about 20% to about 95% by weight of first polymer chains derived from a polyamidoamine-epichlorohydrin or a poly(2-oxazoline-co-ethyleneimine)-epichlorohydrin, (ii) from about 5% to about 80% by weight of hydrophilic moieties or second polymer chains derived from at least one hydrophilicity-enhancing agent having at least two reactive functional group selected from the group consisting of amino group, carboxyl group, thiol group, and combination thereof, wherein the hydrophilic moieties or second polymer chains are covalently attached to the first polymer chains through one or more covalent linkages each formed between one azetitdinium group of the polyamidoamine-epichlorohydrin or the poly(2-oxazoline-co-ethyleneimine)-epichlorohydrin and one amino, carboxyl or thiol group of the hydrophilicity-enhancing agent, and (iii) azetidinium groups which are non-reacted parts of the first polymer chains or pendant or terminal groups covalently attached to the first polymer chains while the reactive functional groups are non-reacted parts of the hydrophilicity-enhancing agent. The composition of a chemically-modified poly(2-oxazoline-co-ethyleneimine)-epichlorohydrin or a chemically-modified polyamidoamine-epichlorohydrin is determined by the composition (based on the total weight of the reactants) of a reactants mixture used for such a polymer according to the crosslinking reactions shown in Scheme I Scheme I

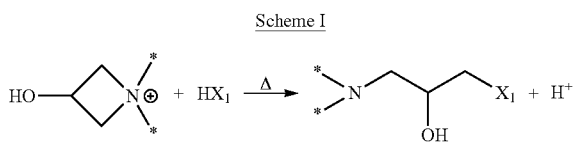

in which $X_1$ is —S—*, —OC(=O)—*, or —NR'—* in which R' is hydrogen or a $C_1$-$C_{20}$ unsubstituted or substituted alkyl group, and * represents an organic radical. For example, if a reactant mixture comprises about 75% by weight of a polyamidoamine-epichlorohydrin and about 25% by weight of at least one hydrophilicity-enhancing agent based on the total weight of the reactants, then the resultant chemically-modified polyamidoamine-epichlorohydrin comprises about 75% by weight of first polymer chains derived from the polyamioamine-epichlorohydrin and about 25% by weight of hydrophilic moieties or second polymer chains derived from said at least one hydrophilicity-enhancing agent. The azetidinium groups and reactive functional groups (carboxyl, primary amino, and/or secondary amino groups) of the chemically-modified poly(2-oxazoline-co-ethyleneimine)-epichlorohydrin or the chemically-modified polyamidoamine-epichlorohydrin are those azetidinium groups (of the polyamidoamine-epichlorohydrin) and the reactive functional groups (of the hydrophilicity-enhancing agent), which do not participate in crosslinking reactions for preparing the chemically-modified poly (2-oxazoline-co-ethyleneimine)-epichlorohydrin or the chemically-modified polyamidoamine-epichlorohydrin.

Any suitable hydrophilicity-enhancing agents can be used in the invention so long as they contain at least one amino group, at least one carboxyl group, and/or at least one thiol group.

Examples of suitable hydrophilicity-enhancing agents are described below and can be used in the preferred embodiment for preparing chemically-modified poly(2-oxazoline-co-ethyleneimine)-epichlorohydrin or the chemically-modified polyamidoamine-epichlorohydrin.

It is believed that a reactive base coating comprising a prime plasma layer and a reactive polymer layer can be advantageously used for forming a lubricious non-silicone hydrogel coating on a silicone contact lens. Such a lubricious non-silicone hydrogel coating may have low susceptibility to deposition and accumulation of positively charged antimicrobials because of minimized concentration of carboxyl groups in the base coating. Further, the combination of the base coating and the lubricious non-silicone hydrogel coating can have an adequate thickness and a high cross-linking density for preventing silicone from migrating onto the surface of a silicone substrate (preferably a silicone contact lens) even it is stored in a dry state in the air for an extended period of time. In addition, the underlying prime plasma layer may provide the adequate hydrophilicity (or wettability) of the silicone hydrogel contact lens sufficient for ensuring its biocompatibility, even though it is not lubricious, in case if the non-silicone hydrogel coating would be damaged during the handling and wearing of the contact lens. In addition, this surface treatment may provide a platform for building a lubricious coating having a desired durability, e.g., lasting up to two days for daily-disposable lenses, lasting 7 to 35 days for weekly, biweekly or monthly disposable lenses.

In accordance with the invention, the silicone contact lens (or substrate) with the base coating thereon is heated in a second aqueous solution which comprises a water-soluble and thermally-crosslinkable hydrophilic polymeric material having azetidinium groups and optionally (but preferably) amino or carboxyl groups, at a temperature of from about 60° C. to about 140° C. for a time period sufficient long to crosslink the water-soluble thermally-crosslinkable hydrophilic polymeric material and the base coating so as to form a hydrogel coating on the silicone contact lens (or substrate), wherein the hydrogel coating on the silicone contact lens (or substrate) has a friction rating of 2 or less. It should be understood that the first aqueous solution and the second aqueous solution can be identical to or different from each other.

A water-soluble and thermally-crosslinkable hydrophilic polymeric material used in step (3) is preferably a poly(2-oxazoline-co-ethyleneimine)-epichlorohydrin, a chemically-modified poly(2-oxazoline-co-ethyleneimine)-epichlorohydrin, a chemically-modified polyamidoamine-epichlorohydrin, or combinations thereof, wherein the chemically-modified poly(2-oxazoline-co-ethyleneimine)-epichlorohydrin or the chemically-modified polyamidoamine-epichlorohydrin comprises (i) from about 20% to about 95% by weight of first polymer chains derived from a polyamidoamine-epichlorohydrin or a poly(2-oxazoline-co-ethyleneimine)-epichlorohydrin, (ii) from about 5% to about 80% by weight of hydrophilic moieties or second polymer chains derived from at least one hydrophilicity-enhancing agent having at least one reactive functional group selected from the group consisting of amino group, carboxyl group, thiol group, and combination thereof, wherein the hydrophilic moieties or second polymer chains are covalently attached to the first polymer chains through one or more covalent linkages each formed between one azetitdinium group of the polyamidoamine-epichlorohydrin or the poly (2-oxazoline-co-ethyleneimine)-epichlorohydrin and one amino, carboxyl or thiol group of the hydrophilicity-enhancing agent, and (iii) azetidinium groups which are parts of the first polymer chains or pendant or terminal groups covalently attached to the first polymer chains.

A preferred class of hydrophilicity-enhancing agents include without limitation: primary amino-, secondary amino-, carboxyl- or thiol-containing monosaccharides (e.g., 3-amino-1,2-propanediol, 1-thiolglycerol, 5-keto-D-gluconic acid, galactosamine, glucosamine, galacturonic acid, gluconic acid, glucosaminic acid, mannosamine, saccharic acid 1,4-lactone, saccharide acid, Ketodeoxynonulosonic acid, N-methyl-D-glucamine, 1-amino-1-deoxy-β-D-galactose, 1-amino-1-deoxysorbitol, 1-methylamino-1-deoxysorbitol, N-aminoethyl gluconamide); primary amino-, secondary amino-, carboxyl- or thiol-containing disaccharides (e.g., chondroitin disaccharide sodium salt, di(13-D-xylopyranosyl)amine, digalacturonic acid, heparin disaccharide, hyaluronic acid disaccharide, Lactobionic acid); and primary amino-, secondary amino-, carboxyl- or thiol-containing oligosaccharides (e.g., carboxymethyl-β-cyclodextrin sodium salt, trigalacturonic acid); and combinations thereof.

Another preferred class of hydrophilicity-enhancing agents is hydrophilic polymers having one or more (primary or secondary) amino, carboxyl and/or thiol groups. More preferably, the content of the amino (—NHR' with R' as defined above), carboxyl (—COOH) and/or thiol (—SH) groups in a hydrophilic polymer as a hydrophilicity-enhancing agent is less than about 40%, preferably less than about 30%, more preferably less than about 20%, even more preferably less than about 10%, by weight based on the total weight of the hydrophilic polymer.

One preferred class of hydrophilic polymers as hydrophilicity-enhancing agents are (primary or secondary) amino- or carboxyl-containing polysaccharides, for example, such as, carboxymethylcellulose (having a carboxyl content of about 40% or less, which is estimated based on the composition of repeating units, —[$C_6H_{10-m}O_5(CH_2CO_2H)_m$]— in which m is 1 to 3), carboxyethylcellulose (having a carboxyl content of about 36% or less, which is estimated based on the composition of repeating units, —[$C_6H_{10-m}O_5(C_2H_4CO_2H)_m$]— in which m is 1 to 3) carboxypropylcellulose (having a carboxyl content of about 32% or less, which is estimated based on the composition of repeating units, —[$C_6H_{10-m}O_5(C_3H_6CO_2H)_m$]—, in which m is 1 to 3), hyaluronic acid (having a carboxyl content of about 11%, which is estimated based on the composition of repeating units, —($C_{13}H_{20}O_9NCO_2H$)—), chondroitin sulfate (having a carboxyl content of about 9.8%, which is estimated based on the composition of repeating units, —($C_{12}H_{18}O_{13}NS\ CO_2H$)—), or combinations thereof.

Another preferred class of hydrophilic polymers as hydrophilicity-enhancing agents include without limitation: poly(ethylene glycol) (PEG) with mono-amino (primary or secondary amino), carboxyl or thiol group (e.g., PEG-NH$_2$, PEG-SH, PEG-COOH); H$_2$N-PEG-NH$_2$; HOOC-PEG-COOH; HS-PEG-SH; H$_2$N-PEG-COOH; HOOC-PEG-SH; H$_2$N-PEG-SH; multi-arm PEG with one or more amino (primary or secondary), carboxyl or thiol groups; PEG dendrimers with one or more amino (primary or secondary), carboxyl or thiol groups; a diamino-(primary or secondary) or dicarboxyl-terminated homo- or co-polymer of a non-reactive hydrophilic vinylic monomer; a monoamino-(primary or secondary) or monocarboxyl-terminated homo- or co-polymer of a non-reactive hydrophilic vinylic monomer; a copolymer which is a polymerization product of a composition comprising (1) about 60% by weight or less, preferably from about 0.1% to about 30%, more preferably from about 0.5% to about 20%, even more preferably from about 1% to about 15%, by weight of one or more reactive vinylic monomers and (2) at least one non-reactive hydrophilic vinylic monomer; and combinations thereof. Reactive vinylic monomer(s) and non-reactive hydrophilic vinylic monomer(s) are those described previously.

More preferably, a hydrophilic polymer as a hydrophilicity-enhancing agent is PEG-NH$_2$; PEG-SH; PEG-COOH; H$_2$N-PEG-NH$_2$; HOOC-PEG-COOH; HS-PEG-SH; H$_2$N-PEG-COOH; HOOC-PEG-SH; H$_2$N-PEG-SH; multi-arm PEG with one or more amino, carboxyl or thiol groups; PEG dendrimers with one or more amino, carboxyl or thiol groups; a monoamino-, monocarboxyl-, diamino- or dicarboxyl-terminated homo- or copolymer of a non-reactive hydrophilic vinylic monomer selected from the group consisting of acryamide (AAm), N,N-dimethylacrylamide (DMA), N-vinylpyrrolidone (NVP), N-vinyl-N-methyl acetamide, glycerol (meth)acrylate, hydroxyethyl (meth)acrylate, N-hydroxyethyl (meth)acrylamide, C$_1$-C$_4$-alkoxy polyethylene glycol (meth)acrylate having a weight average molecular weight of up to 400 Daltons, vinyl alcohol, N-methyl-3-methylene-2-pyrrolidone, 1-methyl-5-methylene-2-pyrrolidone, 5-methyl-3-methylene-2-pyrrolidone, N,N-dimethylaminoethyl (meth)acrylate, N,N-dimethylaminopropyl (metha)crylamide, (meth)acryloyloxyethyl phosphorylcholine, and combinations thereof; a copolymer which is a polymerization product of a composition comprising (1) from about 0.1% to about 30%, preferably from about 0.5% to about 20%, more preferably from about 1% to about 15%, by weight of acrylic acid, C$_1$-C$_3$ alkylacrylic acid, allylamine and/or amino-C$_2$-C$_4$ alkyl (meth)acrylate, and (2) at least one non-reactive hydrophilic vinylic monomer selected from the group consisting of acryamide, N,N-dimethylacrylamide, N-vinylpyrrolidone, (meth)acryloyloxyethyl phosphorylcholine, N-vinyl-N-methyl acetamide, glycerol (meth)acrylate, hydroxyethyl (meth)acrylate, N-hydroxyethyl (meth)acrylamide, C$_1$-C$_4$-alkoxy polyethylene glycol (meth)acrylate having a weight average molecular weight of up to 400 Daltons, vinyl alcohol, and combination thereof.

Most preferably, the hydrophilicity-enhancing agent as a hydrophilicity-enhancing agent is PEG-NH$_2$; PEG-SH; PEG-COOH; monoamino-, monocarboxyl-, diamino- or dicarboxyl-terminated polyvinylpyrrolidone; monoamino-, monocarboxyl-, diamino- or dicarboxyl-terminated polyacrylamide; monoamino-, monocarboxyl-, diamino- or dicarboxyl-terminated poly(DMA); monoamino- or monocarboxyl-, diamino- or dicarboxyl-terminated poly(DMA-co-NVP); monoamino-, monocarboxyl-, diamino- or dicarboxyl-terminated poly(NVP-co-N,N-dimethylaminoethyl (meth)acrylate)); monoamino-, monocarboxyl-, diamino- or dicarboxyl-terminated poly(vinylalcohol); monoamino-, monocarboxyl-, diamino- or dicarboxyl-terminated poly[(meth)acryloyloxyethyl phosphrylcholine] homopolymer or copolymer; monoamino-, monocarboxyl-, diamino- or dicarboxyl-terminated poly(NVP-co-vinyl alcohol); monoamino-, monocarboxyl-, diamino- or dicarboxyl-terminated poly(DMA-co-vinyl alcohol); poly[(meth)acrylic acid-co-acrylamide] with from about 0.1% to about 30%, preferably from about 0.5% to about 20%, more preferably from about 1% to about 15%, by weight of (meth)acrylic acid; poly[(meth)acrylic acid-co-NVP) with from about 0.1% to about 30%, preferably from about 0.5% to about 20%, more preferably from about 1% to about 15%, by weight of (meth)acrylic acid; a copolymer which is a polymerization product of a composition comprising (1) (meth)acryloyloxyethyl phosphorylcholine and (2) from about 0.1% to about 30%, preferably from about 0.5% to about 20%, more preferably from about 1% to about 15%, by weight of acrylic acid, C$_1$-C$_3$ alkylacrylic acid, allylamine and/or amino-C$_2$-C$_4$alkyl (meth)acrylate; and combination thereof.

PEGs with functional groups and multi-arm PEGs with functional groups can be obtained from various commercial suppliers, e.g., Polyscience, and Shearwater Polymers, inc., etc.

Monoamino-, monocarboxyl-, diamino- or dicarboxyl-terminated homo- or copolymers of one or more non-reactive hydrophilic vinylic monomers or of a phosphorylcholine-containing vinylic monomer can be prepared according to procedures described in U.S. Pat. No. 6,218,508, herein incorporated by reference in its entirety. For example, to prepare a diamino- or dicarboxyl-terminated homo- or co-polymer of a non-reactive hydrophilic vinylic monomer, the non-reactive vinylic monomer, a chain transfer agent with an amino or carboxyl group (e.g., 2-aminoethanethiol, 2-mercaptopropinic acid, thioglycolic acid, thiolactic acid, or other hydroxymercaptanes, aminomercaptans, or carboxyl-containing mercaptanes) and optionaly other vinylic monomer are copolymerized (thermally or actinically) with a reactive vinylic monomer (having an amino or carboxyl group), in the presence of an free-radical initiator. Generally, the molar ratio of chain transfer agent to that of all of vinylic monomers other than the reactive vinylic monomer is from about 1:5 to about 1:100, whereas the molar ratio of chain transfer agent to the reactive vinylic monomer is 1:1. In such preparation, the chain transfer agent with amino or carboxyl group is used to control the molecular weight of the resultant hydrophilic polymer and forms a terminal end of the resultant hydrophilic polymer so as to provide the resultant hydrophilic polymer with one terminal amino or carboxyl group, while the reactive vinylic monomer provides the other terminal carboxyl or amino group to the resultant hydrophilic polymer. Similarly, to prepare a monoamino- or monocarboxyl-terminated homo- or copolymer of a non-reactive hydrophilic vinylic monomer, the non-reactive vinylic monomer, a chain transfer agent with an amino or carboxyl group (e.g., 2-aminoethanethiol, 2-mercaptopropinic acid, thioglycolic acid, thiolactic acid, or other hydroxymercaptanes, aminomercaptans, or carboxyl-containing mercaptanes) and optionally other vinylic monomers are copolymerized (thermally or actinically) in the absence of any reactive vinylic monomer.

As used herein, a copolymer of a non-reactive hydrophilic vinylic monomer refers to a polymerization product of a non-reactive hydrophilic vinylic monomer with one or more additional vinylic monomers. Copolymers comprising a non-reactive hydrophilic vinylic monomer and a reactive vinylic monomer (e.g., a carboxyl-containing vinylic monomer, a primary amino group-containing vinylic monomer or a secondary amino group-containing vinylic monomer) can be prepared according to any well-known radical polymerization methods or obtained from commercial suppliers. Copolymers containing methacryloyloxyethyl phosphorylcholine and carboxyl-containing vinylic monomer (or amino-containing vinylic monomer) can be obtained from NOF Corporation (e.g., LIPIDURE®-A and -AF).

The weight average molecular weight $M_w$ of the hydrophilic polymer having at least one amino, carboxyl or thiol group (as a hydrophilicity-enhancing agent) is preferably from about 500 to about 1,000,000, more preferably from about 1,000 to about 500,000, even more preferably from about 5,000 to about 250,000 Daltons.

In accordance with the invention, the reaction between a hydrophilicity-enhancing agent and a poly(2-oxazoline-co-ethyleneimine)-epichlorohydrin copolymer (or a polyamidoamine-epichlorohydrin) is carried out at a temperature of from about 40° C. to about 80° C. for a period of time sufficient (from about 0.3 hour to about 24 hours, preferably from about 1 hour to about 12 hours, even more preferably from about 2 hours to about 8 hours) to form a chemically-modified poly(2-oxazoline-co-ethyleneimine)-epichlorohydrin or a chemically-modified polyamidoamine-epichlorohydrin.

In accordance with the invention, the concentration of a hydrophilicity-enhancing agent relative to a poly(2-oxazoline-co-ethyleneimine)-epichlorohydrin or a polyamidoamine-epichlorohydrin must be selected not to render a resultant hydrophilic polymeric material water-insoluble (i.e., a solubility of less than 0.005 g per 100 ml of water at room temperature) and not to consume more than about 99%, preferably about 98%, more preferably about 97%, even more preferably about 96% of the azetidinium groups of the poly(2-oxazoline-co-ethyleneimine)-epichlorohydrin or a polyamidoamine-epichlorohydrin.

In a preferred embodiment, a chemically-modified poly (2-oxazoline-co-ethyleneimine)-epichlorohydrin or a chemically-modified polyamidoamine-epichlorohydrin comprises: azetidinium groups; from about 20% to about 95%, preferably from about 35% to about 90%, more preferably from about 50% to about 85%, by weight of first polymer chains derived from a poly(2-oxazoline-co-ethyleneimine)-epichlorohydrin copolymer or a polyamidoamine-epichlorohydrin; and from about 5% to about 80%, preferably from about 10% to about 65%, even more preferably from about 15% to about 50%, by weight of hydrophilic moieties or second polymer chains derived from at least one hydrophilicity-enhancing agent having at least one reactive functional group selected from the group consisting of primary amino group, secondary amino group, carboxyl group, thiol group, and combination thereof.

Preferably, the step of heating (step (3)) is performed by autoclaving the silicone contact lens (or substrate) with a base coating thereon immersed in a packaging solution (i.e., a buffered aqueous solution) in a sealed lens package at a temperature of from about 115° C. to about 125° C. for approximately 20-90 minutes. In accordance with this embodiment of the invention, the packaging solution is a buffered aqueous solution which is ophthalmically safe after autoclave.

Lens packages (or containers) are well known to a person skilled in the art for autoclaving and storing a soft contact lens (a medical device). Any lens (or device) packages can be used in the invention. Preferably, a lens (or device) package is a blister package which comprises a base and a cover, wherein the cover is detachably sealed to the base, wherein the base includes a cavity for receiving a sterile packaging solution and the contact lens (or medical device).

Lenses (devices) are packaged in individual packages, sealed, and sterilized (e.g., by autoclave at about 120° C. or higher for at least about 30 minutes under pressure) prior to dispensing to users. A person skilled in the art will understand well how to seal and sterilize lens (or device) packages.

In accordance with the invention, a packaging solution contains at least one buffering agent and one or more other ingredients known to a person skilled in the art. Examples of other ingredients include without limitation, tonicity agents, surfactants, antibacterial agents, preservatives, and lubricants (e.g., cellulose derivatives, polyvinyl alcohol, polyvinyl pyrrolidone).

The packaging solution contains a buffering agent in an amount sufficient to maintain a pH of the packaging solution in the desired range, for example, preferably in a physiologically acceptable range of about 6.5 to about 7.5. Any known, physiologically compatible buffering agents can be used. Suitable buffering agents as a constituent of the contact lens care composition according to the invention are known to the person skilled in the art. Examples are boric acid, borates, e.g. sodium borate, citric acid, citrates, e.g. potassium citrate, bicarbonates, e.g. sodium bicarbonate, TRIS (2-amino-2-hydroxymethyl-1,3-propanediol), Bis-Tris (Bis-(2-hydroxyethyl)-imino-tris-(hydroxymethyl)-methane), bis-aminopolyols, triethanolamine, ACES (N-(2-hydroxyethyl)-2-aminoethanesulfonic acid), BES (N,N-Bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3-[N-morpholino]-propanesulfonic acid), PIPES (piperazine-N,N'-bis(2-ethanesulfonic acid), TES (N-[Tris (hydroxymethyl)methyl]-2-aminoethanesulfonic acid), salts thereof, phosphate buffers, e.g. $Na_2HPO_4$, $NaH_2PO_4$, and $KH_2PO_4$ or mixtures thereof. A preferred bis-aminopolyol is 1,3-bis(tris[hydroxymethyl]-methylamino)propane (bis-TRIS-propane). The amount of each buffer agent in a packaging solution is preferably from 0.001% to 2%, preferably from 0.01% to 1%; most preferably from about 0.05% to about 0.30% by weight.

The packaging solution has a tonicity of from about 200 to about 450 milliosmol (mOsm), preferably from about 250 to about 350 mOsm. The tonicity of a packaging solution can be adjusted by adding organic or inorganic substances which affect the tonicity. Suitable occularly acceptable tonicity agents include, but are not limited to sodium chloride, potassium chloride, glycerol, propylene glycol, polyols, mannitols, sorbitol, xylitol and mixtures thereof.

A packaging solution of the invention has a viscosity of from about 1 centipoise to about 8 centipoises, more preferably from about 1.2 centipoises to about 5 centipoises, at 25° C.

In a preferred embodiment, the packaging solution comprises preferably from about 0.01% to about 2%, more preferably from about 0.05% to about 1.5%, even more preferably from about 0.1% to about 1%, most preferably from about 0.2% to about 0.5%, by weight of a water-soluble thermally-crosslinkable hydrophilic polymeric material having azetidinium groups.

It is found that a polyanionic polymer (e.g., polyacrylic acid) cannot be deposed onto silicone contact lenses without subjecting to any plasma treatment to form a layer of polyanionic polymer (i.e., a LbL coating), whereas a polyanionic polymer (e.g., polyacrylic acid) can be deposed onto silicone contact lenses without subjecting to any plasma treatment to form a layer of polyanionic polymer (i.e., a LbL coating). It is believed that such difference may results from the difference in the surface compositions between a silicone hydrogel contact lens and a silicone contact lens. A silicone hydrogel contact lens can have both hydrophilic surface areas and hydrophobic (silicone) surface area which are intermingled with each other, whereas a silicone contact lens can have a hydrophobic (silicone) surface. For a silicone hydrogel contact lens, the hydrophilic surface areas are derived from the hydrophilic components of the silicone hydrogel, whereas the hydrophobic (silicone) surface areas are derived from the silicone components of the silicone hydrogel. For a silicone contact lens, the entire surface of the silicone contact lens is covered by silicone. It is believed that those hydrophilic surface areas are required for interacting with a polyanionic polymer (e.g., via hydrogen bonding, and the like) and anchoring a layer of polyanionic polymer.

In another aspect, the invention provides a medical device (preferably an ophthalmic device, more preferably a soft contact lens), comprising a silicone substrate made of a crosslinked silicone material and a hydrogel coating thereon, wherein the medical device in fully-hydrated state has a WBUT of at least about 5 seconds (preferably at least about 7.5 seconds, more preferably at least about 10 seconds, even more preferably at least about 12.5 seconds) and a friction rating of about 3 or lower (preferably about 2.5 or lower, more preferably about 2 or lower, even more preferably about 1.5 or lower, most preferably about 1 or lower), wherein the hydrogel coating is thermodynamically stable as characterized by having a dry-storage-induced reduction in WBUT after i days of dry storage, designated as $\Delta WBUT_{DS}(i)$, of about 45% or less (preferably about 35% or less, more preferably about 25% or less, even more preferably about 15% or less) and optionally (but preferably) a dry-storage-induced increase in friction rating after i days of dry storage, $\Delta FR_{DS}(i)$, of about 60% or less (preferably about 50% or less, more preferably about 40% or less, even more preferably about 30% or less), wherein $$\Delta WBUT_{DS}(i) = \frac{WBUT_{DS@0} - WBUT_{DS@i}}{WBUT_{DS@0}} \times 100\% \text{ and}$$

$$\Delta FR_{DS}(i) = \frac{FR_{DS@i} - FR_{DS@0}}{4} \times 100\%$$

in which $WBUT_{DS@0}$ and $FR_{DS@0}$ are the WBUT and the friction rating of the medical device in fully-hydrated state at day zero of dry storage and are determined before the medical device is dehydrated and stored in air at room temperature, and $WBUT_{DS@i}$ and $FR_{DS@i}$ are the WBUT and the friction rating of the medical device in fully hydrated state at i days of dry storage and are determined after the medical device has been fully dehydrated and stored in air at room temperature for at least i days and then has been fully rehydrated before determining the WBUT and the friction rating, wherein i is an integer of 2 or larger (preferably 7 or larger, more preferably 14 or larger, even more preferably 30 or larger, most preferably 60 or larger). Preferably, the hydrogel coating is durable as characterized by having a digital-rubbing-induced reduction in WBUT after j cycles of digital rubbing tests, $\Delta WBUT_{DR}(j)$, of about 45% or less (preferably about 35% or less, more preferably about 25% or less, even more preferably about 15% or less) and/or a digital-rubbing-induced increase in friction rating after j cycles of digital rubbing tests, $\Delta FR_{DR}(j)$, of about 60% or less (preferably about 50% or less, more preferably about 40% or less, even more preferably about 30% or less), wherein $$\Delta WBUT_{DR}(j) = \frac{WBUT_{0DR} - WBUT_{jDR}}{WBUT_{0DR}} \times 100\% \text{ and}$$

$$\Delta FR_{DR}(j) = \frac{FR_{jDR} - FR_{0DR}}{4} \times 100\%$$

in which $WBUT_{0DR}$ and $FR_{0DR}$ are the WBUT and the friction rating of the medical device which is in fully-hydrated state and is subjected to zero digital rubbing test, and $WBUT_{jDR}$ and $FR_{jDR}$ are the WBUT and the friction rating of the medical device which is in fully hydrated state and has been subjected to at least j cycles of digital rubbing tests, wherein j is an integer of 2 (preferably 7, more preferably 14, even more preferably 30). More preferably, the hydrophilic hydrogel coating has a water content of at least about 40% (preferably at least about 50%, more preferably at least about 60%, even more preferably at least about 70%, most preferably at least about 80%) by weight. Where the medical device is a soft contact lens, it preferably has an oxygen permeability (Dk) of at least about 125 barrers (preferably at least about 150 barrers, more preferably at least about 175 barrers, even more preferably at least about 200 barrers).

The water content of the hydrogel layers (the crosslinked coating) can be determined by using an Abbe refractometer which is typically used to measure the refractive index of contact lenses. There is a correlation between the refractive index of a material and the equilibrium water content of that material. This correlation has been used to determine the equilibrium content of conventional and silicone hydrogel contact lenses (see, José M. Gonsález-mêijome, et al., "Equivalences between refractive index and equilibrium water content of conventional and silicone hydrogel soft contact lenses from automated and manual refractometer", J. Biomedical Materials Research Part B: Applied Biomaterials, 80B(1), 184-191 (2007), herein incorporated by reference in its entirety). Alternatively, the water content of the hydrogel coating (the crosslinked coating) can be determined with a silicon wafer (or any thin substrate made of a non-water-absorbent material) and a hydrogel coating thereon, wherein the hydrogel coating is applied onto the thin substrate according to the identical coating process for the silicone contact lens under substantial identical conditions. The water content of the hydrogel coating then can be determined based on the difference between dry and hydrated weights of the silicon wafer (or the thin substrate) with the hydrogel coating thereon.

A soft contact lens, according to a preferred embodiment of the invention, has: a friction rating of about 2.5 or lower (preferably about 2 or lower, more preferably about 1.5 or lower, even more preferably about 1 or lower); a WBUT of at least about 5 seconds (preferably at least about 7.5 seconds, more preferably at least about 10 seconds, even more preferably at least about 15 seconds); and an oxygen permeability of at least about 125 barrers (preferably at least about 150 barrers, more preferably at least about 175 barrers, even more preferably at least about 200 barrers).

A soft contact lens, according to a preferred embodiment of the invention, further has at least one property selected from the group consisting of: an elastic modulus of about 2.0 MPa or less, preferably from about 0.1 MPa to about 1.5 MPa, more preferably from about 0.2 about 1.2 or less, even more preferably from about 0.3 MPa to about 1.0 MPa; a surface wettability characterized by having an averaged water contact angle of preferably about 80 degrees or less, more preferably about 70 degrees or less, even more preferably about 60 degrees or less, most preferably about 50 degrees or less; and combinations thereof.

In a preferred embodiment, a medical device comprises the silicone substrate, a base coating directly on the surface of the silicone substrate, and a hydrogel layer covalently attached onto the base coating. Preferably, the base coating comprises a plasma layer which is directly on the surface of the silicone substrate. More preferably, the base coating comprises a prime plasma layer and a reactive polymer layer on top of the prime plasma layer, wherein the prime plasma layer is directly on the surface of the silicone substrate and has a thickness of less than about 40 nm (preferably from about 1 nm to about 35 nm, more preferably from about 2 nm to about 30 nm).

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together, as illustrated below:

1. A medical device, comprising:
   a silicone substrate made of a crosslinked silicone material, and
   a hydrogel coating thereon,
   wherein the medical device in fully-hydrated state has a WBUT of at least about 5 seconds and a friction rating of about 3 or lower,
   wherein the hydrogel coating is thermodynamically stable as characterized by having a dry-storage-induced reduction in WBUT after i days of dry storage, designated as $\Delta WBUT_{DS}(I)$, of about 45% or less and optionally a dry-storage-induced increase in friction rating after i days of dry storage, $\Delta FR_{DS}(I)$, of about 60% or less, wherein $$\Delta WBUT_{DS}(i) = \frac{WBUT_{DS@0} - WBUT_{DS@i}}{WBUT_{DS@0}} \times 100\% \text{ and}$$

-continued $$\Delta FR_{DS}(i) = \frac{FR_{DS@i} - FR_{DS@0}}{4} \times 100\%$$

in which $WBUT_{DS@0}$ and $FR_{DS@0}$ are the WBUT and the friction rating of the medical device in fully-hydrated state at day zero of dry storage and are determined before the medical device is dehydrated and stored in air at room temperature, and $WBUT_{DS@i}$ and $FR_{DS@i}$ are the WBUT and the friction rating of the medical device in fully hydrated state at i days of dry storage and are determined after the medical device has been fully dehydrated and stored in air at room temperature for at least i days and then has been fully rehydrated before determining the WBUT and the friction rating, wherein i is an integer of 2 or larger.

2. The medical device of invention 1, wherein the medical device is an ophthalmic device.

3. The medical device of invention 2, wherein the ophthalmic device is an intraocular lens, a stent, a device under eyelids, a corneal onlay, a glaucoma shunt, or an implant.

4. The medical device of invention 1, wherein the medical device is a soft contact lens, wherein the silicone substrate is a silicone contact lens.

5. The medical device of any one of inventions 1 to 4, wherein the medical device in fully-hydrated state has a WBUT of at least about 7.5 seconds.

6. The medical device of any one of inventions 1 to 4, wherein the medical device in fully-hydrated state has a WBUT of at least about 10 seconds.

7. The medical device of any one of inventions 1 to 4, wherein the medical device in fully-hydrated state has a WBUT of at least about 12.5 seconds.

8. The medical device of any one of inventions 1 to 7, wherein the medical device in fully-hydrated state has a friction rating of about 2.5 or lower.

9. The medical device of any one of inventions 1 to 7, wherein the medical device in fully-hydrated state has a friction rating of about 2 or lower.

10. The medical device of any one of inventions 1 to 7, wherein the medical device in fully-hydrated state has a friction rating of about 1.5 or lower.

11. The medical device of any one of inventions 1 to 7, wherein the medical device in fully-hydrated state has a friction rating of about 1 or lower.

12. The medical device of any one of inventions 1 to 11, wherein $\Delta WBUT_{DS}(i)$ is about 35% or less.

13. The medical device of any one of inventions 1 to 11, wherein $\Delta WBUT_{DS}(i)$ is about 25% or less.

14. The medical device of any one of inventions 1 to 11, wherein $\Delta WBUT_{DS}(i)$ is about 15% or less.

15. The medical device of any one of inventions 1 to 14, wherein the hydrogel coating is thermodynamically stable as characterized by having a $\Delta FR_{DS}(i)$ of about 60% or less.

16. The medical device of any one of inventions 1 to 14, wherein the hydrogel coating is thermodynamically stable as characterized by having a $\Delta FR_{DS}(i)$ of about 50% or less.

17. The medical device of any one of inventions 1 to 14, wherein the hydrogel coating is thermodynamically stable as characterized by having a $\Delta FR_{DS}(i)$ of about 40% or less, even more preferably about 30% or less.

18. The medical device of any one of inventions 1 to 14, wherein the hydrogel coating is thermodynamically stable as characterized by having a $\Delta FR_{DS}(i)$ of about 30% or less.

19. The medical device of any one of inventions 1 to 18, wherein i is an integer of 7 or larger.
20. The medical device of any one of inventions 1 to 18, wherein i is an integer of 14 or larger.
21. The medical device of any one of inventions 1 to 18, wherein i is an integer of 30 or larger.
22. The medical device of any one of inventions 1 to 18, wherein i is an integer of 60 or larger.
23. The medical device of any one of inventions 1 to 22, wherein the hydrogel coating is durable as characterized by having a digital-rubbing-induced reduction in WBUT after j cycles of digital rubbing tests, $\Delta WBUT_{DR}(j)$, of about 45% or less and optionally a digital-rubbing-induced increase in friction rating after j cycles of digital rubbing tests, $\Delta FR_{DR}(j)$, Of about 60% or less, wherein $$\Delta WBUT_{DR}(j) = \frac{WBUT_{0DR} - WBUT_{jDR}}{WBUT_{0DR}} \times 100\% \text{ and}$$

$$\Delta FR_{DR}(j) = \frac{FR_{jDR} - FR_{0DR}}{4} \times 100\%$$

in which $WBUT_{0DR}$ and $FR_{0DR}$ are the WBUT and the friction rating of the medical device which is in fully-hydrated state and is subjected to zero digital rubbing test, and $WBUT_{jDR}$ and $FR_{jDR}$ are the WBUT and the friction rating of the medical device which is in fully hydrated state and has been subjected to at least j cycles of digital rubbing tests, wherein j is an integer of 2.
24. The medical device of invention 23, wherein $\Delta WBUT_{DR}$(j) is about 35% or less.
25. The medical device of invention 23, wherein $\Delta WBUT_{DR}$(j) is about 25% or less.
26. The medical device of invention 23, wherein $\Delta WBUT_{DR}$(j) is about 15% or less.
27. The medical device of any one of inventions 23 to 26, wherein the hydrogel coating is durable as characterized by having a $\Delta FR_{DR}$(j) of about 60% or less.
28. The medical device of any one of inventions 23 to 26, wherein the hydrogel coating is durable as characterized by having a $\Delta FR_{DR}$(j) of about 50% or less.
29. The medical device of any one of inventions 23 to 26, wherein the hydrogel coating is durable as characterized by having a $\Delta FR_{DR}$(j) of about 40% or less.
30. The medical device of any one of inventions 23 to 26, wherein the hydrogel coating is durable as characterized by having a $\Delta FR_{DR}$(j) of about 30% or less.
31. The medical device of any one of inventions 23 to 30, wherein j is an integer of 7.
32. The medical device of any one of inventions 23 to 30, wherein j is an integer of 14.
33. The medical device of any one of inventions 23 to 30, wherein j is an integer of 30.
34. The medical device of any one of inventions 1 to 33, wherein the medical device is a soft contact lens having an oxygen permeability (Dk) of at least about 125 barrers in a fully-hydrated state.
35. The medical device of any one of inventions 1 to 33, wherein the medical device is a soft contact lens having an oxygen permeability (Dk) of at least about 150 barrers in a fully-hydrated state.
36. The medical device of any one of inventions 1 to 33, wherein the medical device is a soft contact lens having an oxygen permeability (Dk) of at least about 175 barrers in a fully-hydrated state.
37. The medical device of any one of inventions 1 to 33, wherein the medical device is a soft contact lens having an oxygen permeability (Dk) of at least about 200 barrers in a fully-hydrated state.
38. The medical device of any one of inventions 34 to 37, wherein the soft contact lens has: an elastic modulus of about 2.0 MPa or less; an averaged water contact angle of about 80 degrees or less; or combinations thereof
39. The medical device of any one of inventions 34 to 38, wherein the soft contact lens has an elastic modulus of from about 0.1 MPa to about 1.5 MPa.
40. The medical device of any one of inventions 34 to 38, wherein the soft contact lens has an elastic modulus of from about 0.2 about 1.2 or less.
41. The medical device of any one of inventions 34 to 38, wherein the soft contact lens has an elastic modulus of from about 0.3 MPa to about 1.0 MPa.
42. The medical device of any one of inventions 34 to 41, wherein the soft contact lens has an averaged water contact angle of about 70 degrees or less.
43. The medical device of any one of inventions 34 to 41, wherein the soft contact lens has an averaged water contact angle of about 60 degrees or less.
44. The medical device of any one of inventions 34 to 41, wherein the soft contact lens has an averaged water contact angle of about 50 degrees or less.
45. The medical device of any one of inventions 1 to 44, wherein the medical device comprises the silicone substrate, a base coating directly on the surface of the silicone substrate, and a hydrogel layer covalently attached onto the base coating.
46. The medical device of invention 45, wherein the base coating comprises a plasma layer which is directly on the surface of the silicone substrate.
47. The medical device of invention 45, wherein the base coating comprises a prime plasma layer and a reactive polymer layer on top of the prime plasma layer, wherein the prime plasma layer is directly on the surface of the silicone substrate and has a thickness of less than about 40 nm, wherein the hydrogel coating comprises the hydrogel layer crosslinked with the reactive polymer layer.
48. The medical device of invention 47, wherein the prime plasma layer has a thickness of from about 1 nm to about 35 nm.
49. The medical device of invention 47, wherein the prime plasma layer has a thickness of from about 2 nm to about 30 nm.
50. The medical device of any one of inventions 1 to 49, wherein the hydrogel coating has a water content of at least about 40% by weight.
51. The medical device of any one of inventions 1 to 49, wherein the hydrogel coating has a water content of at least about 50% (preferably at least about 60%, more preferably at least about 70%, even more preferably at least about 80%) by weight.
52. A method for producing a medical device which includes a silicone substrate and a hydrogel coating thereon, comprising the steps of:
   (1) obtaining a silicone substrate in a dry state, wherein the silicone substrate is made of a crosslinked silicone material;
   (2) subjecting the silicone substrate in the dry state to a surface treatment to form a base coating comprising a prime plasma layer and a reactive polymer layer, wherein the surface treatment comprises the sub-steps of (a) plasma-treating the surface of the silicone substrate in the dry state with a plasma to form the prime plasma layer on the silicone substrate, wherein the prime plasma layer has a thickness of less than about 40 nm, wherein the plasma is generated in a plasma gas (i.e., an atmosphere) composed of air, $CO_2$, or a mixture of a $C_1$-$C_6$ hydrocarbon and a secondary gas selected from the group consisting of air, $CO_2$, $N_2$, and combinations thereof, and (b) contacting the plasma-treated silicone substrate with a first aqueous solution including a reactive hydrophilic polymer to form a reactive polymer layer, wherein the reactive hydrophilic polymer has multiple reactive functional groups selected from the group consisting of carboxyl groups, primary amine groups, secondary amine groups, and combinations thereof; and (3) heating the silicone substrate with the base coating thereon obtained in step (2), in a second aqueous solution which comprises a water-soluble and thermally-crosslinkable hydrophilic polymeric material having azetidinium groups, at a temperature of from about 60° C. to about 140° C. for a time period sufficient long to crosslink the water-soluble thermally-crosslinkable hydrophilic polymeric material and the base coating so as to obtain the medical device which comprises the silicone substrate and a hydrogel coating thereon, wherein the medical device in fully hydrated state has a WBUT of at least about 5 seconds and a friction rating of about 3 or lower, wherein the hydrogel coating is thermodynamically stable as characterized by having a dry-storage-induced reduction in WBUT after i days of dry storage at room temperature, designated as $\Delta WBUT_{DS}(I)$, of about 45% or less and optionally a dry-storage-induced increase in friction rating after i days of dry storage at room temperature, $\Delta FR_{DS}(I)$, of about 60% or less, wherein $$\Delta WBUT_{DS}(i) = \frac{WBUT_{DS@0} - WBUT_{DS@i}}{WBUT_{DS@0}} \times 100\% \text{ and}$$

$$\Delta FR_{DS}(i) = \frac{FR_{DS@i} - FR_{DS@0}}{4} \times 100\%$$

in which $WBUT_{DS@0}$ and $FR_{DS@0}$ are the WBUT and the friction rating of the medical device in fully-hydrated state at day zero of dry storage and are determined before the medical device is dehydrated and stored in air at room temperature, and $WBUT_{DS@i}$ and $FR_{DS@i}$ are the WBUT and the friction rating of the medical device in fully hydrated state at/days of dry storage and are determined after the medical device has been fully dehydrated and stored in air at room temperature for at least/days and then has been fully rehydrated before determining the WBUT and the friction rating, wherein i is an integer of 2 or larger.

53. The method of invention 52, wherein the medical device is an ophthalmic device.

54. The method of invention 53, wherein the ophthalmic device is an intraocular lens, a stent, a device under eyelids, a corneal onlay, a glaucoma shunt, or an implant.

55. The method of invention 52, wherein the medical device is a soft contact lens.

56. The method of any one of inventions 52 to 55, wherein the prime plasma layer has a thickness of from about 1 nm to about 35 nm.

57. The method of any one of inventions 52 to 55, wherein the prime plasma layer has a thickness of from about 2 nm to about 30 nm.

58. The method of any one of inventions 52 to 57, wherein the plasma gas is composed of air.

59. The method of any one of inventions 52 to 57, wherein the plasma gas is compose of $CO_2$.

60. The method of any one of inventions 52 to 57, wherein the plasma gas is compose of a mixture of a $C_1$-$C_6$ hydrocarbon and a secondary gas selected from the group consisting of air, $CO_2$, $N_2$, and combinations thereof.

61. The method of any one of inventions 52 to 57, wherein the plasma gas is composed of a mixture of a $C_1$-$C_4$ hydrocarbon and a secondary gas selected from the group consisting of air, $CO_2$, $N_2$, and combinations thereof.

62. The method of any one of inventions 52 to 57, wherein the plasma gas is composed of a mixture of methane and a secondary gas selected from the group consisting of air, $CO_2$, $N_2$, and combinations thereof.

63. The method of any one of inventions 60 to 62, wherein the secondary gas is air or $CO_2$.

64. The method of any one of inventions 52 to 63, wherein the reactive hydrophilic polymer has multiple carboxyl groups.

65. The method of any one of inventions 52 to 63, wherein the water-soluble and thermally-crosslinkable hydrophilic polymeric material has amino or carboxyl groups.

66. The method of any one of inventions 52 to 65, wherein the medical device in fully hydrated state has a WBUT of at least about 7.5 seconds.

67. The method of any one of inventions 52 to 65, wherein the medical device in fully hydrated state has a WBUT of at least about 10 seconds.

68. The method of any one of inventions 52 to 65, wherein the medical device in fully hydrated state has a WBUT of at least about 12.5 seconds.

69. The method of any one of inventions 52 to 69, wherein the medical device in fully hydrated state has a friction rating of about 2.5 or lower.

70. The method of any one of inventions 52 to 69, wherein the medical device in fully hydrated state has a friction rating of about 2 or lower.

71. The method of any one of inventions 52 to 69, wherein the medical device in fully hydrated state has a friction rating of about 1.5 or lower.

72. The method of any one of inventions 52 to 69, wherein the medical device in fully hydrated state has a friction rating of about 1 or lower.

73. The method of any one of inventions 52 to 72, wherein the $\Delta WBUT_{DS}(i)$ is about 35% or less.

74. The method of any one of inventions 52 to 72, wherein the $\Delta WBUT_{DS}(i)$ is about 25% or less.

75. The method of any one of inventions 52 to 72, wherein the $\Delta WBUT_{DS}(i)$ is about 15% or less.

76. The method of any one of inventions 52 to 75, wherein the hydrogel coating is thermodynamically stable as characterized by having a $\Delta FR_{DS}(i)$ of about 60% or less.

77. The method of any one of inventions 52 to 75, wherein the hydrogel coating is thermodynamically stable as characterized by having a $\Delta FR_{DS}(i)$ of about 50% or less.

78. The method of any one of inventions 52 to 75, wherein the hydrogel coating is thermodynamically stable as characterized by having a $\Delta FR_{DS}(i)$ of about 40% or less.

79. The method of any one of inventions 52 to 75, wherein the hydrogel coating is thermodynamically stable as characterized by having a $\Delta FR_{DS}(i)$ of about 30% or less.

80. The method of any one of inventions 52 to 79, wherein i is an integer of 7 or larger.
81. The method of any one of inventions 52 to 79, wherein i is an integer of 14 or larger.
82. The method of any one of inventions 52 to 79, wherein i is an integer of 30 or larger, even more preferably 60 or larger.
83. The method of any one of inventions 52 to 79, wherein i is an integer of 60 or larger.
84. The method of any one of inventions 52 to 83, wherein the surface treatment further comprises, prior to substep (2)(a), a substep of plasma-pretreating the surface of the silicone substrate in the dry state with a plasma generated in a plasma gas composed of air.
85. The method of any one of inventions 52 to 84, wherein the plasma treated silicone substrate is placed in contact with the first aqueous solution within a time period of about 40 minutes or less immediately after the plasma-treatment sub-step and before contacting with water, an organic solvent, a mixture of water and one or more organic solvents, a mixture of two or more organic solvent, or any aqueous or organic-based solution free of any reactive polymer.
86. The method of any one of inventions 52 to 84, wherein the plasma treated silicone substrate is placed in contact with the first aqueous solution within a time period of about 30 minutes or less immediately after the plasma-treatment sub-step and before contacting with water, an organic solvent, a mixture of water and one or more organic solvents, a mixture of two or more organic solvent, or any aqueous or organic-based solution free of any reactive polymer.
87. The method of any one of inventions 52 to 84, wherein the plasma treated silicone substrate is placed in contact with the first aqueous solution within a time period of about 20 minutes or less immediately after the plasma-treatment sub-step and before contacting with water, an organic solvent, a mixture of water and one or more organic solvents, a mixture of two or more organic solvent, or any aqueous or organic-based solution free of any reactive polymer.
88. The method of any one of inventions 52 to 87, wherein the reactive hydrophilic polymer is a polyanionic polymer comprising carboxyl groups and having a weight average molecular weight of at least 1000 Daltons (preferably from 2000 to 5,000,000 Daltons, more preferably from 5000 to 2,000,000 Daltons, even more preferably from 10,000 to 1,000,000 Daltons).
89. The method of invention 88, wherein the first aqueous solution has a pH from about 1.0 to about 3.0 (preferably from about 1.5 to about 2.5, more preferably from about 1.8 to about 2.0).
90. The method of invention 88 or 89, wherein the polyanionic polymer is selected from the group consisting of polyacrylic acid, polymethacrylic acid, polyethylacrylic acid, poly(acrylic acid-co-methacrylic acid), poly(acrylic acid-co-ethacrylic acid), poly(methacrylic acid-co-ethacrylic acid), and a mixture thereof (more preferably is selected from the group consisting of polyacrylic acid, polymethacrylic acid, poly(acrylic acid-co-methacrylic acid), and a mixture thereof).
91. The method of any one of inventions 52 to 87, wherein the reactive hydrophilic polymer is a polycationic polymer comprising primary and/or secondary amino groups and having a weight average molecular weight of at least 1000 Daltons (preferably from 2000 to 5,000,000 Daltons, more preferably from 5000 to 2,000,000 Daltons, even more preferably from 10,000 to 1,000,000 Daltons).
92. The method of invention 91, wherein the first aqueous solution has a pH from about 9.5 to about 11.0 (preferably from about 10.0 to about 11.0).
93. The method of invention 91 or 92, wherein the polycationic polymer is selected from the group consisting of polyethyleneimine, polyallylamine, polyvinylamine, polyamidoamine, and a mixture thereof.
94. The method of any one of inventions 52 to 87, wherein the reactive hydrophilic polymer comprises azetidinium groups and reactive functional groups selected from the group consisting of primary groups, secondary amino groups, carboxyl groups, and combinations thereof, wherein the reactive hydrophilic polymer has a weight average molecular weight of at least 1000 Daltons (preferably from 2000 to 5,000,000 Daltons, more preferably from 5000 to 2,000,000 Daltons, even more preferably from 10,000 to 1,000,000 Daltons).
95. The method of invention 94, wherein the first aqueous solution has a pH of less than about 8.0 (more preferably from about 2.0 to about 8.0, even more preferably from about 6.0 to about 8.0).
96. The method of any one of invention 94 or 95, wherein the reactive hydrophilic polymer is a poly(2-oxazoline-co-ethyleneimine)-epichlorohydrin, a chemically-modified poly(2-oxazoline-co-ethyleneimine)-epichlorohydrin, a chemically-modified polyamidoamine-epichlorohydrin, or combinations thereof, wherein the chemically-modified poly(2-oxazoline-co-ethyleneimine)-epichlorohydrin or the chemically-modified polyamidoamine-epichlorohydrin comprises (i) from about 20% to about 95% by weight of first polymer chains derived from a polyamidoamine-epichlorohydrin or a poly(2-oxazoline-co-ethyleneimine)-epichlorohydrin, (ii) from about 5% to about 80% by weight of hydrophilic moieties or second polymer chains derived from at least one hydrophilicity-enhancing agent having at least one reactive functional group selected from the group consisting of amino group, carboxyl group, thiol group, and combination thereof, wherein the hydrophilic moieties or second polymer chains are covalently attached to the first polymer chains through one or more covalent linkages each formed between one azetitdinium group of the polyamidoamine-epichlorohydrin or the poly(2-oxazoline-co-ethyleneimine)-epichlorohydrin and one amino, carboxyl or thiol group of the hydrophilicity-enhancing agent, and (iii) azetidinium groups which are parts of the first polymer chains or pendant or terminal groups covalently attached to the first polymer chains.
97. The method of any one of inventions 52 to 96, wherein the water-soluble thermally crosslinkable hydrophilic polymeric material is a poly(2-oxazoline-co-ethyleneimine)-epichlorohydrin, a chemically-modified poly (2-oxazoline-co-ethyleneimine)-epichlorohydrin, a chemically-modified polyamidoamine-epichlorohydrin, or combinations thereof, wherein the chemically-modified poly(2-oxazoline-co-ethyleneimine)-epichlorohydrin or the chemically-modified polyamidoamine-epichlorohydrin comprises (i) from about 20% to about 95% by weight of first polymer chains derived from a polyamidoamine-epichlorohydrin or a poly(2-oxazoline-co-ethyleneimine)-epichlorohydrin, (ii) from about 5% to about 80% by weight of hydrophilic moieties or second polymer chains derived from at least one hydrophilicity-enhancing agent having at least one reactive functional group selected from the group consisting of amino group, carboxyl group, thiol group, and combination thereof, wherein the hydrophilic moieties or second polymer chains are covalently attached to the first polymer chains through one or more covalent linkages each formed between one azetitdinium group of the polyamidoamine-epichlorohydrin or the poly(2-oxazoline-co-ethyl-eneimine)-epichlorohydrin and one amino, carboxyl or thiol group of the hydrophilicity-enhancing agent, and (iii) azetidinium groups which are parts of the first polymer chains or pendant or terminal groups covalently attached to the first polymer chains.

98. The method of any one of invention 52 to 97, wherein the step of heating is carried out directly in a sealed lens package containing a packaging solution including the water-soluble and thermally-crosslinkable hydrophilic polymeric material during sterilization by autoclave at a temperature from about 115° C. to about 125° C. for at least about 20 minutes under pressure; wherein the packaging solution comprises from about 0.01% to about 2% by weight of the water-soluble and thermally-crosslinkable hydrophilic polymeric material; wherein the packaging solution comprises at least one buffering agent in an amount sufficient to maintain a pH of from about 6.0 to about 8.5 and has a tonicity of from about 200 to about 450 milliosmol (mOsm) and a viscosity of from about 1 centipoise to about 5 centipoises, at 25° C.

99. The method of any one of inventions 52 to 98, wherein the hydrogel coating is durable as characterized by having a digital-rubbing-induced reduction in WBUT after j cycles of digital rubbing tests, $\Delta WBUT_{DR}(j)$, of about 45% or less and optionally a digital-rubbing-induced increase in friction rating after j cycles of digital rubbing tests, $\Delta FR_{DR}(J)$, of about 60% or less, wherein $$\Delta WBUT_{DR}(j) = \frac{WBUT_{0DR} - WBUT_{jDR}}{WBUT_{0DR}} \times 100\% \text{ and}$$

$$\Delta FR_{DR}(j) = \frac{FR_{jDR} - FR_{0DR}}{4} \times 100\%$$

in which $WBUT_{0DR}$ and $FR_{0DR}$ are the WBUT and the friction rating of the medical device which is in fully-hydrated state and is subjected to zero digital rubbing test, and $WBUT_{jDR}$ and $FR_{jDR}$ are the WBUT and the friction rating of the medical device which is in fully hydrated state and has been subjected to at least j cycles of digital rubbing tests, wherein j is an integer of 2.

100. The method of invention 99, wherein $\Delta WBUT_{DR}(j)$ is about 35% or less, preferably about 25% or less, more preferably about 15% or less.

101. The method of invention 99 or 100, wherein the hydrogel coating is durable as characterized by having a $\Delta FR_{DR}(I)$ of about 60% or less, preferably about 50% or less, more preferably about 40% or less, even more preferably about 30% or less.

102. The method of any one of inventions 99 to 101, wherein j is an integer of 7, preferably 14, more preferably 30.

The previous disclosure will enable one having ordinary skill in the art to practice the invention. Various modifications, variations, and combinations can be made to the various embodiment described herein. In order to better enable the reader to understand specific embodiments and the advantages thereof, reference to the following examples is suggested. It is intended that the specification and examples be considered as exemplary.

Example 1

Oxygen Permeability Measurements

The apparent oxygen permeability ($Dk_{app}$), the apparent oxygen transmissibility (Dk/t), the intrinsic (or edge-corrected) oxygen permeability ($Dk_c$) of a lens and a lens material are determined according to procedures described in Example 1 of U.S. patent application publication No. 2012/0026457 A1 (herein incorporated by reference in its entirety).

Digital Rubbing Tests.

The lenses are digitally rubbed (wearing disposable powder-free latex gloves) with RENU® multi-purpose lens care solution (or another multi-purpose lens care solution) for 20 seconds and then rinsed with saline. The above procedure is repeated for a given times, e.g., from 1 to 30 times, (i.e., number of repetitions of digital rubbing tests which imitate cleaning and soaking cycles).

Lubricity Evaluation.

The lubricity of a lens is evaluated by using a finger-felt lubricity test which characterizes qualitatively the slipperiness of a lens surface on a friction rating scale of from 0 to 4. The higher the friction rating is, the lower the slipperiness (or lubricity).

Commercial lenses: DAILIES® TOTAL1®; ACUVUE® OASYS™; ACUVUE® ADVANCE PLUS™; DAILIES® Aqua Comfort Plus®; and AIR OPTIX®, are assigned a friction rating (designated "FR" hereinafter) of 0, 1, 2, 3, and 4 respectively. They are used as standard lenses for determining the friction rating a lens under test.

The samples are placed in PBS for at least two rinses of 30 minutes each and then transferred to fresh PBS before the evaluation. Before the evaluation, hands are rinsed with a soap solution, extensively rinsed with DI water and then dried with KimWipe® towels. The samples are handled between the fingers and a numerical number is assigned for each sample relative to the above standard lenses described above. For example, if lenses are determined to be only slightly better than AIR OPTIX® lenses, then they are assigned a number 3. The value of a friction rating is one obtained by averaging the results of at least two friction ratings of a contact lens by two or more persons and/or by averaging the friction ratings of two or more contact lenses (from the identical batch of lens production) by one person.

Surface Wettability Tests.

Water contact angle (WCA) on a contact lens is a general measure of the surface wettability of a contact lens. In particular, a low water contact angle corresponds to more wettable surface. Average contact angles (Sessile Drop) of contact lenses are measured using a VCA 2500 XE contact angle measurement device from AST, Inc., located in Boston, Mass. This equipment is capable of measuring advancing contact angles ($\theta_a$) or receding contact angles ($\theta_r$) or sessile (static) contact angles. Unless specified, water contact angle is sessile (static) contact angle. The measurements are performed on fully hydrated contact lenses and immediately after blot-drying as follows. A contact lens is removed from the vial and washed 3 times in ~200 ml of fresh DI water in order to remove loosely bound packaging additives from the lens surface. The lens is then placed on top of a lint-free clean cloth (Alpha Wipe TX1009), dabbed well to remove surface water, mounted on the contact angle measurement pedestal, blown dry with a blast of dry air and finally the sessile drop contact angle is automatically measured using the software provided by the manufacturer. The DI water used for measuring the contact angle has a resistivity >18MΩcm and the droplet volume used is 2 μl.

Typically, uncoated silicone hydrogel lenses (after autoclave) have a sessile drop contact angle around 120 degrees. The tweezers and the pedestal are washed well with Isopropanol and rinsed with DI water before coming in contact with the contact lenses.

Water Break-Up Time (WBUT) Tests.

The surface hydrophilicity of lenses (after autoclave) is assessed by determining the time required for the water film to start breaking on the lens surface. Briefly, lenses are removed from the vial and placed in PBS (phosphate buffered saline) for at least two rinses of 30 minutes each and then transferred to fresh PBS in order to remove loosely bound packaging additives from the lens surface. The lens is removed from the solution and held against a bright light source. The time that is needed for the water film to break (de-wet) exposing the underlying lens material is noted visually. Uncoated lenses typically instantly break upon removal from PBS and are assigned a WBUT of 0 seconds. Lenses exhibiting WBUT >10 seconds are considered to have a hydrophilic surface and are expected to exhibit adequate wettability (ability to support the tear film) on-eye.

Coating Intactness Tests.

The intactness of a coating on the surface of a contact lens can be tested according to Sudan Black stain test as follow. Contact lenses with a coating (an LbL coating, a plasma coating, or any other coatings) are dipped into a Sudan Black dye solution (Sudan Black in vitamin E oil). Sudan Black dye is hydrophobic and has a great tendency to be adsorbed by a hydrophobic material or onto a hydrophobic lens surface or hydrophobic spots on a partially coated surface of a hydrophobic lens (e.g., silicone hydrogel contact lens). If the coating on a hydrophobic lens is intact, no staining spots should be observed on or in the lens. All of the lenses under test are fully hydrated.

X-Ray Photoelectron Spectrophotometer (XPS) Tests.

This analytical technique uses x-rays to excite the electrons associated with the atoms at the lens surface. Then collects a portion of the energy emitted by the excited electrons through
which analytical information is derived and used to determine the chemical concentrations of elements found at the surface.

XPS is carried out using Sage HR100 spectrometer using a Mg K-alpha XR-50 broad X-ray source (10 kV, 100 W) and a 100 mm PHOIBOS analyzer.

PHMB Uptaking Test.

The preservative polyhexamethylene biguanide hydrochloride (PHMB HCl) in solution is measured by the method of High Performance Liquid Chromatography (HPLC). This method may be used specifically for the analysis of PHMB at low ppm levels in Optifree Replenish, Renu fresh multipurpose, PureMoist and in citrate buffered release solutions.

The PHMB test is carried out using the instrument of Waters H-Class UPLC with Dionex Corona Ultra RS UHPLC detector, with HPLC Columnof Jupiter Widepore 300A C18. To prepare uptake test sample, one lens will be soaked in 5.0 ml Renu Fresh, in 30 ml PP bottle, for 24 hours at room temperature. The difference of HPLC tests between uptake solution and control Renu solution indicates the PHMB uptake per lens (µg/lens).

Lens Surface FSI Test.

Front Surface Imperfection (FSI) test is the Tork Debris Adhesion Evaluation.

The Tork Debris Adhesion Evaluation method is used to differentiate the amount of debris left behind on contact lenses after exposure to hands washed and then dried with Tork Premium paper towels. The data generated from this method serve as an informational tool to assess the relative susceptibility of the lens to the adherence of non-specific debris from the Tork towels. The method does not set or imply specifications for pass/fail or acceptable/unacceptable levels of debris adhesion. This method is qualitative and is intended for evaluating development lenses only.

The debris adhesion rating scale is a five point scale with integer values from 0 and 4. 0 is the best rating. 4 is the worst rating. Contact lenses coated with PAA/1-PrOH and handled with hands washed and then dried with the Tork Premium paper towels are generally representative of level 4 debris adhesion. The rating scale is correlated with the number of large globular like particles on a lens's surface. As the number of particles on a lens increases the debris adhesion grade of that lens increases. Lenses exhibiting FSI=0-1 are considered better and are expected to exhibit no extra negative charge on lens surface.

Lens Surface Cracking Test.

The lens surface cracking test is used to differentiate the severity of surface cracking resulting from exposure of a lens to conditions and forces that could be encountered during routine and intended use of lenses. The data generated from this method serve as an informational tool. The method does not set or imply specifications for pass/fail or acceptable/unacceptable levels of surface cracking. This method is qualitative and is intended for evaluating development lenses only.

Invert the lens confirmation by holding the edge of the lens between the thumb and index finger of one hand. The concave side of the lens should face the experimenter's body. With the thumb and/or index finger of the other hand, gently bend the top of the lens over the index finger holding the lens until the lens confirmation inverts. Look for surface cracks at 10× magnification under the darkfield stereomicroscope. If individual crack lines are clearly distinguishable, the lens receives a grade of 2. If the lens appears to have long, cloudy, linear formations, but crack lines are not distinguishable, inspect these areas at magnification up to 60×. If crack lines are distinguishable, the lens receives a grade of 1. If no crack lines or long, cloudy, linear formations are visible, the lens receives a grade of 0. Lenses exhibiting cracking level=0 are considered better and are expected to exhibit smooth and soft surface.

Lens Surface Bead Test.

The lens surface bead test is used to evaluate surface charges of contact lenses. The data generated from this method are the numbers of beads that are absorbed onto lens surface, and serve as an informational tool indicating the surface charge property. The method does not set or imply specifications for pass/fail or acceptable/unacceptable levels of surface charge. This method is qualitative and is intended for evaluating development lenses only.

The beads of Dovex 1×4 chloride form 50-100 mesh (Lot#54898PJV Sigma Aldrich CAS69011-19-4) are suspended in PBS. The lens is soaked in bead/PBS in a centrifuge tube. After on shaker at 300 rpm for 2 min, the lens is rinsed using PBS. The beads absorbed on lens surface are then observed under the dark field microscope. Image Pro software is used to analyze the total count number of cationic beads. The total for cationic beads is the total count number of the bead test.

Example 2

Soft silicone contact lenses are produced by photopolymerization of a polymerizable silicone composition in plastic molds. A clear composition is prepared to have 99% by weight of α,ω-bis(diacrylamidopropyl)-polydimethylsiloxane (Mw~7500) and 1% by weight of a photoinitiator Darocur® 1173 (Ciba). The prepared composition is introduced in polypropylene contact lens molds (+6.00 D) and irradiated with a UV radiation at an intensity of about 16 mW/cm², which is from a Hamamatsu UV Lamp with a 330 nm cut-off filter after the condenser unit, for about 30 seconds. The molded silicone contact lenses (or silicone rubber contact lenses) are extracted with Methyl Ethyl Ketone (MEK) for 6 minutes and then hydrated in water. The lenses are packed in PBS for autoclaving. The hydrated contact lenses are determined to have the following properties: an oxygen permeability (Dk) of ~1105 barrers; non-detectable ion permeability; an elastic modulus (Young's modulus) of about 1.46 MPa; an elongation at break of about 164%; a diameter of 14.49 mm, a water content of about 1.02% by weight, and a swelling ratio of 52% in toluene.

Example 3

A clear polymerizable silicone composition is prepared to have 75% by weight of α,ω-bis(diacrylamidopropyl)-polydimethylsiloxane (Mw~7500), 24% by weight of 1-propanol, and 1% by weight of a photoinitiator Darocur® 1173 (Ciba). Soft silicone contact lenses are produced by photopolymerization of the prepared composition in plastic molds according to the procedures described in Example 2. The prepared composition is introduced in polypropylene contact lens molds (+6.00 D) and irradiated with a UV radiation at an intensity of about 16 mW/cm², which is from a Hamamatsu UV Lamp with a 330 nm cut-off filter after the condenser unit, for about 1.5 minutes. The molded silicone contact lenses (or silicone rubber contact lenses) are extracted with MEK for 6 minutes and then hydrated in water. The lenses are packed in PBS for autoclaving. The hydrated silicone contact lenses are determined to have the following properties: an oxygen permeability (Dk) is greater than 1000 barrers (beyond the upper measurement limit of the instrument); non-detectable ion permeability; an elastic modulus (Young's modulus) of about 0.83 MPa; an elongation at break of about 197%; a diameter of 13.03 mm, a water content of about 1.16% by weight, and a swelling ratio of 44% in toluene.

Example 4

Various polymerizable silicone compositions listed in Table 1 are prepared from the following components: Am-PDMS-Am: α,ω-bis(diacrylamidopropyl)-polydimethylsiloxane (Mw~7500); MRS-044: (methacryloxypropyl)methylsiloxane; Tris-Am: N-[tris(trimethylsiloxy)-silylpropyl] acrylamide; MA-PEG-OCH₃ 480: polyethylene glycol methyl ether methacrylate (Mw~480); MA-PEG-OH 360: polyethylene glycol methacrylate (Mw~360); 1-PrOH: 1-propanol.

TABLE 1

| | Composition No. | | | | | |
| --- | --- | --- | --- | --- | --- | --- |
| | 5-0 | 5-1 | 5-2 | 5-3 | 5-4 | 5-5 |
| Am-PDMS-Am 7500 | 75% | 64% | 37.5% | 56% | 74% | 74% |
| MRS-044 | — | 11% | 37.5% | — | — | — |
| Tris-Am | — | — | — | 19% | — | — |
| MA-PEG-OCH₃ 480 | — | — | — | — | 1% | — |
| MA-PEG-OH 360 | — | — | — | — | — | 1% |

TABLE 1-continued

| | Composition No. | | | | | |
| --- | --- | --- | --- | --- | --- | --- |
| | 5-0 | 5-1 | 5-2 | 5-3 | 5-4 | 5-5 |
| 1-PrOH | 24% | 24% | 24% | 24% | 24% | 24% |
| Darocur 1173 | 1% | 1% | 1% | 1% | 1% | 1% |

Soft contact lenses are produced by photopolymerization of a composition in plastic molds according to the procedures described in Example 3. The molded silicone contact lenses are extracted with MEK for 6 minutes and then hydrated in water. The lenses are packed in PBS for autoclaving. The hydrated silicone contact lenses are determined to have an oxygen permeability of greater than 1000 barrers (beyond the upper measurement limit of the instrument), a non-detectable ion permeability (below the detection limit), and other properties reported in Table 2.

TABLE 2

| | Lenses molded from Composition No. | | | | | |
| --- | --- | --- | --- | --- | --- | --- |
| Properties | 5-0 | 5-1 | 5-2 | 5-3 | 5-4 | 5-5 |
| Elastic modulus (MPa) | 0.83 | 0.75 | 0.72 | 0.71 | 0.78 | 0.67 |
| Elongation at break | 197% | 168% | 182% | 241% | 203% | 272% |
| Diameter (mm) | 13.03 | 12.89 | 13.05 | 13.06 | 13.07 | 13.12 |
| % H₂O | 1.16 | 1.6 | 3.5 | 13.1 | 1.9 | 2.1 |
| Swelling ratio in 2-propanol | 9% | 14% | 13% | 12% | 13% | 14% |
| Swelling ratio in MEK | 19% | 24% | 33% | 30% | 32% | 30% |
| Swelling ratio in toluene | 44% | 52% | 56% | 52% | 63% | 62% |

MEK: methyl ether ketone.
Swelling ratio = (lens diameter in a solvent − lens diameter in dry state)/lens diameter in dry state.

The PAA dip coating treatment is carried out as follows. Dip lenses in PAA/1-Propanol solution (acidified with formic acid to pH=2) for 44 seconds after MEK (6 min) extraction. The PAA powder is purchased from Lubrizol with Mw around 1 million. The PAA coated lenses are hydrated in 1-Propanol with 50% DI water for 78 seconds before transferring in pure DI water.

The plasma coating is a plasma-assisted reactive process. The plasma is a partially ionized gas containing ions, electrons, atoms, neutrals. To enable the gas to be ionized in a controlled and qualitative manner, the process is carried out under vacuum conditions. A vacuum chamber of a rotary plasma treatment system is first pumped down via rotary vacuum pump system to an absolute vacuum pressure 100 to 0 pa., the gas is then introduced into the chamber by means of mass flow control valves, pressure is monitored by the vacuum diapharm gauge, measured pressure is converted to electrical voltage. Power across the electrodes is between 20 to 50 watts (power is preferably at 30 watts); Current is between 100 mA±10 mA (current set at 100 mA); Frequency set at 15 kHz for a good coating cycle="SI wafer thickness~240 Å±60 Å"; Voltage is based on the current setting and the material inside chamber. For example:

Regular plasma coating (CH₄/Air) voltage is around 345 to 350 volt

Air only plasma coating voltage is around 365 to 370 volt

PAA dip coating after plasma coating is to look for lens lubricity enhancement.

After the plasma coating, the lenses are transferred into 1 mM PAA aqueous (Mw=1 million of PAA) with pH=2 for 20 min. After the rinse of lenses in PBS, the lenses are then packed in PBS for autoclaving.

The PAA dip coating, plasma coating, PAA dip coating after plasma coating, which give results reported in Table 3. All the lenses have been packed in PBS for autoclaving.

TABLE 3

|  | 5-0 | 5-1 | 5-2 | 5-3 | 5-4 | 5-5 |
|---|---|---|---|---|---|---|
| Lens w/o any surface treatment | | | | | | |
| WBUT (s) | 0 | 0 | 0 | 0 | 0 | 0 |
| FR | 5 | 5 | 5 | 5 | 5 | 5 |
| WCA (°) | 111 | 108 | 113 | 108 | 118 | 118 |
| Lens subjected to PAA dip-coating treatment | | | | | | |
| WBUT (s) | 0 | 0 | 0 | 0 | 0 | 0 |
| FR | 5 | 5 | 5 | 5 | 5 | 5 |
| WCA (°) | 108 | 114 | 110 | 112 | 112 | 105 |
| Lens subjected to $CH_4$/Air plasma treatment | | | | | | |
| WBUT (s) | 0+ | 0+ | 0+ | 1 | 3 | 3 |
| FR | 5 | 5 | 5 | 5 | 5 | 5 |
| WCA (°) | 43 | 47 | 56 | 42 | 46 | 64 |
| Lens subjected to $CH_4$/Air plasma treatment + immediate PAA dip-coating | | | | | | |
| WBUT (s) | 1 | 2 | 1 | 3 | 4 | 4 |
| FR | 3-4 | 3-4 | 4-5 | 2-3 | 2-3 | 2-3 |

Results in Table 3 show that plasma treatment is effective in increasing the wettability (i.e., as shown by decrease in water contact angle) and slightly enhancing the surface hydrophilicity while being ineffective in improving the lubricity. The results also indicates that no PAA coating can be formed directly on silicone contact lenses; but PAA coating may be formed on a plasma coating or layer on the surface of a silicone contact lens.

Example 5

IPC Saline

Poly(AAm-co-AA)(90/10) partial sodium salt (~90% solid content, poly(AAm-co-AA) 90/10, Mw~200,000) is purchased from Polysciences, Inc. and used as received. PAE (Kymene, an azetidinium content of 0.46 assayed with NMR) is purchased from Ashland as an aqueous solution and used as received. An in-package-crosslinking (IPC) saline is prepared by dissolving about 0.07% w/w of poly(AAm-co-AA)(90/10) and about 0.15% of PAE (an initial azetidinium millimolar equivalents of about 8.8 millimole) in phosphate buffered saline (PBS) (about 0.044 w/w % $NaH_2PO_4.H_2O$, about 0.388 w/w/% $Na_2HPO_4.2H_2O$, about 0.79 w/w % NaCl) and adjusting the pH to 7.2-7.4. Then the IPC saline is heat pre-treated for about 6 hours at about 60° C. (heat pretreatment). During this heat pretreatment, poly(AAm-co-AA) and PAE are partially crosslinked to each other (i.e., not consuming all azetidinium groups of PAE) to form a water-soluble and thermally-crosslinkable hydrophilic polymeric material containing azetidinium groups within the branched polymer network in the IPC saline. After the heat pre-treatment, the IPC saline is filtered using a 0.22 micron PES membrane filter and cooled down back to room temperature. 5 ppm hydrogen peroxide is then added to the final IPC saline to prevent bioburden growth and the IPC saline is filtered using a 0.22 micron PES membrane filter.

PAA Solution

Polyacrylic acid (PAA) (from Lubrizol with Mw around 1 million) is used to prepare an aqueous solution of PAA (0.1 mM, pH 2). PAA powder is carefully added in water with vigorously stirring at room temperature for 24 hours. The pH of the PAA solution is adjusted by hydrochloric acid (37% from Fluka-318949).

Surface Treatment

Silicone contact lenses prepared in Example 3 are subjected to the following surface treatments. Lenses are extracted with MEK for 6 minutes and then hydrated in water for minimum 10 min. Then the lenses are individually transferred to the dry tray and vacuum dried at 105° C. for minimum 2 hours before plasma coating.

ST1a: $CH_4$/Air Plasma→Treated-Quenched with Water→Packaged/Autoclaved in Buffered Saline The dried lenses are $CH_4$/Air Plasma-treated by rotary plasma process, using the gas of the mixture of $CH_4$/Air=2:1 in the plasma chamber. After loading the lenses in the plasma chamber, the chamber is first pumped down via rotary vacuum pump system to an absolute vacuum pressure 100 to 0 pa for 90 min. The plasma gases are then introduced into the chamber by means of 2.0 sccm (flow unit: standard cubic centimeters per minute) and 1.0 sccm for $CH_4$ and Air respectively. The plasma coating time is 11 min. Power across the electrodes is between 20 to 50 watts (power is at optimum at 30 watts); Current is 100 mA±10 mA (current set at 100 mA); Frequency set at 15 kHz; Voltage is based on the current setting, around 345 to 350 volt for $CH_4$/Air Plasma treatment.

After the plasma treatment, the plasma coated lenses are quickly (<60 s) transferred into water for hydration with 20 min, which is called that "lens is quenched with water". The lenses are then packed in a Corona treated shell with PBS for autoclave at 120° C. for 45 min.

ST1b: $CH_4$/Air Plasma-Treated→Quenched with Water→Packaged/Autoclaved in IPC Saline The surface treatment ST1b differs from ST1a only in the packaging solution: PBS in ST1a vs the IPC saline in ST1b.

ST1c: $CH_4$/Air Plasma-Treated→Quenched with PAA→Packaged/Autoclaved in Buffered Saline The surface treatment ST1c differs from ST1a only in the quenching solution: water in ST1a vs the PAA solution in ST1c.

ST1d: $CH_4$/Air Plasma-Treated→Quenched with PAA→Packaged/Autoclaved in IPC Saline The surface treatment ST1b differs from ST1a only in the quenching solution (water in ST1a vs PAA in ST1d) and in the packaging solution (PBS in ST1a vs IPC saline in ST1d).

ST2a: Air Plasma-Treated→Quenched with Water→Packaged/Autoclaved in Buffered Saline The dried lenses are Air Plasma-treated by rotary plasma process, using the gas of air only in the plasma chamber. To avoid any contamination of leftover methane in the line, a leak test is a must. It is carried out by setting the flow rate of methane at 0.0 sccm and then pumping down the plasma chamber via rotary vacuum pump system for minimum 15 min.

After loading the lenses in the plasma chamber, the chamber is then pumped down via rotary vacuum pump system to an absolute vacuum pressure 100 to 0 pa for 90 min. The plasma gas, air, is then introduced into the chamber by means of 0.0 sccm and 3.0 sccm for $CH_4$ and Air respectively. The plasma coating time is 11 min. Power across the electrodes is between 20 to 50 watts (power is at optimum at 30 watts); Current is 100 mA±10 mA (current set at 100 mA); Frequency set at 15 kHz; Voltage is based on the current setting, around 365 to 370 volt for Air only plasma treatment.

After the Air plasma treatment, the plasma coated lenses are quickly (<60 s) transferred into water for hydration with 20 min. The lenses are then packed in a Corona treated shell with PBS for autoclave at 120° C. for 45 min.

ST2b: Air Plasma-Treated→Quenched with Water→Packaged/Autoclaved in IPC Saline

The surface treatment ST2b differs from ST2a only in the packaging solution: PBS in ST2a vs the IPC saline in ST2b.

ST2c: Air Plasma-Treated→Quenched with PAA→Packaged/Autoclaved in Buffered Saline The surface treatment ST2c differs from ST2a only in the quenching solution: water in ST2a vs the PAA solution in ST2c.

ST2d: Air Plasma-Treated→Quenched with PAA→Packaged/Autoclaved in IPC Saline

The surface treatment ST2d differs from ST2a only in the quenching solution (water in ST2a vs PAA in ST2d) and in the packaging solution (PBS in ST2a vs IPC saline in ST2d).

ST3a: O2 Plasma-Treated→Quenched with Water→Packaged/Autoclaved in Buffered Saline The surface treatment ST3a differs from ST2a only in the plasma gas (Air in ST2a vs $O_2$ in ST3a) and in the packaging solution (PBS in ST2a vs IPC saline in ST2d).

ST3b: $O_2$ Plasma-Treated→Quenched with Water→Packaged/Autoclaved in IPC Saline The surface treatment ST3b differs from ST3a only in the packaging solution: PBS in ST3a vs the IPC saline in ST3b.

ST3c: $O_7$ Plasma-Treated→Quenched with PAA→Packaged/Autoclaved in Buffered Saline The surface treatment ST3c differs from ST3a only in the quenching solution: water in ST3a vs the PAA solution in ST3c.

ST3d: $O_2$ Plasma-Treated→Quenched with PAA→Packaged/Autoclaved in IPC Saline

The surface treatment ST3d differs from ST3a only in the quenching solution (water in ST3a vs PAA in ST3d) and in the packaging solution (PBS in ST3a vs IPC saline in ST3d).

ST4a: Air Plasma-Pretreated→$CH_4$/Air Plasma-Treated→Quenched with Water→Packaged/Autoclaved in Buffered Saline An air only plasma (called Air Plasma-pretreated) before the normal $CH_4$/Air plasma (called $CH_4$/Air Plasma-treated) is applied to the lenses from Example 3.

There are three steps to complete the plasma treatment. The first step is the leak test, the second step is air only plasma pre-treatment, and the third step is $CH_4$/Air plasma treatment.

To avoid any contamination of leftover methane or air in the lines, a leak test is a must. It is carried out by setting the flow rate of methane at 0.0 sccm, and then pumping down the plasma chamber via rotary vacuum pump system for minimum 15 min.

After leaking test, the lenses are loaded in the plasma chamber. A vacuum chamber is then pumped down via rotary vacuum pump system to an absolute vacuum pressure 100 to 0 pa for 90 min. The plasma gas, air, is then introduced into the chamber by means of 0.0 sccm and 3.0 sccm for $CH_4$ and Air respectively. The plasma coating time is 3 min. Power across the electrodes is between 20 to 50 watts (power is at optimum at 30 watts); Current is 100 mA±10 mA (current set at 100 mA); Frequency set at 15 kHz; Voltage is based on the current setting, around 365 to 370 volt for Air only plasma treatment.

After the air only plasma pretreatment, plasma gases are then introduced into the chamber by means of 2.0 sccm (flow unit: standard cubic centimeters per minute) and 1.0 sccm for $CH_4$ and Air respectively. The plasma coating time is 11 min. Power across the electrodes is between 20 to 50 watts (power is at optimum at 30 watts); Current is 100 mA±10 mA (current set at 100 mA); Frequency set at 15 kHz; Voltage is based on the current setting, around 345 to 350 volt for $CH_4$/Air Plasma treatment.

After the $CH_4$/Air plasma treatment, the plasma coated lenses are quickly (<60 s) transferred into water for hydration with 20 min. The lenses are then packed in a Corona treated shell with PBS for autoclave at 120° C. for 45 min.

ST4b: Air Plasma-Pretreated→$CH_4$/Air Plasma-Treated→Quenched with Water→Packaged/Autoclaved in IPC Saline The surface treatment ST4b differs from ST4a only in the packaging solution: PBS in ST4a vs the IPC saline in ST4b.

ST4c: Air Plasma-Pretreated→$CH_4$/Air Plasma-Treated→Quenched with PAA→Packaged/Autoclaved in Buffered Saline The surface treatment ST4c differs from ST4a only in the quenching solution: water in ST4a vs the PAA solution in ST4c.

ST4d: Air Plasma-Pretreated→$CH_4$/Air Plasma-Treated→Quenched with PAA→Packaged/Autoclaved in IPC Saline The surface treatment ST4d differs from ST4a only in the quenching solution (water in ST4a vs PAA in ST4d) and in the packaging solution (PBS in ST4a vs IPC saline in ST4d).

ST5a: $CH_4$/Air Plasma-Treated→Air Plasma-Posttreated→Quenched with Water→Packaged/Autoclaved in Buffered Saline After the normal $CH_4$/Air plasma (called $CH_4$/Air Plasma-treated), an air only plasma (called Air Plasma-posttreated) is applied to the lenses from Example 3.

There are two steps to complete the plasma treatment. The first step is the normal $CH_4$/Air plasma, the second step is air only plasma.

The $CH_4$/Air plasma treatment step is carried out as described for ST1a. After $CH_4$/Air plasma, the air only plasma post-treatment is carried out directly. The plasma gas, air, is then introduced into the chamber by means of 0.0 sccm and 3.0 sccm for $CH_4$ and Air respectively. The plasma coating time is 3 min. Power across the electrodes is between 20 to 50 watts (power is at optimum at 30 watts); Current is between 100 mA±10 mA (current set at 100 mA); Frequency set at 15 kHz; Voltage is based on the current setting, around 365 to 370 volt for Air only plasma treatment.

After the plasma treatment, the plasma coated lenses are quickly (<60s) transferred into water for hydration with 20 min. The lenses are then packed in a Corona treated shell with PBS for autoclave at 120° C. for 45 min.

ST5b: $CH_4$/Air Plasma-Treated→Air Plasma-Posttreated→Quenched with Water→Packaged/Autoclaved in IPC Saline The surface treatment ST5b differs from ST5a only in the packaging solution: PBS in ST5a vs the IPC saline in ST5b.

ST5c: $CH_4$/Air Plasma-Treated→Air Plasma-Posttreated→Quenched with PAA→Packaged/Autoclaved in Buffered Saline The surface treatment ST5c differs from ST5a only in the quenching solution: water in ST5a vs the PAA solution in ST5c.

ST5d: $CH_4$/Air Plasma-Treated→Air Plasma-Posttreated→Quenched with PAA→Packaged/Autoclaved in IPC Saline The surface treatment ST5d differs from ST5a only in the quenching solution (water in ST5a vs PAA in ST5d) and in the packaging solution (PBS in ST5a vs IPC saline in ST5d).

Lens Characterization

The wettability (measured by water contact angle), surface hydrophilicity (measured by WBUT) and lubricity (measured by friction rating) of silicone contact lenses after being subjected to one of surface treatments above are determined according to the procedures described in Example 1 and reported in Table 4.

TABLE 4

| | Surface Treatment No. | | | | | | | | | |
|---|---|---|---|---|---|---|---|---|---|---|
| | ST1a | ST1b | ST1c | ST1d | ST2a | ST2b | ST2c | ST2d | ST3a | ST3b |
| WBUT (s) | 0 | 1 | 0 | 3 | 0 | 0 | 0 | 11 | 0 | 1 |
| FR | 4 | 4 | 4 | 2 | 4 | 3.5 | 4 | 1-2 | 4 | 3 |
| WCA (°) | 41 | 25 | 51 | 29 | 87 | 38 | 69 | 40 | 106 | 41 |

| | Surface Treatment No. | | | | | | | | | |
|---|---|---|---|---|---|---|---|---|---|---|
| | ST3c | ST3d | ST4a | ST4b | ST4c | ST4d | ST5a | ST5b | ST5c | ST5d |
| WBUT (s) | 4 | 6 | 0 | 1 | 0 | 8 | 0 | 1 | 0 | 1 |
| FR | 3 | 3 | 4 | 3 | 4 | 1-2 | 4 | 3 | 4 | 3 |
| WCA (°) | 32 | 29 | 69 | 43 | 37 | 34 | 104 | 22 | 61 | 25 |

Table 4 shows that the step of quenching plasma-treated lenses with water does not improve the surface hydrophilicity and lubricity of a silicone contact lens, whereas the step of quenching plasma-treated lenses with an aqueous PAA solution (1 mM PAA, pH~2.0) can improve the wettability and lubricity of a silicone contact lens. It also shows that the step of packaging/autoclaving in a buffered saline does not improve the surface hydrophilicity and lubricity of a silicone contact lens, whereas the step of packaging/autoclaving in an IPC saline (i.e., containing a water-soluble and thermally crosslinkable hydrophilic polymeric material) can improve the surface hydrophilicity and lubricity of a silicone contact lens.

Methylene Blue Staining Test

Methylene blue is positively charged and will bind to negatively charged surface as shown by staining. Such staining text can be used to determining whether a PAA layer is deposed or attached onto silicone contact lenses with or without subjecting to any plasma treatment and whether a water-soluble thermally crosslinkable hydrophilic polymeric material is crosslinked onto the PAA layer on the surface of a silicone contact lens.

Methylene blue is purchased from Sigma-Aldrich, and is used as received. 200 ppm Methylene blue aqueous is prepared by adding 0.2 g Methylene blue into 999.8 g distilled water with stirring at room temperature overnight. It is always freshly prepared.

For the Methylene Blue Staining Test, each lens is soaked in 20 ml of 200 ppm methylene blue aqueous for 30 min. After rinsing in 500 ml water twice for 30 min, the lens is kept in water for staining assessment.

Three types of silicone contact lenses:

(1) PAA-treated lenses: silicone contact lenses prepared in Example 3 without subjecting to any plasma treatment are dipped in an PAA aqueous solution (1 mM PAA, pH=2.0) for about two hours.

(2) (Plasma+PAA)-treated lenses: silicone contact lenses prepared in Example 3 are subjected to air plasma treatment and followed by dipping them in an PAA aqueous solution (1 mM PAA, pH=2.0) for about two hours.

(3) (Plasma+PAA+IPC)-treated lenses: silicone contact lenses prepared in Example 3 are subjected to air plasma treatment, followed by dipping them in an PAA aqueous solution (1 mM PAA, pH=2.0) for about two hours, and finally packaged/autoclaved in the IPC saline prepared above, are subjected to methylene blue staining test.

It is found that:

(1) the PAA-treated silicone contact lenses are not stained by methylene blue, indicating the absence of any PAA on the surface of the control lenses;

(2) the (plasma+PAA)-treated silicon contact lenses are stained by methylene blue, indicating the presence of a layer of PAA; and (3) the (plasma+PAA+IPC) silicon contact lenses are not stained by methylene blue, indicating that the layer of PAA is shielded by a top layer of hydrogel formed during autoclave.

Those results are further supported by XPS data shown in Table 5. The PAA-treated silicone contact lenses and the control silicone contact lenses have the same atomic compositions on their surfaces. But, the silicon content on the surface of the (plasma+PAA)-treated silicone contact lenses are substantially reduced, relative to that of the control silicone contact lenses.

TABLE 5

| | C | N | O | F | Si |
|---|---|---|---|---|---|
| Control lens (no surface treatment) | 43.7 | 1.9 | 30.2 | 2.1 | 22 |
| PAA-treated lens | 45 | 1.7 | 30.4 | 1.7 | 21.2 |
| (Plasma + PAA)-treated lens | 51.1 | 6.8 | 29.7 | 1.9 | 10.5 |

Example 6

IPC Saline.

An IPC saline prepared in Example 5 is used in this Example.

Surface Treatment

Silicone contact lenses prepared in Example 3 are subjected to the following surface treatments.

ST5: Air Plasma-Treated→Quenched with 1 mM PAA (pH=2.0)→Packaged/Autoclaved in IPC Saline The Air plasma treatment of the lenses from Example 3 is carried out as described for ST2a. After the Air plasma treatment, the plasma coated lenses are quickly (<60s) transferred into 1 mM PAA aqueous with 20 min. After rinsing in PBS twice for 30 min, the lenses are then packed in a Corona treated shell with IPC saline for autoclave at 120° C. for 45 min.

ST6: Air Plasma-Pretreated→Air Only Plasma-Treated→Quenched with Water→Packaged/Autoclaved in IPC Saline The surface treatment ST6 differs from ST4b only in the plasma gas for plasma treatment: $CH_4$/Air in ST4b vs Air in ST6.

ST7: $O_2$ Plasma-Treated→Quenched with 1 mM PAA (pH=2.0)→Packaged/Autoclaved in IPC Saline The dried lenses from Example 3 are $O_2$ Plasma-treated as described for ST3a. After the $O_2$ plasma treatment, the plasma coated lenses are quickly (<60 s) transferred into 1 mM PAA aqueous solution (pH 2) for 20 min. After rinsing in PBS twice for 30 min, the lenses are then packed in a Corona treated shell with IPC saline for autoclave at 120° C. for 45 min.

ST8: $CH_4$/Air Plasma-treated→Quenched with 1 mM PAA (pH=2.0)→Packaged/Autoclaved in IPC saline The $CH_4$/Air plasma treatment of the lenses from Example 3 is carried as described for ST1a. After the $CH_4$/Air plasma treatment, the plasma coated lenses are quickly (<60 s) transferred into 1 mM PAA aqueous with 20 min. After rinsing in PBS twice for 30 min, the lenses are then packed in a Corona treated shell with IPC saline for autoclave at 120° C. for 45 min.

ST9: Air Plasma-Pretreated→$CH_4$/Air Plasma-Treated→Quenched with 1 mM PAA (pH=2.0)→Packaged/Autoclaved in IPC Saline The Air plasma pretreatment and the $CH_4$/Air plasma treatment of the lenses from Example 3 are carried as described for ST4a. After the $CH_4$/Air plasma treatment, the plasma coated lenses are quickly (<60 s) transferred into 1 mM PAA aqueous with 20 min. After rinsing in PBS twice for 30 min, the lenses are then packed in a Corona treated shell with IPC saline for autoclave at 120° C. for 45 min.

ST10: $CH_4$/Air Plasma-Treated→Air Plasma-Post-Treated→Quenched with 1 mM PAA (pH=2.0)→Packaged/Autoclaved in IPC Saline The $CH_4$/Air plasma treatment and the Air plasma post-treatment of the lenses from Example 3 are carried out as described for ST5a. After the Air plasma post treatment, the plasma coated lenses are quickly (<60 s) transferred into 1 mM PAA aqueous solution (pH 2) for 20 min. After rinsing in PBS twice for 30 min, the lenses are then packed in a Corona treated shell with IPC saline for autoclave at 120° C. for 45 min.

Thickness of Plasma Coating or Layer

Plasma treatment can be grouped into plasma oxidation and plasma coating. Plasma oxidation just creates an ultra-thin layer with functional groups or charges on lens surface, while plasma coating will create an actual thin layer. This can be identified by plasma gas and plasma layer thickness. The thickness of a plasma coating or layer on a silicone contact lens after plasma treatment can be determined by ellipsometry on silicon wafers which are plasma-treated together with the silicone contact lens. The results are reported in Table 6.

Lens Characterization

The wettability (measured by water contact angle), surface hydrophilicity (measured by WBUT) and lubricity (measured by friction rating) of silicone contact lenses after being subjected to one of surface treatments above are determined according to the procedures described in Example 1 and reported in Table 6. Wettable, hydrophilicity and lubricious lens surface (CA<50°, WBUT>5s, FR=1-2) for lenses in Example 3 have been achieved by PAA quenched plasma approach. The final lenses are packed in IPC saline and autoclaved at 120° C. for 45 min.

TABLE 6

| Surface Treatment | Plasma coating/ Layer thickness (A°) | WBUT (s) | FR | WCA (°) |
|---|---|---|---|---|
| ST5 | 32 | 5-9 | 0.5-1 | 25 |
| ST6 | 27 | 10 | 1 | 36 |
| ST7 | 221 | 6 | 3 | 29 |
| ST8 | 249 | 3 | 2 | 29 |
| ST9 | 203 | 8-12 | 1-3 | 34 |
| ST10 | 136 | 1 | 3 | 25 |

Example 7

IPC Saline

An IPC saline prepared in Example 5 is used in this Example.

PBS (Phosphate-Buffered Saline)

To prepare PBS saline, 8 g of NaCl; 0.2 g of KCl; 1.44 g of $Na_2HPO_4$; 0.24 g of $KH_2PO_4$ are dissolved in 800 ml distilled $H_2O$. After adjusting pH to 7.4 with HCl, additional distilled $H_2O$ is then added to meet 1 L volume.

1 mM PAA Solution (pH 2)

To prepare 1 mM Poly(Acrylic Acid) (PAA) aqueous solution, 0.072 g PAA (Carbopol 907, powder) is gradually transferred into the 1000 ml bottle containing distilled water under stirring. Ensure the solution is stirring during the PAA addition. Stir the solution on the stirrer plate at room temperature overnight (~24 hrs). Verify that the PAA has fully dissolved. If the PAA has NOT fully dissolved, continue stirring and wait until no particulates are observed. 37% Hydrochloric acid solution (HCl, Fluka-318949) is applied to adjust pH of the 1 mM PAA solution to 2 under the pH meter.

1 mM PAA Solution (pH 4)

1 mM Poly(Acrylic Acid) (PAA) aqueous solution (pH 4) is prepared according to the procedure described above, except that the pH is adjusted to 4.

1 mM PAA Solution (pH 8)

1 mM Poly(Acrylic Acid) (PAA) aqueous solution (pH 8) is prepared according to the procedure described above, except that the pH is adjusted to 8 with a 50% Sodium hydroxide solution (NaOH, Sigma-Aldrich-415413).

1 mM PAA-20% 1-Propanol (1-PrOH) Solution (pH 2)

Firstly prepare the mixture of 80% (Wt) water and 20% (Wt) 1-PrOH. 800 g distilled water is added into a 2000 ml bottle with 200 g 1-PrOH. Stir the mixture solution on the stirrer plate at room temperature for about 30 min.

To prepare 1 mM Poly(Acrylic Acid) (PAA) solution in the mixture of 80% water and 20% 1-PrOH, 0.072 g PAA (Carbopol 907, powder) is gradually transferred into the 1000 ml bottle containing the mixture solution of 80% water and 20% 1-PrOH under stirring. Ensure the solution is stirring during the PAA addition. Stir the solution on the stirrer plate at room temperature overnight (~24 hrs). Verify that the PAA has fully dissolved. If the PAA has NOT fully dissolved, continue stirring and wait until no particulates are observed. 37% Hydrochloric acid solution (HCl, Fluka-318949) is applied to adjust pH of the 1 mM PAA solution to 2 under the pH meter.

10 mM PAA Solution (pH 4)

To prepare 10 mM Poly(Acrylic Acid) (PAA) aqueous solution, 0.72 g PAA (Carbopol 907, powder) is gradually transferred into the 1000 ml bottle containing distilled water under stirring. Ensure the solution is stirring during the PAA addition. Stir the solution on the stirrer plate at room temperature overnight (~24 hrs). Verify that the PAA has fully dissolved. If the PAA has NOT fully dissolved, continue stirring and wait until no particulates are observed. 37% Hydrochloric acid solution (HCl, Fluka-318949) is applied to adjust pH of the 10 mM PAA solution to 4 under the pH meter.

1% Poly (Amidoamine-Epichlorhydrin) (PAE) Aqueous Solution

PAE is purchased from Ashland Hercules Water Technologies Inc. and is used as received. 1% poly (amidoamine-epichlorhydrin) (PAE) aqueous solution is prepared by adding 4.2 g PAE (solid content 24.4%) into 95.8 g distilled water. Stir the solution on the stirrer plate at room temperature about 30 min.

10 mM Hyaluronic Acid (HA) Solution

HA (Mw~400-600 kDa, S9950) is purchased from Sigma-Aldrich and is used as received. 10 mM HA aqueous solution is prepared by adding 0.144 g HA into 200 g distilled water. Stir the solution on the stirrer plate at room temperature about 2 hours.

0.1% Poly(Glycidyl Methacrylate) (PGMA) in Methyl Ethyl Ketone (MEK) Solution

PGMA (Mw=10,000-20,000) and MEK are purchased from Sigma-Aldrich and are used as received. 0.1% PGMA aqueous solution is prepared by adding 0.1 g into 99.9 g MEK. Stir the solution on the stirrer plate at room temperature about 2 hours.

0.1% Poly(Vinyl Acetate) (PVA) Saline

PVA (Mw=500,000) is purchased from Sigma-Aldrich and is used as received. 0.1% PVA aqueous solution is prepared by adding 0.02 g into 20 g PBS. Stir the solution on the stirrer plate at room temperature about 30 min.

0.1% poly(N-vinylpyrrolidone-co-acrylic acid) poly(VP-co-AA) Saline

Poly(VP-co-AA) (Mw=1128,900) is purchased from Sigma-Aldrich and is used as received. 0.1% PVA aqueous solution is prepared by adding 0.02 g into 20 g PBS. Stir the solution on the stirrer plate at room temperature about 2 hours.

Surface Treatment

Silicone contact lenses prepared in Example 3 are subjected to the following surface treatments.

Air Plasma-Treated Lenses

The Air plasma-treatment is carried out as described for ST2a. After the Air plasma treatment, the plasma coated lenses are quickly (<60 s) transferred into different aqueous solutions for quenching and packed for autoclaving.

ST11: Air Plasma-Treated→Quenched with Water→Packaged/Autoclaved in IPC Saline

After the Air plasma treatment, the plasma coated lenses are quickly (<60 s) transferred into distilled water with 20 min. Then the lenses are packed in a Corona treated shell with IPC saline for autoclave at 120° C. for 45 min.

ST12: Air Plasma-Treated→Quenched with 1 mM PAA (pH=2.0)→Packaged/Autoclaved in IPC Saline After the Air plasma treatment, the plasma coated lenses are quickly (<60 s) transferred into 1 mM PAA aqueous (pH=2) with 20 min. After rinsing in PBS twice for 30 min, the lenses are then packed in a Corona treated shell with IPC saline for autoclave at 120° C. for 45 min.

ST13: Air Plasma-Treated→Quenched with 1 mM PAA (pH=4.0)→Packaged/Autoclaved in IPC Saline After the Air plasma treatment, the plasma coated lenses are quickly (<60 s) transferred into 1 mM PAA aqueous (pH=4) with 20 min. After rinsing in PBS twice for 30 min, the lenses are then packed in a Corona treated shell with IPC saline for autoclave at 120° C. for 45 min.

ST14: Air Plasma-Treated→Quenched with 1 mM PAA (pH=8.0)→Packaged/Autoclaved in IPC Saline After the Air plasma treatment, the plasma coated lenses are quickly (<60 s) transferred into 1 mM PAA aqueous (pH=8) with 20 min. After rinsing in PBS twice for 30 min, the lenses are then packed in a Corona treated shell with IPC saline for autoclave at 120° C. for 45 min.

ST15: Air Plasma-Treated→Quenched with 1 mM PAA (w/20% 1-PrOH)→Packaged/Autoclaved in IPC Saline After the Air plasma treatment, the plasma coated lenses are quickly (<60 s) transferred into 1 mM PAA (w/20% 1-PrOH) with 20 min. After rinsing in PBS twice for 30 min, the lenses are then packed in a Corona treated shell with IPC saline for autoclave at 120° C. for 45 min.

ST16: Air Plasma-Treated→Quenched with 10 mM PAA (pH=4.0)→Packaged/Autoclaved in IPC Saline After the Air plasma treatment, the plasma coated lenses are quickly (<60 s) transferred into 10 mM PAA aqueous (pH=4) with 20 min. After rinsing in PBS twice for 30 min, the lenses are then packed in a Corona treated shell with IPC saline for autoclave at 120° C. for 45 min.

ST17: Air Plasma-Treated→Quenched with 1% PAE Solution→Packaged/Autoclaved in IPC Saline After the Air plasma treatment, the plasma coated lenses are quickly (<60 s) transferred into 1% PAE solution with 20 min. After rinsing in PBS twice for 30 min, the lenses are then packed in a Corona treated shell with IPC saline for autoclave at 120° C. for 45 min.

ST18: Air Plasma-Treated→Quenched with the IPC Saline→Packaged/Autoclaved in IPC Saline After the Air plasma treatment, the plasma coated lenses are quickly (<60 s) transferred into IPC saline with 20 min. After rinsing in PBS twice for 30 min, the lenses are then packed in a Corona treated shell with IPC saline for autoclave at 120° C. for 45 min.

ST19: Air Plasma-Treated→Quenched with 10 mM HA→Packaged/Autoclaved in IPC Saline After the Air plasma treatment, the plasma coated lenses are quickly (<60 s) transferred into 10 mM HA solution with 20 min. After rinsing in PBS twice for 30 min, the lenses are then packed in a Corona treated shell with IPC saline for autoclave at 120° C. for 45 min.

ST20: Air Plasma-Treated→Quenched with 0.1% PGMA/MEK Solution→Packaged/Autoclaved in IPC Saline After the Air plasma treatment, the plasma coated lenses are quickly (<60 s) transferred into 0.1% PGMA/MEK solution with 20 min. After rinsing in PBS twice for 30 min, the lenses are then packed in a Corona treated shell with IPC saline for autoclave at 120° C. for 45 min.

ST21: Air Plasma-Treated→Quenched with 0.1% PGMA Solution→Packaged/Autoclaved in 0.1% PVA Saline After the Air plasma treatment, the plasma coated lenses are quickly (<60 s) transferred into 0.1% PGMA/MEK solution with 20 min. After rinsing in PBS twice for 30 min, the lenses are then packed in a Corona treated shell with 0.1% PVA saline for autoclave at 120° C. for 45 min.

ST22: Air Plasma-Treated→Quenched with 0.1% PGMA Solution→Packaged/Autoclaved in 0.1% Poly(VP-Co-AA) Saline After the Air plasma treatment, the plasma coated lenses are quickly (<60 s) transferred into 0.1% PGMA/MEK solution with 20 min. After rinsing in PBS twice for 30 min, the lenses are packed in a Corona treated shell with 0.1% poly(VP-co-AA) saline for autoclave at 120° C. for 45 min.

ST23: Air Plasma-Treated→Quenched with the IPC Saline→Packaged/Autoclaved in PBS After the Air plasma treatment, the plasma coated lenses are quickly (<60 s) transferred into IPC saline with 20 min. After rinsing in PBS twice for 30 min, the lenses are then packed in a Corona treated shell with PBS saline for autoclave at 120° C. for 45 min.

ST24: Air Plasma-Treated→Quenched with the IPC Saline→Packaged/Autoclaved in IPC Saline After the Air plasma treatment, the plasma coated lenses are quickly (<60 s) transferred into IPC saline with 20 min. After rinsing in PBS twice for 30 min, the lenses are then packed in a Corona treated shell with IPC saline for autoclave at 120° C. for 45 min.

ST25: Air Plasma-Pretreated→Air Plasma-Treated→Quenched with the IPC Saline→Packaged/Autoclaved in PBS The Air plasma pretreatment and the Air plasma treatment of the lenses from Example 3 are carried out as described for ST6. After the Air Plasma-treatment, the plasma coated lenses are quickly (<60 s) transferred into IPC saline with 20 min. After rinsing in PBS twice for 30 min, lenses are packed in a Corona treated shell with PBS saline for autoclave at 120° C. for 45 min.

ST26: Air Plasma-Pretreated→Air Plasma-Treated→Quenched with the IPC Saline→Packaged/Autoclaved in IPC Saline The Air plasma pretreatment and the Air plasma treatment of the lenses from Example 3 are carried out as described for ST6. After the Air Plasma-treatment, the plasma coated lenses are quickly (<60 s) transferred into IPC saline with 20 min. After rinsing in PBS twice for 30 min, the lenses are packed in a Corona treated shell with IPC saline for autoclave at 120° C. for 45 min.

ST27: Air Plasma-Pretreated→$CH_4$/Air Plasma-Treated→Quenched with the IPC Saline→Packaged/Autoclaved in PBS The Air plasma pretreatment and the $CH_4$/Air plasma treatment of the lenses from Example 3 are carried out as described for ST9. After the $CH_4$/Air Plasma-treatment, the plasma coated lenses are quickly (<60 s) transferred into IPC saline with 20 min. After rinsing in PBS twice for 30 min, the lenses are then packed in a Corona treated shell with PBS saline for autoclave at 120° C. for 45 min.

ST28: Air Plasma-Pretreated→$CH_4$/Air Plasma-Treated→Quenched with the IPC Saline→Packaged/Autoclaved in IPC Saline The Air plasma pretreatment and the $CH_4$/Air plasma treatment of the lenses from Example 3 are carried out as described for ST9. After the $CH_4$/Air Plasma-treatment, the plasma coated lenses are quickly (<60 s) transferred into IPC saline with 20 min. After rinsing in PBS twice for 30 min, the lenses are then packed in a Corona treated shell with IPC saline for autoclave at 120° C. for 45 min.

Lens Characterization

The wettability (measured by water contact angle), hydrophilicity (measured by WBUT) and lubricity (measured by friction rating) of silicone contact lenses after being subjected to one of surface treatments above are determined according to the procedures described in Example 1 and reported in Tables 6-8.

TABLE 6

| Surface Treatment | Quenching solution | WBUT (s) | FR | WCA (°) |
|---|---|---|---|---|
| No (Control) | | 0 | 4 | 108 |
| ST11 | Water | 0 | 3 | 58 |
| ST12 | 1 mM PAA, pH = 2.0 | 5-9 | 0.5-1 | 25 |
| ST13 | 1 mM PAA, pH = 4.0 | 3 | 3 | 24 |
| ST14 | 1 mM PAA, pH = 8.0 | 5 | 3 | 54 |
| ST15 | 20% 1-PrOH, 1 mM PAA | 3 | 3 | 40 |
| ST16 | 10 mM PAA, pH = 4.0 | 7-9 | 2 | 30 |

TABLE 7

| Surface Treatment | Quenching solution | Packaging saline | WBUT (s) | FR | WCA (°) |
|---|---|---|---|---|---|
| No (Control) | — | water | 0 | 4 | 108 |
| ST17 | 1% PAE | IPC | 3 | 4 | 46 |
| ST18 | IPC saline | IPC | 8 | 3 | 35 |
| ST19 | 10 mM HA | IPC | 0 | 4 | 51 |
| ST20 | 0.1% PGMA | IPC | 0 | 4 | 54 |
| ST21 | 0.1% PGMA | 0.1% PVA | 0 | 4 | 54 |
| ST22 | 0.1% PGMA | 0.1% p(VP-AA) | 0 | 4 | 51 |

TABLE 8

| Surface Treatment | Quenching solution | Packaging saline | WBUT (s) | FR | WCA (°) |
|---|---|---|---|---|---|
| ST23 | IPC saline | PBS | 8 | 3 | 46 |
| ST24 | IPC saline | IPC | 8 | 3 | 35 |
| ST25 | IPC saline | PBS | 11 | 2 | 46 |
| ST26 | IPC saline | IPC | 5 | 2 | 36 |
| ST27 | IPC saline | PBS | 11 | 3 | 40 |
| ST28 | IPC saline | IPC | 5 | 1 | 40 |

It is found that: when the pH of the PAA aqueous for the quenching step is about 2, the higher hydrophilicity (WBUT) and lubricity can be achieved; when the quenching solution contains a water-soluble and thermally crosslinkable hydrophilic polymeric material (having azetidinium and carboxyl groups) can increase WBUT but cannot significantly change the lubricity; when the surface treatment includes an air-plasma-pretreatment step, both WBUT and lubricity can be improved.

Example 8

IPC Saline.

An IPC saline prepared in Example 5 is used in this Example.

Surface Treatment

Silicone contact lenses prepared in Example 3 are subjected to the surface treatment ST12 described in Example 7.

Lens Characterization

The wettability (measured by water contact angle), surface hydrophilicity (measured by WBUT) and lubricity (measured by friction rating) of silicone contact lenses after being subjected to one of surface treatments above are determined to be: WBUT of from 12 to 17 s; friction rating of 1; and WCA of 35 degrees.

Example 9

IPC Saline.

An IPC saline prepared in Example 5 is used in this Example.

IPC-1 Saline

A reaction mixture is prepared by dissolving 3.0% by weight of mPEG-SH 2000 (Methoxy-Poly(Ethylene Glycol)-Thiol, Avg MW 2000, Product #M PEG-SH-2000, Laysan Bio Inc.) along with 17.72% by weight of PAE (Kymene from Ashland as an aqueous solution and used as received, azetidinium content of 0.46 assayed with NMR, solid content of 25.4%) in PBS and 7.5% of sodium citrate dihydrate. The pH of this solution is then adjusted to 7.5 and also degassed by bubbling nitrogen gas through the container for 2 hours. This solution is later heat treated for about 4 hours at 45° C. forming a thermally crosslinkable hydrophilic polymeric material containing mPEG-SH-2000 groups chemically grafted onto the polymer by reaction with the Azetidinium groups in PAE. After the heat-treatment, the solution is diluted 30-fold using PBS containing 0.25% sodium citrate, pH adjusted to 7.2-7.4, and then filtered using 0.22 micron polyether sulphone (PES) membrane filter. The final IPC saline contains about 0.25% by weight of the polymeric material (consisting of about 40% wt. mPEG-SH-2000 and about 60% wt. PAE) and 0.25% Sodium citrate dihydrate.

IPC-2 Saline (Containing AZM Copolymer)

The AZM copolymer is an Amphiphilic copolymer containing AZM/AA/PDMS/DMA. This AZM copolymer is prepared as following. In a 1 L glass reaction kettle 6.0 grams of monomethacryloxypropyl terminated polydimethylsiloxane (Gelest catalog# MCR-M11) ($PDMS_{1000}$-MA) is added. A lid is put onto the reaction kettle that contains at 4 ground glass joints, one used for a glass stir shaft, one for a thermocouple, one for vacuum and nitrogen inlet, one for a 200 mL pressure equalizing addition funnel, and one for sampling access. A 2 mbar vacuum is pulled to degas the $PDMS_{1000}$-MA for 10 minutes. After about 10 minutes, reaction kettle is filled with nitrogen. This degassing and nitrogen-filing procedure is repeated 6 times. In the 200 mL pressure equalizing addition funnel, 3.0 grams of diethyl azetidinium methacrylate ester chloride salt (AZM), 6.0 grams of acrylic acid (AA), 14.91 grams of N,N'-dimethylacrylamide (DMA), and 3.00 mL of a 1% Irgacure 2959 solution in t-amyl alcohol are dissolved in 100.3 grams of t-amyl alcohol and 33.3 grams of methanol. A 100 mbar vacuum is pulled on the solution in the addition funnel for about 10 minutes. After about 10 minutes the funnel is filled with nitrogen. This degassing and nitrogen-filling procedure is repeated 3 times. After both $PDMS_{1000}$-MA and solution have been degassed, add the solution to the kettle with the $PDMS_{1000}$-MA. The stir speed is set to 150 rpm. The reaction kettle is put into a Rayonet UV reactor with RPR-3500 UV bulbs. Two UV bulbs are turned on for about one hour at an intensity of about 2.0 mW/cm². The copolymer solution is then purified using 25 kDa dialysis membranes against 1-PrOH for about 35 hours including two changes of 1-PrOH (1-propanol) during that time. The solids content is determined and diluted to 10% if necessary.

Preparation of phosphate/citrate buffer concentrate: The buffer concentrate is prepared by dissolving 0.484% by weight of sodium citrate dihydrate, 0.708% by weight of sodium phosphate dibasic, 0.088% by weight of sodium phosphate monobasic, monohydrate, and 1.486% by weight of sodium chloride in DI water. The pH is adjusted to about 7.2, if necessary.

IPC-2 Saline is prepared by adding 1 g AZM-containing copolymer into 49 g phosphate/citrate buffer prepared above. The pH of IPC-2 saline is adjusted, if necessary, to pH 7.2 to 7.4.

Surface Treatment

Silicone contact lenses prepared in Example 3 are subjected to one of ST28 described in Example 7 and the following surface treatments.

ST29: Air Plasma-Pretreated→$CH_4$/Air Plasma-Treated→Quenched with the IPC-1 Saline→Packaged/Autoclaved in IPC Saline The Air plasma pretreatment and the $CH_4$/Air plasma treatment of the lenses from Example 3 are carried out as described for ST9. After the $CH_4$/Air Plasma-treatment, the plasma coated lenses are quickly (<60 s) transferred into IPC-1 saline (PAE-thiol copolymer) with 20 min. After rinsing in PBS twice for 30 min, the lenses are then packed in a Corona treated shell with IPC saline for autoclave at 120° C. for 45 min.

ST30: Air Plasma-Pretreated→$CH_4$/Air Plasma-Treated→Quenched with the IPC-2 Saline→Packaged/Autoclaved in IPC Saline The Air plasma pretreatment and the $CH_4$/Air plasma treatment of the lenses from Example 3 are carried out as described for ST9. After the $CH_4$/Air Plasma-treatment, the plasma coated lenses are quickly (<60 s) transferred into IPC-2 saline (AZM copolymer) with 20 min. After rinsing in PBS twice for 30 min, the lenses are then packed in a Corona treated shell with IPC saline for autoclave at 120° C. for 45 min.

Lens Characterization

The wettability (measured by water contact angle), hydrophilicity (measured by WBUT) and lubricity of silicone contact lenses after being subjected to one of surface treatments above are determined according to the procedures described in Example 1 and reported in Table 9.

TABLE 9

| Surface Treatment | Quenching solution | Packaging saline | WBUT (s) | FR | WCA (°) |
| --- | --- | --- | --- | --- | --- |
| ST28 | IPC saline | IPC | 11-14 | 1-2 | 27 |
| ST29 | IPC-1 saline | IPC | 0 | 3 | 30 |
| ST30 | IPC-2 saline | IPC | 6 | 3.5 | 23 |

The results for ST29 indicate that a water-soluble and thermally crosslinkable hydrophilic polymeric material, which is free of any one of carboxyl, primary amino and secondary amino groups, is not suitable for quenching a plasma-treated silicone contact lens.

Example 10

IPC Saline.

An IPC saline prepared in Example 5 is used in this Example.

Surface Treatment

Silicone contact lenses prepared in Example 3 are subjected to one of the following surface treatments.

ST31: $CO_2$ Plasma-Treated→Quenched with Water→Packaged/Autoclaved in IPC Saline The dried lenses are $CO_2$ Plasma-treated by rotary plasma process, using the gas of $CO_2$ only in the plasma chamber.

After detaching methane gas cylinder, $CO_2$ gas cylinder is to be connected to replace methane gas cylinder. To avoid any contamination of leftover methane in the line, a leak test is a must. It is carried out by setting the flow rate of $CO_2$ at 0.0 sccm, and then pumping down the plasma chamber via rotary vacuum pump system for minimum 15 min.

After loading the lenses in the plasma chamber, a vacuum chamber is then pumped down via rotary vacuum pump system to an absolute vacuum pressure 100 to 0 pa for 90 min. The plasma gas, $CO_2$, is then introduced into the chamber by means of 3.0 sccm. The plasma coating time is 11 min. Power across the electrodes is between 20 to 50 watts (power is at optimum at 30 watts); Current is between 100 mA+10 mA; Frequency set at 15 kH; Voltage is based on the current setting, around 365 to 370 volt for $CO_2$ only plasma treatment.

After the plasma treatment, the plasma coated lenses are quickly (<60 s) transferred into water with 20 min. Then, the lenses are packed in a Corona treated shell with IPC saline for autoclave at 120° C. for 45 min.

ST32: $CO_2$ Plasma-Treated→Quenched with PAA Solution (pH 2)→Packaged/Autoclaved in IPC Saline The $CO_2$ plasma treatment is carried out as described for ST31. After the $CO_2$ plasma treatment, the plasma coated lenses are quickly (<60 s) transferred into 1 mM PAA aqueous (pH=2) with 20 min. After rinsing in PBS twice for 30 min, the lenses are then packed in a Corona treated shell with IPC saline for autoclave at 120° C. for 45 min.

ST33: $CO_2$ Plasma-Treated→Quenched with IPC Saline→Packaged/Autoclaved in IPC Saline The $CO_2$ plasma treatment is carried out as described for ST31. After the $CO_2$ plasma treatment, the plasma coated lenses are quickly (<60 s) transferred into IPC saline with 20 min. After rinsing in PBS twice for 30 min, the lenses are then packed in a Corona treated shell with IPC saline for autoclave at 120° C. for 45 min.

Lens Characterization

The wettability (measured by water contact angle), hydrophilicity (measured by WBUT) and lubricity (measured by friction rating) of silicone contact lenses after being subjected to one of surface treatments above are determined according to the procedures described in Example 1 and reported in Table 10.

TABLE 10

| Surface Treatment | Quenching solution | Packaging saline | WBUT (s) | FR |
|---|---|---|---|---|
| ST31 | water | IPC | 2-7 | 3 |
| ST32 | 1 mM PAA (pH 2) | IPC | 9-11 | 0-1 |
| ST33 | IPC saline | IPC | 5 | 2 |

Example 11

A DOE (design of experiments) has been carried out to screen the best conditions to achieve the wettable and lubricious surface on pure-PDMS lens as in Example 3. This plasma quenching technology contains three steps. The first step is the plasma with different plasma gas; the second step is the quenching process in aqueous containing hydrophilic polymers; the third step is the packaging saline for autoclaving. Thus there are three factors in the DOE screening.

The screening of plasma gas: (1) $O_2$ only; (2) $CO_2$ only; (3) $CH_4$ only; (4) $CO_2/CH_4$=4:1; (5) $CO_2/CH_4$=2:1; (6) $CO_2/CH_4$=1:1; (7) $O_2/CH_4$=4:1; (8) $O_2/CH_4$=2:1; (9) $O_2/CH_4$=1:1. The screening of quenching aqueous: (1) water; (2) 1 mM PAA; (3) IPC saline. For the DOE samples, the packaging saline will be the IPC saline. The lens evaluations are WBUT and friction rating, as reported in Table 11.

To screen plasma gas, all the lenses are quenched in 1 mM PAA (pH=2) with quenching time=2 h, and packed in IPC saline. WBUT and friction rating are utilized to assess coating quality (Table 11). Wettable and lubricious lens surface has been achieved with $CO_2$, $CH_4$, the mixture of $CO_2/CH_4$ or $O_2/CH_4$ plasma followed by "quenching" in PAA aqueous and packaging in IPC SALINE buffer. $CO_2$ only and $CH_4$ only plasma is better than $O_2$ only from the lens lubricity with PAA quenching.

In the DOE samples, quenching materials include water, PAA or PAA-free (IPC). Quenching in PAA, lens showed improved lubricity at level 0-1 (vs. control level at 4); while quenching in PAA-free, e. g. IPC saline, lens lubricity just is slightly improved.

Thus the approach of Plasma/quenching in PAA/IPC-packaging is a successful method to build up wettability and lubricity onto pure-PDMS lens.

TABLE 11

| Run# | Plasma gas | Quenching Sol. | WBUT | FR | WCA (°) |
|---|---|---|---|---|---|
| 1 | $CO_2/CH_4$ = 4:1 | 1 mM PAA | 12, 13 | 0.5, 0.5 | 22 |
| 2 | CO2/CH4 = 1:1 | 1 mM PAA | 7, 8 | 1, 1 | 28 |
| 3 | $CH_4$ | 1 mM PAA | 15, 15 | 1, 1 | — |
| 4 | $CO_2/CH_4$ = 2:1 | $H_2O$ | 4, 7 | 4, 4 | — |
| 5 | $CO_2$ | 1 mM PAA | 11, 9, 9 | 0, 1, 1 | 24 |
| 6 | $O_2$ | IPC | 5 | 1 | — |
| 7 | $O_2/CH_4$ = 2:1 | 1 mM PAA | 14, 14 | 0.5, 0.5 | — |
| 8 | $CO_2/CH_4$ = 2:1 | 1 mM PAA | 13, 16 | 0, 0 | 41 |
| 9 | $O_2/CH_4$ = 1:1 | IPC | 10, 11 | 4, 4 | — |
| 10 | $CO_2/CH_4$ = 4:1 | $H_2O$ | 9, 9 | 4, 4 | — |
| 11 | $O_2/CH_4$ = 2:1 | IPC | 12, 13 | 3, 3 | — |
| 12 | $O_2$ | $H_2O$ | 0 | 3 | — |
| 13 | $CO_2$ | $H_2O$ | 2, 6, 7 | 1, 3, 3 | — |
| 14 | $O_2/CH_4$ = 1:1 | 1 mM PAA | 15, 16 | 3, 3 | — |
| 15 | $CO_2$ | IPC | 5, 5, 5 | 2, 2, 2 | 22 |
| 16 | $O_2/CH_4$ = 4:1 | $H_2O$ | 3, 5 | 4, 4 | — |
| 17 | $O_2/CH_4$ = 2:1 | $H_2O$ | 8, 9 | 3.5, 3.5 | — |
| 18 | $O_2/CH_4$ = 4:1 | 1 mM PAA | 14, 16 | 0, 0 | — |
| 19 | $O_2/CH_4$ = 4:1 | IPC | 13, 14 | 3, 3 | — |
| 20 | $CO_2/CH_4$ = 1:1 | $H_2O$ | 3, 4 | 3.5, 3.5 | — |
| 21 | $CO_2/CH_4$ = 4:1 | IPC | 13, 13 | 3, 3 | 33 |
| 22 | $CO_2/CH_4$ = 1:1 | IPC | 8, 8 | 2, 2 | 26 |
| 23 | $O_2$ | 1 mM PAA | 5 | 1 | — |
| 24 | $O_2/CH_4$ = 1:1 | $H_2O$ | 9, 9 | 4, 4 | — |
| 25 | $CH_4$ | IPC | 0, 0 | 4, 4 | — |
| 26 | $CH_4$ | $H_2O$ | 0, 0 | 4, 4 | — |
| 27 | $CO_2/CH_4$ = 2:1 | IPC | 13, 13 | 3, 3 | 37 |

Example 12

Effects of Quenching Solution after Plasma Treatment

Lenses prepared in Example 3 are plasma-treated according to ST or ST described above. After the plasma treatment, plasma coated lenses are quenched in water or 1 mM PAA aqueous solution (pH 2). With rinsing in PBS twice for 30 min, the lenses are then packed in a Corona treated shell with IPC saline for autoclave at 120° C. for 45 min.

The surface properties of resultant lenses are reported in Table 12. The results show that water as quenching solution has no effect on WBUT and friction rating of the lenses, whereas the PAA solution as quenching solution can significantly improve lens surface properties (Table 12). This significant difference indicates that PAA can be bounded onto lens surface after plasma treatment. In contrast, Example 5 shows that PAA cannot be bound onto the surface of lens without plasma treatment just by dipping the lens in a PAA solution.

TABLE 12

|  | Quenching buffer | WBUT | FR | WCA(°) |
|---|---|---|---|---|
| Air-only plasma | water | 0 | 3.5 | 38 |
|  | 1 mM PAA | 11 | 1-2 | 40 |
| Air pre-treatment + | water | 1 | 3 | 43 |
| regular methane/air plasma | 1 mM PAA | 8 | 1-2 | 34 |

Effects of pH of Quenching Solution

Lenses prepared in Example 3 are plasma-treated with $CO_2$ plasma according to ST described above. After the $CO_2$ plasma treatment, plasma coated lenses are quenched in a quenching solution having a varying pH. With rinsing in PBS twice for 30 min, the lenses are then packed in a Corona treated shell with IPC saline for autoclave at 120° C. for 45 min. The surface properties of resultant lenses are reported in Table 13. The results show that changing pH of water or IPC saline as quenching solution has no or minimal impact upon lens surface properties (Table 13). This indicates that quenching material is critical.

TABLE 13

| Pure-PDMS, $CO_2$ plasma Packed in IPC saline | Quenched in PAA pH = 2 | Quenched in water | | Quenched in IPC saline | |
|---|---|---|---|---|---|
|  |  | pH = 7.1 | pH2 | pH = 7.2 | pH = 2 |
| WBUT | 18, 18 | 6, 7 | 4, 4 | 5, 5 | 6, 6 |
| FR | 1, 1 | 4, 3 | 3.5, 3.5 | 2, 2 | 3, 3 |

Effects of Packaging Saline

Lenses prepared in Example 3 are plasma-treated. After the plasma treatment, plasma coated lenses are quenched in a 1 mM PAA aqueous solution (pH 2). With rinsing in PBS twice for 30 min, the lenses are then packed in a Corona treated shell with PBS or IPC saline for autoclave at 120° C. for 45 min. The surface properties of resultant lenses are reported in Table 14. The results show that the IPC saline packed lens has a significantly improved surface properties over the PBS packed lens, indicating the formation of a prime (or base or anchoring) coating on lenses during PAA quenching process. The quenched lens packed in PBS has a poor hydrophilic surface (WBUT=0) and a very poor lubricity (FR of 4), indicating that the prime coating would be an ultra-thin layer too thin to have a WBUT and lubricity enhancement.

TABLE 14

|  | Packaging buffer | WBUT | FR | WCA(°) |
|---|---|---|---|---|
| Air-only plasma | PBS | 0 | 4 | 69 |
|  | IPC | 11 | 1-2 | 40 |
| Air pre-treatment + | PBS | 0 | 4 | 37 |
| regular methane/air plasma | IPC | 8 | 1-2 | 34 |

XPS Data

All the lenses in Table 15 are packed in IPC saline. The control lens is pure PDMS lens without plasma/quenching treatment. The testing samples are air-only plasma treated and quenched in water or 1 mM PAA (pH=2) respectively.

The increasing of N and decreasing of "Si" in Table 15 indicates surface composition changes resulted from plasma treatment and/or quenching in water or PAA aqueous solution.

TABLE 15

|  | Quenching aqueous | N (%) | Si (%) |
|---|---|---|---|
| Pure-PDMS, +6.00 | NA | 1.9 | 21.7 |
| (control, without plasma) | NA | 2.3 | 21.1 |
|  | NA | 0.9 | 21.6 |
|  | NA | 2 | 21.5 |
|  | NA | 2.2 | 18.7 |
|  | NA | 2.4 | 21.5 |
| Pure-PDMS, +6.00 | water | 1.7 | 18.4 |
| Air only plasma | water | 2.6 | 19 |
|  | water | 1.9 | 18.4 |
|  | 1 mM PAA, pH = 2 | 5 | 12.6 |
|  | 1 mM PAA, pH = 2 | 6.7 | 11.2 |
|  | 1 mM PAA, pH = 2 | 8.7 | 7.6 |
|  | 1 mM PAA, pH = 2 | 8.1 | 9 |
|  | 1 mM PAA, pH = 2 | 7.3 | 9.1 |
|  | 1 mM PAA, pH = 2 | 6.2 | 11.5 |

Example 13

FSI/Cracking of Lens Surface:

FSI/cracking issue appeared on PAA coated lenses. The plasma quenched pure-PDMS is prepared by air-only plasma with quenching in 1 mM PAA aqueous solution (pH 2) for 2 h. There is NO FSI/cracking issue on this plasma quenched pure-PDMS lens, as shown in Table 16.

TABLE 16

|  | FSI | Cracking |
|---|---|---|
| Air-only plasma with PAA quenching, packed in IPC SALINE | 1, 1, 1 | 0, 0, 0 |

Phmb Uptaking:

The amount of PAA deposited on lens surface during quenching process can contribute to the PHMB uptaking. The tested lenses are prepared by air-only plasma treating pure PDMS lenses and followed by quenching in 1 mM PAA aqueous for different time or quenching in IPC saline for 2 h. Results show no PHMB uptaking (Table 17).

TABLE 17

| Lens | Air-only Plasma | Process (all lens packed in IPC saline) | PHMB uptaking (ug/lens) |
|---|---|---|---|
| Lotrafilcon B | NO | Dip in 0.025% PAA/1-PrOH for 1 min | 22.23 |
|  | NO | Dip in 0.025% PAA/1-PrOH for 1 min | 22.36 |
| Pure-PDMS, +6.00 | YES | Quenching in 1 mM PAA pH = 2 for 1 min | 1.55 |
|  | YES | Quenching in 1 mM PAA pH = 2 for 1 min | 0.24 |
|  | YES | Quenching in 1 mM PAA pH = 2 for 2 min | 1.67 |

TABLE 17-continued

| Lens | Air-only Plasma | Process (all lens packed in IPC saline) | PHMB uptaking (ug/lens) |
|---|---|---|---|
| | YES | Quenching in 1 mM PAA pH = 2 for 2 min | 1.02 |
| | YES | Quenching in 1 mM PAA pH = 2 for 5 min | 1.33 |
| | YES | Quenching in 1 mM PAA pH = 2 for 5 min | 1.52 |
| | YES | Quenching in 1 mM PAA pH = 2 for 2 h | 1.63 |
| | YES | Quenching in 1 mM PAA pH = 2 for 2 h | 2.21 |
| | YES | Quenching in IPC saline for 2 h | 0.34 |
| | YES | Quenching in IPC saline for 2 h | 0.16 |

Example 14

The lenses prepared in Example 3 are digitally rubbed (wearing disposable powder-free latex gloves) with RENU® multi-purpose lens care solution (or another multi-purpose lens care solution) for 20 seconds and then rinsed with saline. The above procedure is repeated for a given times, e.g., from 1 to 30 times, (i.e., number of repetitions of digital rubbing tests which imitate cleaning and soaking cycles).

To check the durability of plasma quenched pure-PDMS lens surface, 7 digital rubbing cycles and 15 digital rubbing cycles are carried out by fingers with a rubbing solution (Renu or Optifree lens care solution). WBUT and friction rating are determined to evaluate the durability of plasma quenched lenses. The plasma quenched pure-PDMS lenses are prepared by air-only plasma or Air-pretreat+methane/air plasma with quenching in 1 mM PAA aqueous (pH=2) for 2 h or in IPC saline for 2 h. After plasma quenching, the lenses are packed in IPC saline for autoclaving at 120° C. for 45 min.

Examples 15

Lenses made of pure-PDMS elastomer are used in this example. The lens surface is hydrophobic. To achieve the wettable lens surface plasma coating is tried. The plasma coating is obtained by using $CH_4$/air plasma gas with 11 min plasma treating time. The XPS result of significant decreasing of the element, Si, on lens surface in table 19 has confirmed the successful plasma coating.

However, hydrophobic property came back after one month dry-storage (in its dry state) at room temperature. After rehydration in PBS, the WBUT drops to is from the original reading of 8 s. Thus the plasma coating only will not improve the surface of pure-PDMS rubber lens.

TABLE 18

| | | Rubbing | 7 rubbing cycles | | 15 rubbing cycles | |
|---|---|---|---|---|---|---|
| | $WBUT_{0DR}$ | solution | $WBUT_{7DR}$ | $\Delta WBUT_{DR}(7)$ | $WBUT_{15DR}$ | $\Delta WBUT_{DR}(15)$ |
| Pure-PDMS, +6.00. Control (w/o coating) | 0 | Renu Optifree | 0 | — | 0 | — |
| Pure-PDMS, air-only plasma/1 mM PAA (pH = 2)-2 h/IPC saline | 14 | Renu | 13 | 7.1% | 10 | 28.6% |
| | 17 | Renu | 17 | 0 | 10 | 41.2% |
| | 12 | Renu | 12 | 0 | 10 | 16.7% |
| | 17 | Optifree | 14 | 17.6% | 11 | 35.3% |
| | 16 | Optifree | 14 | 12.5% | 11 | 31.3% |
| | 17 | Optifree | 12 | 29.4% | 12 | 29.4% |
| Pure-PDMS, Air-pretreat + methane/air plasma/IPC-2 h/IPC saline | 15 | Renu | 11 | 26.7% | 5 | 66.7% |
| | 11 | Renu | 11 | 0 | 6 | 45.4% |
| | 11 | Renu | 10 | 9.1% | 5 | 54.5% |
| | 12 | Optifree | 10 | 16.7% | 6 | 50.0% |
| | 11 | Optifree | 9 | 18.2% | 4 | 63.6% |
| | 14 | Optifree | 12 | 14.3% | 7 | 50.0% |

| | | Rubbing | 7 rubbing cycles | | 15 rubbing cycles | |
|---|---|---|---|---|---|---|
| | $FR_{0DR}$ | solution | $FR_{7DR}$ | $\Delta FR_{DR}(7)$ | $FR_{15DR}$ | $\Delta FR_{DR}(15)$ |
| Pure-PDMS, +6.00. Control (w/o coating) | 4 | Renu Optifree | 4 | | 4 | |
| Pure-PDMS, air-only plasma/1 mM PAA (pH = 2)-2 h/IPC saline | 1 | Renu | 3 | 50% | 3 | 50% |
| | 1 | Renu | 3 | 50% | 3 | 50% |
| | 1 | Renu | 3 | 50% | 3.5 | 62.5% |
| | 1 | Optifree | 3 | 50% | 3 | 50% |
| | 1 | Optifree | 3 | 50% | 3 | 50% |
| | 1 | Optifree | 3 | 50% | 3 | 50% |
| Pure-PDMS, Air-pretreat + methane/air plasma/IPC-2 h/IPC saline | 2 | Renu | 3.5 | 37.5% | 3.5 | 37.5% |
| | 2 | Renu | 3.5 | 37.5% | 3.5 | 37.5% |
| | 2 | Renu | 3.5 | 37.5% | 3.5 | 37.5% |
| | 2 | Optifree | 3.5 | 37.5% | 3.5 | 37.5% |
| | 2 | Optifree | 3.5 | 37.5% | 3.5 | 37.5% |
| | 2 | Optifree | 3.5 | 37.5% | 3.5 | 37.5% |

TABLE 19

| Elements | Control (pure-PDMS rubber lens) without any surface treatment | $CH_4$/air plasma only without any wet chemistry process |
|---|---|---|
| C | 47 | 60.9 |
| N | 0.8 | 14.5 |
| O | 29 | 20.1 |
| F | 0.7 | 0.7 |
| Si | 22.5 | 3.9 |

TABLE 20

| $CH_4$/air plasma only without any wet chemistry process | Evaluation on the second day after plasma coating | After one month in dry at room temperature, the rehydration in PBS 2 h before assessment |
|---|---|---|
| WBUT | 8 | 1 |
| FR | 4 | 4 |
| WCA(°) | 56.2 | 76 |
| Sudan black | Slightly stained | Stained |

Effect of Plasma Treatment Time

Table 21 shows the coating thickness does increase with plasma coating time, however, the lens surface properties of WBUT and lubricity are not significantly improved. Thus just increasing plasma coating time or plasma coating thickness cannot enhance the surface wettability of pure-PDMS rubber lens.

TABLE 21

| $CH_4$/air plasma min (min) | Plasma coating thickness (A°) | Plasma dry WBUT (s) | Plasma dry FR |
|---|---|---|---|
| 11 | 272 | 1 | 4 |
| 22 | 487 | 3 | 4 |
| 44 | 935 | 5 | 4 |

Effect of Combination of Plasma Treatment, PAA Quenching, and IPC

Table 22 shows the significant improvement of lens surface properties of pure-PDMS rubber lens which has been subjected to a surface treatment including plasma treatment and PAA quenching processes. The plasma gas is $CH_4$/air, and the quenching solution is 1 mM PAA (PH=2) for 20 min. The final lenses are packed in IPC saline (Example 5) and autoclaved at 120° C. for 45 min.

The lens surface properties are pretty stable for at least two months of dry storage in blister stored at room temperature. at day zero of dry storage and are determined before the medical device is dehydrated and stored in air

TABLE 22

| | Day 0 of dry storage at r.t. | 2 months of dry storage at r.t. |
|---|---|---|
| WBUT (s) | 13, 15 | 10 [$\Delta WBUT_{DS}$(60 Days) = 28.5%] |
| FR | 0, 0 | 0-1 [$\Delta FR_{DS}$(60 days) = 12.5%] |
| WCA (°) | 37 | 36 |
| Sudan black | NOT stained | NOT stained |

Examples 16

Several factors have been considered to optimize the plasma quenching conditions: (1) plasma gas; (2) quenching solution; and (3) packaging solution for autoclaving at 120° C. for 120 min.

To check the effect of plasma gas, the quenching solution is 1 mM PAA aqueous (pH=2) and quenching time in solution is fixed at 20 min. The silicone rubber lens is packed in IPC saline and autoclaved at 120° C. for 45 min. The plasma gas can affect the final lens surface properties, as shown in Table 23.

TABLE 23

| Plasma gas | Quenching for 20 min | WBUT (s) | FR | WCA (°) | Sudan Black |
|---|---|---|---|---|---|
| Air only | 1 mM PAA | 17 (in PBS 24 h, 13) | 1 (in PBS 24 h, 3) | 28 | Slightly stained |
| CH4/air | 1 mM PAA | 13 (in PBS 24 h, 7) | 0 (in PBS 24 h, 1) | 37 | NOT stained |
| Air + CH4/air | 1 mM PAA | 10 | 0 | 31 | NOT stained |

To check effect of quenching solution, Air+$CH_4$/air is fixed. Quenching time in solution is 20 min and all the lenses are packed in IPC saline and autoclaved at 120° C. for 45 min. Quenching in PAA aqueous (100 mM) is the best option, as shown in Table 24.

TABLE 24

| Plasma gas | Quenching Sol. | WBUT (s) | FR | WCA (°) | Sudan Black |
|---|---|---|---|---|---|
| Air + CH4/air | Water | 0+ | 4 | $\theta_a = 66$; $\theta_r = 12$ | Stained |
| Air + CH4/air | AA monomer aqueous | 10 | 3-4 | NA | NA |
| Air + CH4/air | 1 mM PAA | 10 | 0 | 31 | NOT stained |
| Air + CH4/air | 100 mM PAA | 18 | 0 | $\theta_a = 27$; $\theta_r = 7$ | NOT stained |

The lens surface properties in Table 25 indicate that both pH of 100 mM PAA aqueous and quenching time are the control factors to affect PAA attachment. The higher beads absorbed indicates the presence of PAA on lens surface.

TABLE 25

| | pH of PAA solution | quenching time | WBUT | FR | WCA (°) | Sudan Black | Bead test |
|---|---|---|---|---|---|---|---|
| pure-PDMS rubber lens. | 2 | 5 min | 18, 18 | 0, 0 | $\theta_a = 27$ $\theta_r = 10$ | Slightly stained | 200 |
| | 2 | 20 min | 18, 20 | 0, 0 | $\theta_a = 31$ $\theta_r = 11$ | Very slightly stained | 209 |
| Air + $CH_4$/air plasma | 4 | 5 min | 18, 16 | 2, 2 | $\theta_a = 27$ $\theta_r = 10$ | Slightly stained | 177 |
| | 4 | 20 min | 18, 18 | 1, 1 | $\theta_a = 39$ $\theta_r = 11$ | Very slightly stained | 190 |
| | 6 | 5 min | 4, 2 | 3, 3 | $\theta_a = 27$ $\theta_r = 12$ | stained | 52 |
| | 6 | 20 min | 0, 2 | 3, 3 | $\theta_a = 34$ $\theta_r = 12$ | Slightly stained | 165 |

Examples 17

Pure-PDMS rubber lenses are subjected to a surface treatment of the invention: a 3 min Air plasma pretreatment, a 11 min $CH_4$/air plasma treatment, quenching in 1 mM PAA aqueous solution (pH=2) for 20 min. After rinse the plasma quenched lenses are grouped in different conditions with soaking in PBS or IPC saline. After the treatment at 50° C. and 70° C. up to 4 h, the lenses are evaluated immediately, as shown in Table 26.

Soaking plasma quenched pure-PDMS rubber lenses in IPC saline at different heating conditions does not significantly affect the lens surface properties of WBUT, FR and water contact angle (advancing angle $\theta_a$, receding angle $\theta_r$). Soaking the lens in PBS has showed a lot of beads on lens surface, indicating that PAA can be successfully attached onto lens surface and that the surface charges can be neutralized by soaking the PAA coated lens in IPC saline even at room temperature.

After drying the lenses listed in Table 26 at room temperature overnight, the dried lenses are rehydrated in PBS. The evaluation of lens surface is collected in Table 27. It appears that the heating process in IPC saline plays key role to lens surface properties. Only the autoclaving at 120° C. for 45 min provides the favorable wettable and lubricious surface after a cycle of dehydration/rehydration.

TABLE 27

Air + CH4/air Plasma; quenched in 1 mM PAA (pH = 2) for 20 min; in IPC saline with different conditions; dried at room temperature overnight; rehydration in PBS

| Heating Process In IPC saline | WBUT (s) | FR | $\theta_a$ | $\theta_r$ |
|---|---|---|---|---|
| NO-coating | 0 | 4 | 113 | 86 |
| 50° C.-1 h | 1 | 3 | 48 | 8 |
| 50° C.-2 h | 1 | 2 | 43 | 9 |
| 50° C.-4 h | 2 | 2 | 39 | 9 |
| 70° C.-1 h | 0 | 2 | 44 | 9 |
| 70° C.-2 h | 0 | 1 | 36 | 7 |
| 70° C.-4 h | 0 | 1 | 34 | 6 |
| IPC saline autoclaved at 120° C. for 45 min | 8 | 0 | 27 | 7 |

Examples 18

Silicone rubber contact lenses are subjected to a surface treatment process: 3 min air-only plasma pretreatment+11 min $CH_4$/air plasma treatment+quenching in 100 mM PAA (pH=2) for 20 min+5 min rinsing in water+being packed in IPC saline and autoclaved at 120° C. for 45 min. The finished lenses are kept individually in blisters with IPC saline.

The lenses in Table 28 are in dry storage, there is no IPC saline at all. The lenses are kept in dry at designed storage temperature to simulating aging storage at room temperature.

After 6 week in dry storage at room temperature, the lens surface are still wettable and lubricious with WBUT>10 s and FR=0-1. Rehydration in PBS for 2 h is necessary before the data collection.

TABLE 26 heating process in saline

| saline | Temperature | time | WBUT | FR | $\theta_a$ (°) | $\theta_r$ (°) | Bead test |
|---|---|---|---|---|---|---|---|
| w/o plasma, Control | r.t. | 24 h | 0 | 4 | 113 | 86 | NA |
| PBS | r.t. | 24 h | 14, 14 | 0, 0 | 19 | 6 | 260, 265 |
| IPC saline | r.t. | 24 h | 14, 13 | 0, 0 | 26 | 8 | 0 |
| IPC saline | 120° C. | 45 min | 18, 14 | 0, 0 | 27 | 7 | 0, 40, 41 |
| IPC saline | 50° C. | 1 h | 16, 15 | 0, 0 | 33 | 8 | 12, 2 |
| IPC saline | 50° C. | 2 h | 18, 18 | 0, 0 | 31 | 8 | 13, 8 |
| IPC saline | 50° C. | 4 h | 20, 18 | 0, 0 | 33 | 7 | 10, 8 |
| IPC saline | 70° C. | 1 h | 13, 16 | 0, 0 | 38 | 8 | 0 |
| IPC saline | 70° C. | 2 h | 12, 15 | 0, 0 | 26 | 6 | 0 |
| IPC saline | 70° C. | 4 h | 15, 15 | 0, 0 | 25 | 6 | 0 |

With the simulating aging study of 6 months in dry storage, the pure-PDMS rubber lenses treated according to the surface treatment are still wettable and lubricious with WBUT>10 s and FR=1-2. The bead test has demonstrated that the negative charged PAA are still on the lens surface. Rehydration in PBS for 2 h is necessary before the data collection.

TABLE 28

| | | Temperature for Dry Storage ($T_{Storage}$) | | | | | | |
|---|---|---|---|---|---|---|---|---|
| | t = 0 (r.t.) | r.t. | 55° C. | 45° C. | 55° C. | 45° C. | 55° C. | 45° C. |
| $t_{storage}$ | 24 h | 6 weeks | 4 days | 1 week | 12 days | 23 days | 23 days | 45 days |
| $t'_{storage}$ (days) | 24 h | 42 | 30 | 30 | 90 | 90 | 180 | 180 |
| WBUT | 16 | 15 | 14 | 17 | 17 | 17 | 15 | 13 |
| $\Delta WBUT_{DS}(i)$ | — | 6.3% | 12.5% | 0 | 0 | 0 | 6.3% | 18.8% |
| FR | 0 | 1 | 1 | 1 | 1 | 1 | 2 | 2 |
| $\Delta FR_{DS}(i)$ | — | 25% | 25% | 25% | 25% | 25% | 50% | 50% |
| WCA (°) | $\theta_a = 32$ | $\theta_a = 31$ | $\theta_a = 30$ | $\theta_a = 30$ | $\theta_a = 36$ | $\theta_a = 44$ | $\theta_a = 50$ | $\theta_a = 51$ |
| | $\theta_r = 9$ | $\theta_r = 13$ | $\theta_r = 11$ | $\theta_r = 13$ | $\theta_r = 12$ | $\theta_r = 13$ | $\theta_r = 12$ | $\theta_r = 12$ |
| Sudan Black | v.s.s | s.s. | s.s. | s.s | s.s | s.s | Stained | s.s |
| Bead test | 273, 296 | 294, 314 | 312, 300 | 291, 223 | 256, 275 | 276, 325 | 250, 318 | 275, 296 | v.s.s. = "very slightly stained";
s.s. = "slightly stained";
$t_{storage}$ = Actual storage time;
$t'_{storage}$ = equivalent storage time at room temperature (r.t.)

The invention claimed is:

1. A method for producing a medical device which includes a silicone substrate and a hydrogel coating thereon, comprising the steps of:
   (1) obtaining a silicone substrate in a dry state, wherein the silicone substrate is made of a crosslinked silicone material which has three-dimensional polymer networks, is insoluble in water, and can hold less than 7.5% by weight of water when fully hydrated;
   (2) subjecting the silicone substrate in the dry state to a surface treatment to form a base coating comprising a prime plasma layer and a reactive polymer layer, wherein the surface treatment comprises the sub-steps of
      (a) plasma-treating the surface of the silicone substrate in the dry state with a plasma to form the prime plasma layer on the silicone substrate, wherein the prime plasma layer has a thickness of less than about 40 nm, wherein the plasma is generated in a plasma gas composed of air, $CO_2$, or a mixture of a $C_1$-$C_6$ hydrocarbon and a secondary gas selected from the group consisting of air, $CO_2$, $N_2$, and combinations thereof, and
      (b) contacting the plasma-treated silicone substrate with a first aqueous solution including a reactive hydrophilic polymer to form a reactive polymer layer, wherein the reactive hydrophilic polymer has multiple reactive functional groups selected from the group consisting of carboxyl groups, primary amine groups, secondary amine groups, and combinations thereof; and
   (3) heating the silicone substrate with the base coating thereon obtained in step (2), in a second aqueous solution which comprises a water-soluble and thermally-crosslinkable hydrophilic polymeric material having azetidinium groups and optionally amino or carboxyl groups, at a temperature of from about 60° C. to about 140° C. for a time period sufficient to crosslink the water-soluble thermally-crosslinkable hydrophilic polymeric material and the base coating so as to obtain the medical device which comprises the silicone substrate and a hydrogel coating thereon, wherein the medical device in fully hydrated state has a WBUT of at least about 5 seconds and a friction rating of about 3 or lower, wherein the hydrogel coating is thermodynamically stable as characterized by having a dry-storage-induced reduction in WBUT after i days of dry storage, designated as $\Delta WBUT_{DS}(i)$, of about 45% or less and optionally a dry-storage-induced increase in friction rating after i days of dry storage at room temperature, $\Delta FR_{DS}(i)$, of about 60% or less, wherein $$\Delta WBUT_{DS}(i) = \frac{WBUT_{DS@0} - WBUT_{DS@i}}{WBUT_{DS@0}} \times 100\% \text{ and}$$

$$\Delta FR_{DS}(i) = \frac{FR_{DS@i} - FR_{DS@0}}{4} \times 100\%$$

in which $WBUT_{DS@0}$ and $FR_{DS@0}$ are the WBUT and the friction rating of the medical device in fully-hydrated state at day zero of dry storage and are determined before the medical device is dehydrated and stored in air at room temperature, and $WBUT_{DS@i}$ and $FR_{DS@i}$ are the WBUT and the friction rating of the medical device in fully hydrated state at i days of dry storage and are determined after the medical device has been fully dehydrated and stored in air at room temperature for at least i days and then has been fully rehydrated before determining the WBUT and the friction rating, wherein i is an integer of 2 or larger.

2. The method of claim 1, wherein the plasma gas is composed of air.

3. The method of claim 1, wherein the plasma gas is composed of $CO_2$.

4. The method of claim 1, wherein the plasma gas is composed of a mixture of a $C_1$-$C_6$ hydrocarbon and a secondary gas selected from the group consisting of air, $CO_2$, $N_2$, and combinations thereof.

5. The method of claim 1, wherein the surface treatment further comprises, prior to substep (2)(a), a substep of plasma-pretreating the surface of the silicone substrate in the dry state with a plasma generated in a plasma gas composed of air.

6. The method of claim 1, wherein the plasma treated silicone substrate is placed in contact with the first aqueous solution within a time period of about 40 minutes or less immediately after the plasma-treatment sub-step and before contacting with water, an organic solvent, a mixture of water and one or more organic solvents, a mixture of two or more organic solvent, or any aqueous or organic-based solution free of any reactive polymer.

7. The method of claim 1, wherein the reactive hydrophilic polymer is a polyanionic polymer comprising carboxyl groups and having a weight average molecular weight of at least 1000 Daltons, and the first aqueous solution has a pH from about 1.0 to about 3.0.

8. The method of claim 7, wherein the polyanionic polymer is selected from the group consisting of polyacrylic acid, polymethacrylic acid, polyethylacrylic acid, poly(acrylic acid-co-methacrylic acid), poly(acrylic acid-co-ethacrylic acid), poly(methacrylic acid-co-ethacrylic acid), and a mixture thereof.

9. The method of claim 7, wherein the reactive hydrophilic polymer is a polycationic polymer comprising primary and/or secondary amino groups and having a weight average molecular weight of at least 1000 Daltons and the first aqueous a pH from about 9.5 to about 11.0.

10. The method of claim 9, wherein the polycationic polymer is selected from the group consisting of polyethyleneimine, polyallylamine, polyvinylamine, polyamidoamine, and a mixture thereof.

11. The method of claim 1, wherein the reactive hydrophilic polymer comprises azetidinium groups and reactive functional groups selected from the group consisting of primary groups, secondary amino groups, carboxyl groups, and combinations thereof, wherein the reactive hydrophilic polymer has a weight average molecular weight of at least 1000 Daltons, wherein the first aqueous has a pH of less than about 8.0.

12. The method of claim 3, wherein the surface treatment further comprises, prior to substep (2)(a), a substep of plasma-pretreating the surface of the silicone substrate in the dry state with a plasma generated in a plasma gas composed of air.

13. The method of claim 12, wherein the plasma treated silicone substrate is placed in contact with the first aqueous solution within a time period of about 40 minutes or less immediately after the plasma-treatment sub-step and before contacting with water, an organic solvent, a mixture of water and one or more organic solvents, a mixture of two or more organic solvent, or any aqueous or organic-based solution free of any reactive polymer.

14. The method of claim 3, wherein the plasma treated silicone substrate is placed in contact with the first aqueous solution within a time period of about 40 minutes or less immediately after the plasma-treatment sub-step and before contacting with water, an organic solvent, a mixture of water and one or more organic solvents, a mixture of two or more organic solvent, or any aqueous or organic-based solution free of any reactive polymer.

15. The method of claim 4, wherein the surface treatment further comprises, prior to substep (2)(a), a substep of plasma-pretreating the surface of the silicone substrate in the dry state with a plasma generated in a plasma gas composed of air.

16. The method of claim 15, wherein the plasma treated silicone substrate is placed in contact with the first aqueous solution within a time period of about 40 minutes or less immediately after the plasma-treatment sub-step and before contacting with water, an organic solvent, a mixture of water and one or more organic solvents, a mixture of two or more organic solvent, or any aqueous or organic-based solution free of any reactive polymer.

17. The method of claim 4, wherein the plasma treated silicone substrate is placed in contact with the first aqueous solution within a time period of about 40 minutes or less immediately after the plasma-treatment sub-step and before contacting with water, an organic solvent, a mixture of water and one or more organic solvents, a mixture of two or more organic solvent, or any aqueous or organic-based solution free of any reactive polymer.

18. The method of claim 2, wherein the surface treatment further comprises, prior to substep (2)(a), a substep of plasma-pretreating the surface of the silicone substrate in the dry state with a plasma generated in a plasma gas composed of air.

19. The method of claim 18, wherein the plasma treated silicone substrate is placed in contact with the first aqueous solution within a time period of about 40 minutes or less immediately after the plasma-treatment sub-step and before contacting with water, an organic solvent, a mixture of water and one or more organic solvents, a mixture of two or more organic solvent, or any aqueous or organic-based solution free of any reactive polymer.

20. The method of claim 2, wherein the plasma treated silicone substrate is placed in contact with the first aqueous solution within a time period of about 40 minutes or less immediately after the plasma-treatment sub-step and before contacting with water, an organic solvent, a mixture of water and one or more organic solvents, a mixture of two or more organic solvent, or any aqueous or organic-based solution free of any reactive polymer.

* * * * *